US012590121B2

(12) United States Patent (10) Patent No.: US 12,590,121 B2
Hauser et al. (45) Date of Patent: Mar. 31, 2026

(54) PEPTIDE COMPOUND WITH REPETITIVE SEQUENCES

(71) Applicant: KING ABDULLAH UNIVERSITY OF SCIENCE AND TECHNOLOGY, Thuwal (SA)

(72) Inventors: Charlotte A.E. Hauser, Thuwal (SA); Hepi Hari Susapto, Thuwal (SA)

(*) Notice: Subject to any disclaimer, the term of this patent is extended or adjusted under 35 U.S.C. 154(b) by 143 days.

(21) Appl. No.: 17/401,434

(22) Filed: Aug. 13, 2021

(65) Prior Publication Data

US 2022/0056074 A1 Feb. 24, 2022

Related U.S. Application Data

(60) Provisional application No. 63/067,913, filed on Aug. 20, 2020.

(51) Int. Cl.
| | |
|---|---|
| *C07K 5/103* | (2006.01) |
| *A61K 38/00* | (2006.01) |
| *A61L 26/00* | (2006.01) |
| *A61L 27/22* | (2006.01) |
| *A61L 27/52* | (2006.01) |
| *A61L 31/04* | (2006.01) |
| *A61L 31/14* | (2006.01) |
| *C08J 3/075* | (2006.01) |
| *C08J 3/09* | (2006.01) |
| *C12N 5/00* | (2006.01) |

(52) U.S. Cl.
CPC .......... *C07K 5/101* (2013.01); *A61L 26/0028* (2013.01); *A61L 26/008* (2013.01); *A61L 27/22* (2013.01); *A61L 27/52* (2013.01); *A61L 31/043* (2013.01); *A61L 31/145* (2013.01); *C08J 3/075* (2013.01); *C08J 3/09* (2013.01); *C12N 5/0068* (2013.01); *A61K 38/00* (2013.01); *C08J 2389/00* (2013.01); *C12N 2513/00* (2013.01); *C12N 2533/50* (2013.01)

(58) Field of Classification Search
None
See application file for complete search history.

(56) References Cited

U.S. PATENT DOCUMENTS

| | | | |
|---|---|---|---|
| 5,445,612 A | 8/1995 | Terakura et al. | |
| 8,729,032 B2 | 5/2014 | Nagai et al. | |
| 10,537,828 B2 | 1/2020 | Baxter et al. | |
| 2003/0175410 A1 | 9/2003 | Campbell et al. | |
| 2007/0154552 A1 | 7/2007 | Siegal et al. | |
| 2008/0095748 A1 | 4/2008 | Kharazi et al. | |
| 2011/0008293 A1 | 1/2011 | Bhandari | |
| 2011/0113053 A1 | 5/2011 | Khan et al. | |
| 2013/0023460 A1 | 1/2013 | Hauser et al. | |
| 2014/0012225 A1 | 1/2014 | Yoo et al. | |
| 2014/0349933 A1 | 11/2014 | Hauser et al. | |
| 2015/0038428 A1 | 2/2015 | Hauser et al. | |
| 2016/0136895 A1 | 5/2016 | Beyer et al. | |
| 2016/0288414 A1 | 10/2016 | Ozbolat et al. | |
| 2016/0375177 A1 | 12/2016 | Hauser et al. | |
| 2017/0056548 A1 | 3/2017 | Lee et al. | |
| 2017/0296760 A1 | 10/2017 | Lee et al. | |
| 2018/0030501 A1 | 2/2018 | Bourdeau et al. | |
| 2018/0118978 A1 | 5/2018 | Yabu et al. | |
| 2018/0361025 A1 | 12/2018 | Lancaster et al. | |
| 2019/0219572 A1 | 7/2019 | Mehra et al. | |
| 2019/0321291 A1 | 10/2019 | Connolly et al. | |
| 2020/0148720 A1 | 5/2020 | Hauser et al. | |
| 2020/0199514 A1 | 6/2020 | Hauser et al. | |
| 2020/0247046 A1 | 8/2020 | Malaquin et al. | |
| 2021/0114276 A1 | 4/2021 | Nelson et al. | |
| 2021/0121639 A1 | 4/2021 | Miri Ramsheh et al. | |
| 2022/0054706 A1* | 2/2022 | Hauser .................. B33Y 10/00 | |
| 2022/0371958 A1 | 11/2022 | Hauser et al. | |
| 2023/0295225 A1* | 9/2023 | Hauser .................. B33Y 80/00 | |
| | | | 514/21.9 |
| 2023/0405177 A1* | 12/2023 | Hauser .................. C07K 9/001 | |

FOREIGN PATENT DOCUMENTS

| | | |
|---|---|---|
| CN | 105085622 A | 11/2015 |
| CN | 105 881 908 A | 8/2016 |
| CN | 109224654 A | 1/2019 |
| CN | 111172100 A | 5/2020 |
| EP | 0 723 646 B1 | 7/1996 |
| JP | 2005-028216 A | 2/2005 |
| JP | 2013009598 A | 1/2013 |
| JP | 2015-13850 A | 1/2015 |
| JP | 2016-79190 A | 5/2016 |
| JP | 2016-530874 A | 10/2016 |
| JP | 2017-501136 A | 1/2017 |

(Continued)

OTHER PUBLICATIONS

Feng et al. "Development of a Potent Thrombin Receptor Ligand" J. Med. Chem. 38:4125-4130. (Year: 1995).*
Thota et al. "Molecular insights into the self-assembly of short amphiphilic peptides FmDn and FmKn" RSC Advances 4:60741 (Year: 2014).*
Restu et al. "Short Oligopeptides for Biocompatible and Biodegradable Supramolecular Hydrogels" Langmuir 34:8065-8074. (Year: 2018).*
Chakrobarty et al. "A Self-Healing, All-Organic, Conducting, Composite Peptide Hydrogel as Pressure Sensor and Electrogenic Cell Soft Substrate" ACS Nano 13:163-175. (Year: 2019).*
Li, Z.; Huang, S.; Liu, Y.; Yao, B.; Hu, T.; Shi, H.; Xie, J.; Fu, X. Scientific Reports 2018, 8, (1), 8020.

(Continued)

*Primary Examiner* — Sudhakar Katakam
*Assistant Examiner* — Zachary J Miknis
(74) *Attorney, Agent, or Firm* — Ajay A. Jagtiani; Miles & Stockbridge P.C.

(57) ABSTRACT

The present disclosure relates to ultrashort peptides capable of forming a gel, to a gel comprising a peptide in accordance with the present disclosure, and to a method of preparing such gel. Such gel is a hydrogel or an organogel. The peptides are suitable bioinks for a bioprinter to build 3D structures through 3D printing as well as other applications.

56 Claims, 22 Drawing Sheets

Specification includes a Sequence Listing.

(56)  References Cited

FOREIGN PATENT DOCUMENTS

| | | | | | |
|---|---|---|---|---|---|
| JP | 2020-519605 | A | 7/2020 | | |
| JP | 2002-320815 | A | 11/2020 | | |
| KR | 10-1596014 | B1 | 2/2016 | | |
| KR | 2016 0091993 | A | 8/2016 | | |
| KR | 20190128405 | A | * 11/2019 | ............... | A61K 8/64 |
| KR | 10-2020-0007537 | A | 1/2020 | | |
| KR | 10-2021-0104339 | A | 8/2021 | | |
| WO | 2007/102735 | A1 | 9/2007 | | |
| WO | 2008/057608 | A1 | 5/2008 | | |
| WO | WO-2008057608 | A2 * | 5/2008 | ............. | A61K 38/07 |
| WO | 2012/048755 | A1 | 4/2012 | | |
| WO | 2013/126017 | A1 | 8/2013 | | |
| WO | 2014/104981 | A1 | 7/2014 | | |
| WO | 2014/186581 | A1 | 11/2014 | | |
| WO | 2014/197999 | A1 | 12/2014 | | |
| WO | 2015/066705 | A1 | 5/2015 | | |
| WO | 2015/080670 | A1 | 6/2015 | | |
| WO | 2015/080670 | A9 | 6/2015 | | |
| WO | 2015/080671 | A1 | 6/2015 | | |
| WO | 2016/123693 | A1 | 8/2016 | | |
| WO | 2016/144259 | A1 | 9/2016 | | |
| WO | 2016/181408 | A1 | 11/2016 | | |
| WO | 2017/089963 | A1 | 6/2017 | | |
| WO | 2018/020737 | A1 | 2/2018 | | |
| WO | 2018/207036 | A1 | 11/2018 | | |
| WO | 2018/207037 | A1 | 11/2018 | | |
| WO | 2020/162835 | A1 | 8/2020 | | |
| WO | 2021/070083 | A1 | 4/2021 | | |

OTHER PUBLICATIONS

Jorgensen, W. L.; Tirado-Rives, J. Proceedings of the National Academy of Sciences of the United States of America 2005, 102, (19), 6665.
Dodda, L. S.; Cabeza de Vaca, I.; Tirado-Rives, J.; Jorgensen, W. L. Nucleic Acids Research 2017, 45, (W1), W331-W336.
Abraham, M. J.; Murtola, T.; Schulz, R.; Páll, S.; Smith, J. C.; Hess, B.; Lindahl, E. SoftwareX 2015, 1-2, 19-25.
Darden, T.; York, D.; Pedersen, L. The Journal of Chemical Physics 1993, 98, (12), 10089-10092.
Berendsen, H. J. C.; Postma, J. P. M.; Gunsteren, W. F. v.; DiNola, A.; Haak, J. R. The Journal of Chemical Physics 1984, 81, (8), 3684-3690.
Bussi, G.; Donadio, D.; Parrinello, M. The Journal of Chemical Physics 2007, 126, (1), 014101.
Kim, Y. H.; Baek, N. S.; Han, Y. H.; Chung, M.-A.; Jung, S.-D. Journal of neuroscience methods 2011, 202, (1), 38-44.
Riss, T. L.; Valley, M. P.; Zimprich, C. A.; Niles, A. L.; Kupcho, K. R.; Lazar, D. F. 60. Howe, B.; Umrigar, A.; Tsien, F. JoVE (Journal of Visualized Experiments) 2014, (83), e50203.
Howe, B.; Umrigar, A.; Tsien, F. JoVE (Journal of Visualized Experiments) 2014, (83), e50203.
Worton, R. G.; Duff, C., [27] Karyotyping. In Methods in enzymology, Elsevier: 1979; vol. 58, pp. 322-344.
Perrier, A. L.; Tabar, V.; Barberi, T.; Rubio, M. E.; Bruses, J.; Topf, N.; Harrison, N. L.; Studer, L. Proceedings of the National Academy of Sciences 2004, 101, (34), 12543-12548.
Kang, J.; Lee, I. Cardiovascular Pathology 2006, 15, (4), 218-221.
Blakely, B. D.; Bye, C. R.; Fernando, C. V.; Horne, M. K.; Macheda, M. L.; Stacker, S. A.; Arenas, E.; Parish, C. L. PloS one 2011, 6, (3), e18373.
Bowie et al., "Deciphering the Message in Protein Sequences: Tolerance to Amino Acid Substitutions", Science, vol. 47, pp. 1306-1310 (1990).
Burgess et al., "Possible Dissociation of the Heparin-binding Mitogenic Activities of Haparin-binding (Acidic Fibroblast) Growth Factor-1 from Its Receptor-binding Activities by Site-directed Mutagenesis of a Single Lysine Residue", The Journal of Cell Biology, vol. 111, pp. 2129-2138 (1990).

Loo et al, "Peptide Bioink: Printable Nanofibrous Scaffolds for 3D Organotyic Cultures", vol. 15, XP055486589 (2015).
Suspato et al, "Ultrashort Peptide Bioinks Support Automated Printing of Large-Scale Constructs Assuring Long-Term Survival of Printed Tissue Constructs", Nano Lett. 21, 7, pp. 2719-2729 (2021).
International Search Report and Written Opinion received in PCT Application No. PCT/IB2021/057622 mailed Dec. 16, 2021.
Substantive Examination Report received in Saudi Arabian Application No. 519410522.
Fichman et al., "Self-assembly of short peptides to form hydrogels: Design of building blocks, physical properties and technological applications", Acta Biomaterialia, 16, pp. 1571-1582 (2014).
Office Action received in U.S. Appl. No. 16/612,881 mailed May 20, 2021.
Office Action received in U.S. Appl. No. 16/612,881 mailed Dec. 30, 2020.
Office Action received in Korean Application No. 10-2019-7036272 mailed Oct. 21, 2022.
International Search Report and Written Opinion received in PCT Application No. PCT/IB2021/057625 mailed Dec. 14, 2021.
International Search Report and Written Opinion received in PCT Application No. PCT/IB2021/057624 mailed Dec. 13, 2021.
International Search Report and Written Opinion received in PCT Application No. PCT/IB2021/057623 mailed Dec. 13, 2021.
International Search Report and Written Opinion received in PCT Application No. PCT/IB2021/057996 mailed Dec. 20, 2021.
International Search Report and Written Opinion received in PCT Application No. PCT/IB2021/057973 mailed Dec. 20, 2021.
International Search Report and Written Opinion received in PCT Application No. PCT/IB2021/059652 mailed Feb. 3, 2022.
Susapto et al., "Ultrashort Peptide Bioinks Support Automated Printing of Large-Scale Constructs Assuring Long-Term Survival of Printed Tissue Constructs", Nano Letters, vol. 21, pp. 2719-2729 (2021).
Cembran et al., "Biomimetic Materials and Their Utility in Modeling the 3-Dimensional Neural Environment", iScience, vol. 23, pp. 1-16 (2020).
Cunha et al., "3D Culture of adult mouse neural stem cells within functionalized self-assembling peptide scaffolds", International Journal of Nanomedicine, vol. 6, pp. 943-955 (2011).
Marchini et al., "Multi-Functionalized Self-Assembling Peptides as Reproducible 3D Cell Culture Systems Enabling Differentiation and Survival of Various Human Neural Stem Cell Lines", frontiers in Neuroscience, vol. 14, Article 413, pp. 1-11 (2020).
Ranjan et al., "A microfiber scaffold-based 3D in vitro human neuronal culture model of Alzheimer's disease", The Royal Society of Chemistry, vol. 8, pp. 4861-4874 (2020).
Alshehri et al., "Scaffolds from Self-Assembling Tetrapeptides Support 3D Spreading, Osteogenic Differentiation, and Angiogenesis of Mesenchymal Stem Cells", Biomacromolecules, vol. 22, pp. 2094-2106 (2021).
Arab, "Novel Nanofibrous Peptide Scaffolds for Tissue Regeneration", PhD Thesis, Kind Abdullah University of Science and Technology, pp. 1-131 (2019).
Ikeno et al., "Effects of self-assembling peptide hydrogel scaffold on bone regeneration with recombinant human bone morphogenetic protein-2", The International Journal of Oral and Maxillofacial Implants, vol. 28, No. 5, pp. 283-289 (2013).
Liu et al., "Stiffness-mediated mesenchymal stem cell fate decision in 3D-bioprinted hydrogels", Burns and Trauma, vol. 8, pp. 1-13 (2020).
Sundararajan et al., "Use of cyanobacterial gas vesicles as oxygen carriers in cell culture", Cytotechnology, vol. 52, pp. 139-149 (2006).
Upadhyay et al., "Understanding Gas Vesicles and Its Scope in Biotechnological Applications", Advances in Biotechnology and Microbiology, vol. 11, Issue 2, pp. 1-13 (2018).
International Search Report and Written Opinion received in PCT Application No. PCT/IB2018/052173 mailed Sep. 9, 2018.
International Search Report and Written Opinion received in PCT Application No. PCT/IB2018/052189 mailed Aug. 28, 2018.

(56) References Cited

OTHER PUBLICATIONS

Office Action received in Saudi Arabian Application No. 519410522.

Office Action received in Korean Application No. 10-2019-7036277 mailed Sep. 29, 2021.

Office Action received in Saudi Arabian Application No. 519410521.

Loo et al., "Peptide Biolink: Self-Assembling Nanofibrous Scaffolds for Three-Dimensional Organotypic Cultures", Nano Letters, vol. 15, pp. 6919-6925 (2015).

Bowie et al., "Deciphering the Message in Protein Sequences: Tolerance of Amino Acid Substitutions", Science, vol. 247, pp. 1306-1310 (1990).

Burgess et al., "Possible Dissociation of the Heparin-binding Mitogenic Activities of Heparin-binding (Acid Fibroblast) Growth Factor-1 from Its Receptor-binding Activities by Site-directed Mutagenesis of a Single Lysine Residue", The Journal of Cell Biology, vol. 111, pp. 2129-2138 (1990).

Loo et al., "Peptide Bioink: Printable Nanofibrous Scaffolds for 3D Organotypic Cultures", vol. 15, XP055486589 (2015).

Fichman et al., "Self-assembly of short peptides to form hydrogels: Design of building blocks, physical properties and technological applications", Acta Biomaterials, vol. 10, pp. 1671-1682 (2014).

Gauthaman, K.; Venugopal, J. R.; Yee, F. C.; Biswas, A.; Ramakrishna, S.; Bongso, A. Osteogenic differentiation of human Wharton's jelly stem cells on nanofibrous substrates in vitro. Tissue Eng., Part A 2011, 17, 71-81.

Leng, Q.; Chen, L.; Lv, Y. RNA-based scaffolds for bone regeneration: application and mechanisms of mRNA, miRNA and siRNA. Theranostics 2020, 10, 3190.

Erdem, A.; Darabi, M. A.; Nasiri, R.; Sangabathuni, S.; Ertas, Y. N.; Alem, H.; Hosseini, V.; Shamloo, A.; Nasr, A. S.; Ahadian, S. 3D Bioprinting of Oxygenated Cell-Laden Gelatin Methacryloyl Constructs. Adv. Healthcare Mater. 2020, 9, No. 1901794.

Myeroff, C.; Archdeacon, M. Autogenous bone graft: donor sites and techniques. J. Bone Jt. Surg. 2011, 93, 2227-2236.

Silbernagel, N.; Körner, A.; Balitzki, J.; Jaggy, M.; Bertels, S.; Richter, B.; Hippler, M.; Hellwig, A.; Hecker, M.; Bastmeyer, M.; Ullrich, N. D. Shaping the Heart: Structural and Functional Maturation of iPSC-Cardiomyocytes in 3D-Micro-Scaffolds. Biomaterials 2020, 227, No. 119551.

Silber, J. S.; Anderson, D. G.; Daffner, S. D.; Brislin, B. T.; Leland, J. M.; Hilibrand, A. S.; Vaccaro, A. R.; Albert, T. J. Donor site morbidity after anterior iliac crest bone harvest for single-level anterior cervical discectomy and fusion. Spine 2003, 28, 134-139.

Alonzo, M.; Alvarez Primo, F.; Anil Kumar, S.; Mudloff, J. A.; Dominguez, E.; Fregoso, G.; Ortiz, N.; Weiss, W. M.; Joddar, B. Bone tissue engineering techniques, advances, and scaffolds for treatment of bone defects. Curr. Opin. Biomed. Eng. 2021, 17, No. 100248.

Amini, A. R.; Laurencin, C. T.; Nukavarapu, S. P. Bone tissue engineering: recent advances and challenges. Crit. Rev. Biomed. Eng. 2012, 40, 363-408.

Bharadwaz, A.; Jayasuriya, A. C. Recent trends in the application of widely used natural and synthetic polymer nanocomposites in bone tissue regeneration. Mater. Sci. Eng., C 2020, 110, No. 110698.

Pittenger, M. F.; Mackay, A. M.; Beck, S. C.; Jaiswal, R. K.; Douglas, R.; Mosca, J. D.; Moorman, M. A.; Simonetti, D. W.; Craig, S.; Marshak, D. R. Multilineage potential of adult human mesenchymal stem cells. Science 1999, 284, 143-147.

Ma, K.; Laco, F.; Ramakrishna, S.; Liao, S.; Chan, C. K. Differentiation of bone marrow-derived mesenchymal stem cells into multi-layered epidermis-like cells in 3D organotypic coculture. Biomaterials 2009, 30, 3251-3258.

Petite, H.; Viateau, V.; Bensaid, W.; Meunier, A.; de Pollak, C.; Bourguignon, M.; Oudina, K.; Sedel, L.; Guillemin, G. Tissue-engineered bone regeneration. Nat. Biotechnol. 2000, 18, 959.

Takamine, Y.; Tsuchiya, H.; Kitakoji, T.; Kurita, K.; Ono, Y.; Ohshima, Y.; Kitoh, H.; Ishiguro, N.; Iwata, H. Distraction osteogenesis enhanced by osteoblastlike cells and collagen gel. Clin. Orthop. Relat. Res. 2002, 399, 240-246.

Kofidis, T.; Lebl, D. R.; Martinez, E. C.; Hoyt, G.; Tanaka, M.; Robbins, R. C. Novel injectable bioartificial tissue facilitates targeted, less invasive, large-scale tissue restoration on the beating heart after myocardial injury. Circulation 2005, 112, 1-173-1-177.

Yildirim, Y.; Naito, H.; Didié, M.; Karikkineth, B. C.; Biermann, D.; Eschenhagen, T.; Zimmermann, W.-H. Development pf a biological ventricular assist device: preliminary data from a small animal model. Circulation 2007, 116, I-16-I-23.

Radisic, M.; Park, H.; Shing, H.; Consi, T.; Schoen, F. J.; Langer, R.; Freed, L. E.; Vunjak-Novakovic, G. Functional assembly of engineered myocardium by electrical stimulation of cardiac myocytes cultured on scaffolds. Proc. Natl. Acad. Sci. U.S.A. 2004, 101, 18129-18134.

Spadaccio, C.; Chachques, E.; Chello, M.; Covino, E.; Chachques, J. C.; Genovese, J. Predifferentiated adult stem cells and matrices for cardiac cell therapy. Asian Cardiovasc. Thorac. Ann. 2010, 18, 79-87.

Kutschka, I.; Chen, I. Y.; Kofidis, T.; Arai, T.; Von Degenfeld, G.; Sheikh, A. Y.; Hendry, S. L.; Pearl, J.; Hoyt, G.; Sista, R.; et al. Collagen matrices enhance survival of transplanted cardiomyoblasts and contribute to functional improvement of ischemic rat hearts. Circulation 2006, 114, I-167-I-173.

Orkin, R.; Gehron, P.; Mcgoodwin, E. B.; Martin, G.; Valentine, T.; Swarm, R. A murine tumor producing a matrix of basement membrane. J. Exp. Med. 1977, 145, 204-220.

Sethi, T.; Rintoul, R. C.; Moore, S. M.; Mackinnon, A. C.; Salter, D.; Choo, C.; Chilvers, E. R.; Dransfield, I.; Donnelly, S. C.; Strieter, R.; et al. Extracellular matrix proteins protect small cell lung cancer cells against apoptosis: a mechanism for small cell lung cancer growth and drug resistance in vivo. Nat. Med. 1999, 5, 662-668.

Grant, D.; Kibbey, M.; Kinsella, J.; Cid, M.; Kleinman, H. The role of basement membrane in angiogenesis and tumor growth. Pathol., Res. Pract. 1994, 190, 854-863.

Fushimi, H.; Hiratsuka, T.; Okamura, A.; Ono, Y.; Ogura, I.; Nishimura, I. Recombinant collagen polypeptide as a versatile bone graft biomaterial. Commun. Mater. 2020, 1, No. 1.

Kang, P. L.; Huang, H. H.; Chen, T.; Ju, K. C.; Kuo, S. M. Angiogenesis-promoting effect of LIPUS on hADSCs and HUVECs cultured on collagen/hyaluronan scaffolds. Mater. Sci. Eng., C 2019, 102, 22-33.

Blokhuis, T.; Arts, J. C. Bioactive and osteoinductive bone graft substitutes: definitions, facts and myths. Injury 2011, 42, S26-S29.

Barradas, A.; Yuan, H.; van Blitterswijk, C. A.; Habibovic, P. Osteoinductive biomaterials: current knowledge of properties, experimental models and biological mechanisms. Eur. Cells Mater. 2011, 21, 407-429.

Habibovic, P.; de Groot, K. Osteoinductive biomaterials 掘 properties and relevance in bone repair. J. Tissue Eng. Regener. Med. 2007, 1, 25-32.

Ramier, J.; Grande, D.; Bouderlique, T.; Stoilova, O.; Manolova, N.; Rashkov, I.; Langlois, V.; Albanese, P.; Renard, E. From design of bio-based biocomposite electrospun scaffolds to osteogenic differentiation of human mesenchymal stromal cells. J. Mater. Sci. Mater. Med. 2014, 25, 1563-1575.

Adler-Abramovich, L.; Gazit, E. The physical properties of supramolecular peptide assemblies: from building block association to technological applications. Chem. Soc. Rev. 2014, 43, 6881-6893.

Biesalski, M. A.; Knaebel, A.; Tu, R.; Tirrell, M. Cell adhesion on a polymerized peptide-amphiphile monolayer. Biomaterials 2006, 27, 1259-1269.

Mata, A.; Hsu, L.; Capito, R.; Aparicio, C.; Henrikson, K.; Stupp, S. I. Micropatterning of bioactive self-assembling gels. Soft Matter 2009, 5, 1228-1236.

Eren, E. D.; Tansik, G.; Tekinay, A. B.; Guler, M. O. Mineralized peptide nanofiber gels for enhanced osteogenic differentiation. ChemNanoMat 2018, 4, 837-845.

Mata, A.; Geng, Y.; Henrikson, K. J.; Aparicio, C.; Stock, S. R.; Satcher, R. L.; Stupp, S. I. Bone regeneration mediated by biomimetic mineralization of a nanofiber matrix. Biomaterials 2010, 31, 6004-6012.

(56)          References Cited

OTHER PUBLICATIONS

Derkus, B.; Okesola, B. O.; Barrett, D. W.; D'Este, M.; Chowdhury, T. T.; Eglin, D.; Mata, A. Multicomponent hydrogels for the formation of vascularized bone-like constructs in vitro. Acta Biomater. 2020, 109, 82-94.

Ghosh, M.; Halperin-Sternfeld, M.; Grigoriants, I.; Lee, J.; Nam, K. T.; Adler-Abramovich, L. Arginine-presenting peptide hydrogels decorated with hydroxyapatite as biomimetic scaffolds for bone regeneration. Biomacromolecules 2017, 18, 3541-3550.

Tsutsumi, H.; Kawamura, M.; Mihara, H. Osteoblastic differentiation on hydrogels fabricated from Ca2+-responsive self-assembling peptides functionalized with bioactive peptides. Bioorg. Med. Chem. 2018, 26, 3126-3132.

Zhang, R.; Liu, Y.; Qi, Y.; Zhao, Y.; Nie, G.; Wang, X.; Zheng, S. Self-assembled peptide hydrogel scaffolds with VEGF and BMP-2 Enhanced in vitro angiogenesis and osteogenesis. Oral Dis. 2021, DOI: 10.1111/odi.13785, in press.

Misawa, H.; Kobayashi, N.; Soto-Gutierrez, A.; Chen, Y.; Yoshida, A.; Rivas-Carrillo, J. D.; Navarro-Alvarez, N.; Tanaka, K.; Miki, A.; Takei, J.; et al. PuraMatrix facilitates bone regeneration in bone defects of calvaria in mice. Cell Transplant. 2006, 15, 903-910.

Ikeno, M.; Hibi, H.; Kinoshita, K.; Hattori, H.; Ueda, M. Effects of self-assembling peptide hydrogel scaffold on bone regeneration with recombinant human bone morphogenetic protein-2. Int. J. Oral Maxillofac. Implants 2013, 28, e283-9.

He, B.; Ou, Y.; Chen, S.; Zhao, W.; Zhou, A.; Zhao, J.; Li, H.; Jiang, D.; Zhu, Y. Designer bFGF-incorporated d-form self-assembly peptide nanofiber scaffolds to promote bone repair. Mater. Sci. Eng., C 2017, 74, 451-458.

Tsukamoto, J.; Naruse, K.; Nagai, Y.; Kan, S.; Nakamura, N.; Hata, M.; Omi, M.; Hayashi, T.; Kawai, T.; Matsubara, T. Efficacy of a self-assembling peptide hydrogel, SPG-178-gel, for bone regeneration and three-dimensional osteogenic induction of dental pulp stem cells. Tissue Eng., Part A 2017, 23, 1394-1402.

Sun, Y.; Li, W.; Wu, X.; Zhang, N.; Zhang, Y.; Ouyang, S.; Song, X.; Fang, X.; Seeram, R.; Xue, W.; He, L.; Wu, W. Functional Self-Assembling Peptide Nanofiber Hydrogels Designed for Nerve Degeneration. ACS Appl. Mater. Interfaces 2016, 8, 2348-2359.

Guo, J.; Su, H.; Zeng, Y.; Liang, Y.-X.; Wong, W. M.; Ellis-Behnke, R. G.; So, K.-F.; Wu, W. Reknitting the injured spinal cord by self-assembling peptide nanofiber scaffold. Nanomedicine 2007, 3, 311-321.

Liu, X.; Wang, X.; Wang, X.; Ren, H.; He, J.; Qiao, L.; Cui, F.-Z. Functionalized self-assembling peptide nanofiber hydrogels mimic stem cell niche to control human adipose stem cell behavior in vitro. Acta Biomater. 2013, 9, 6798 -6805.

Rauf, S.; Susapto, H. H.; Kahin, K.; Alshehri, S.; Abdelrahman, S.; Lam, J. H.; Asad, S.; Jadhav, S.; Sundaramurthi, D.; Gao, X.; Hauser, C. A. E. Self-assembling tetrameric peptides allow in situ 3D bioprinting under physiological conditions. J. Mater. Chem. B 2021, 9, 1069-1081.

Susapto, H. H.; Alhattab, D.; Abdelrahman, S.; Khan, Z.; Alshehri, S.; Kahin, K.; Ge, R.; Moretti, M.; Emwas, A.-H.; Hauser, C. A. E. Ultrashort Peptide Bioinks Support Automated Printing of Large-Scale Constructs Assuring Long-Term Survival of Printed Tissue Constructs. Nano Lett. 2021, 21, 2719-2729.

Arthur, A.; Zannettino, A.; Gronthos, S. The therapeutic applications of multipotential mesenchymal/stromal stem cells in skeletal tissue repair. J. Cell. Physiol. 2009, 218, 237-245.

Polo-Corrales, L.; Latorre-Esteves, M.; Ramirez-Vick, J. E. Scaffold design for bone regeneration. J. Nanosci. Nanotechnol. 2014, 14, 15-56.

Holmes, T. C. Novel peptide-based biomaterial scaffolds for tissue engineering. Trends Biotechnol. 2002, 20, 16-21.

Hauser, C. A.; Deng, R.; Mishra, A.; Loo, Y.; Khoe, U.; Zhuang, F.; Cheong, D. W.; Accardo, A.; Sullivan, M. B.; Riekel, C.; Ying, J. Y.; Hauser, U. A. Natural tri- to hexapeptides self-assemble in water to amyloid beta-type fiber aggregates by unexpected alpha-helical intermediate structures. Proc. Natl. Acad. Sci. U.S.A. 2011, 108, 1361-1366.

Lei, Y.; Gojgini, S.; Lam, J.; Segura, T. The spreading, migration and proliferation of mouse mesenchymal stem cells cultured inside hyaluronic acid hydrogels. Biomaterials 2011, 32, 39-47.

Examination Report received in Saudi Arabian Application No. 519410522 dated Aug. 2, 2022.

Search Report and Written Opinion received in PCT Application No. PCT/IB2022/051913 mailed Jun. 14, 2022.

Office Action received in U.S. Appl. No. 16/612,580 dated Jun. 6, 2022.

Bowie et al., "Deciphering the Message in Protein Sequences: Tolderance to Amino Acid Substitutions", Science, vol. 249, pp. 1306-1310 (1990).

Burgess et al., "Possible dissociation of the heparin-binding and mitogenic activities of heparin-binding (acidic fibroblast) growth factor-1 from its receptor-binding activities by site-directed mutagenesis of a single lysine residue", J. cell Biol, vol. 111, pp. 2129-2138 (1990).

Loo et al., "Peptide Bioink: Self-Assembling Nanofibrous Scaffolds for Three-Dimensional Organotypic Cultures", vol. 15, pp. 1-13, XP055486589 (2015).

Gungor-Ozkerim, P. S.; Inci, I.; Zhang, Y. S.; Khademhosseini, A.; Dokmeci, M. R. Biomaterials Science 2018, 6, (5), 915-946.

Donderwinkel, I.; van Hest, J. C. M.; Cameron, N. R. Polymer Chemistry 2017, 8, (31), 4451-4471.

Gopinathan, J.; Noh, I. Biomater Res 2018, 22, 11-11.

Khademhosseini, A.; Camci-Unal, G., 3D Bioprinting in Regenerative Engineering:: Principles and Applications. CRC Press: 2018.

Gjorevski, N.; Sachs, N.; Manfrin, A.; Giger, S.; Bragina, M. E.; Ordonez-Moran, P.; Clevers, H.; Lutolf, M. P. Nature 2016, 539, (7630), 560-564.

Hauser, C. A. E.; Deng, R.; Mishra, A.; Loo, Y.; Khoe, U.; Zhuang, F.; Cheong, D. W.; Accardo, A.; Sullivan, M. B.; Riekel, C.; Ying, J. Y.; Hauser, U. A. Proceedings of the National Academy of Sciences 2011, 108, (4), 1361-1366.

Loo, Y.; Lakshmanan, A.; Ni, M.; Toh, L. L.; Wang, S.; Hauser, C. A. E. Nano Letters 2015, 15, (10), 6919-6925.

Seow, W. Y.; Salgado, G.; Lane, E. B.; Hauser, C. A. E. Scientific Reports 2016, 6, 32670.

Chan, K. H.; Xue, B.; Robinson, R. C.; Hauser, C. A. E. Scientific Reports 2017, 7, (1), 12897.

Wang, H.; Ren, C.; Song, Z.; Wang, L.; Chen, X.; Yang, Z. Nanotechnology 2010, 21, (22), 225606.

Raeburn, J.; Pont, G.; Chen, L.; Cesbron, Y.; Levy, R.; Adams, D. J. Soft Matter 2012, 8, (4), 1168-1174.

Betush, R. J.; Urban, J. M.; Nilsson, B. L. Peptide Science 2018, 110, (1), e23099.

Lakshmanan, A.; Cheong, D. W.; Accardo, A.; Di Fabrizio, E.; Riekel, C.; Hauser, C. A. Proc Natl Acad Sci U S A 2013, 110, (2), 519-24.

Bowerman, C. J.; Ryan, D. M.; Nissan, D. A.; Nilsson, B. L. Molecular BioSystems 2009, 5, (9), 1058-1069.

Senguen, F. T.; Lee, N. R.; Gu, X.; Ryan, D. M.; Doran, T. M.; Anderson, E. A.; Nilsson, B. L. Molecular BioSystems 2011, 7, (2), 486-496.

Surewicz, W. K.; Mantsch, H. H.; Chapman, D. Biochemistry 1993, 32, (2), 389-394.

Goormaghtigh, E.; Cabiaux, V.; Ruysschaert, J.-M. European Journal of Biochemistry 1990, 193, (2), 409-420.

Williams, R. W.; Dunker, A. K. Journal of Molecular Biology 1981, 152, (4), 783-813.

Rivas-Arancibia, S.; Rodríguez-Martínez, E.; Badillo-Ramírez, I.; López-González, U.; Saniger, J. M. Frontiers in Molecular Neuroscience 2017, 10, (137).

Seow, W. Y.; Salgado, G.; Lane, E. B.; Hauser, C. A. E. Scientific Reports 2016, 6.

Tuncaboylu, D. C.; Argun, A.; Sahin, M.; Sari, M.; Okay, O. Polymer 2012, 53, (24), 5513-5522.

Murphy, S. V.; Atala, A. Nature Biotechnology 2014, 32, (8), 773-785.

Grinnell, F. Trends in cell biology 2003, 13, (5), 264-269.

Franco-Barraza, J.; Beacham, D. A.; Amatangelo, M. D.; Cukierman, E. Current protocols in cell biology 2016, 71, (1), 10.9. 1-10.9. 34.

(56)　　　　　References Cited

OTHER PUBLICATIONS

Seliktar, D. Science 2012, 336, (6085), 1124-1128.

Baker, B. M.; Chen, C. S. Journal of cell science 2012, 125, (13), 3015-3024.

Even-Ram, S.; Yamada, K. M. Current opinion in cell biology 2005, 17, (5), 524-532.

Lutolf, M. P.; Lauer-Fields, J. L.; Schmoekel, H. G.; Metters, A. T.; Weber, F. E.; Fields, G. B.; Hubbell, J. A. Proceedings of the National Academy of Sciences 2003, 100, (9), 5413-5418.

Mazzeo, M. S.; Chai, T.; Daviran, M.; Schultz, K. M. ACS applied bio materials 2018, 2, (1), 81-92.

Discher, D. E.; Mooney, D. J.; Zandstra, P. W. Science 2009, 324, (5935), 1673-1677.

Engler, A. J.; Sen, S.; Sweeney, H. L.; Discher, D. E. Cell 2006, 126, (4), 677-689.

Chaudhuri, O.; Gu, L.; Klumpers, D.; Darnell, M.; Bencherif, S. A.; Weaver, J. C.; Huebsch, N.; Lee, H.-p.; Lippens, E.; Duda, G. N. Nature materials 2016, 15, (3), 326-334.

Dalby, M. J.; Gadegaard, N.; Tare, R.; Andar, A.; Riehle, M. O.; Herzyk, P.; Wilkinson, C. D.; Oreffo, R. O. Nature materials 2007, 6, (12), 997-1003.

Haugh, M. G.; Vaughan, T. J.; Madl, C. M.; Raftery, R. M.; McNamara, L. M.; O'Brien, F. J.; Heilshorn, S. C. Biomaterials 2018, 171, 23-33.

Silbernagel, N.; Körner, A.; Balitzki, J.; Jaggy, M.; Bertels, S.; Richter, B.; Hippler, M.; Hellwig, A.; Hecker, M.; Bastmeyer, M. Biomaterials 2020, 227, 119551.

Darnell, M.; Gu, L.; Mooney, D. Biomaterials 2018, 181, 182-188.

Kahin, K.; Khan, Z.; Albagami, M.; Usman, S.; Bahnshal, S.; Alwazani, H.; Majid, M.; Rauf, S.; Hauser, C. In Development of a robotic 3D bioprinting and microfluidic pumping system for tissue and organ engineering, Microfluidics, BioMEMS, and Medical Microsystems XVII, 2019; International Society for Optics and Photonics: p. 108750Q.

Mouser, V. H. M.; Melchels, F. P. W.; Visser, J.; Dhert, W. J. A.; Gawlitta, D.; Malda, J. Biofabrication 2016, 8, (3), 035003.

Chimene, D.; Peak, C. W.; Gentry, J. L.; Carrow, J. K.; Cross, L. M.; Mondragon, E.; Cardoso, G. B.; Kaunas, R.; Gaharwar, A. K. ACS Applied Materials & Interfaces 2018, 10, (12), 9957-9968.

Bertassoni, L. E.; Cardoso, J. C.; Manoharan, V.; Cristino, A. L.; Bhise, N. S.; Araujo, W. A.; Zorlutuna, P.; Vrana, N. E.; Ghaemmaghami, A. M.; Dokmeci, M. R. Biofabrication 2014, 6, (2), 024105.

Markstedt, K.; Mantas, A.; Tournier, I.; Martínez Ávila, H. c.; Hagg, D.; Gatenholm, P. Biomacromolecules 2015, 16, (5), 1489-1496.

Wilson, S. A.; Cross, L. M.; Peak, C. W.; Gaharwar, A. K. ACS applied materials & interfaces 2017, 9, (50), 43449-43458.

Bernal, P. N.; Delrot, P.; Loterie, D.; Li, Y.; Malda, J.; Moser, C.; Levato, R. Advanced materials 2019, 31, (42), 1904209.

Kang, H.-W.; Lee, S. J.; Ko, I. K.; Kengla, C.; Yoo, J. J.; Atala, A. Nature biotechnology 2016, 34, (3), 312.

Hwang, T. L.; Shaka, A. J. Journal of Magnetic Resonance, Series A 1995, 112, (2), 275-279. 46. Derome, A. E.; Williamson, M. P. Journal of Magnetic Resonance (1969) 1990, 88, (1), 177-185.

Piotto, M.; Saudek, V.; Sklenář, V. Journal of Biomolecular NMR 1992, 2, (6), 661-665. 48. Sklenar, V.; Piotto, M.; Leppik, R.; Saudek, V. Journal of Magnetic Resonance, Series A 1993, 102, (2), 241-245.

Derome, A. E.; Williamson, M. P. Journal of Magnetic Resonance (1969) 1990, 88, (1), 177-185.

Sklenar, V.; Piotto, M.; Leppik, R.; Saudek, V. Journal of Magnetic Resonance, Series A 1993, 102, (2), 241-245.

Micsonai, A.; Wien, F.; Kernya, L.; Lee, Y.-H.; Goto, Y.; Réfrégiers, M.; Kardos, J. Proceedings of the National Academy of Sciences 2015, 112, (24), E3095.

Maiti, N. C.; Apetri, M. M.; Zagorski, M. G.; Carey, P. R.; Anderson, V. E. Journal of the American Chemical Society 2004, 126, (8), 2399-2408.

Loo, Y.; Chan, Y. S.; Szczerbinska, I.; Tan, B. C.; Wan, A. C.; Ng, H. H.; Hauser, C. A. A Chemically Well-Defined, Self-Assembling 3D Substrate for Long-Term Culture of Human Pluripotent Stem Cells. ACS Appl. Bio Mater. 2019, 2, 1406-1412.

Lee, J. H.; Jung, H. W.; Kang, I.-K.; Lee, H. B. Cell behaviour on polymer surfaces with different functional groups. Biomaterials 1994, 15, 705-711.

Guo, S.; Zhu, X.; Li, M.; Shi, L.; Ong, J. L. T.; Janczewski,D.; Neoh, K. G. Parallel Control over Surface Charge and Wettability Using Polyelectrolyte Architecture: Effect on Protein Adsorption and Cell Adhesion. ACS Appl. Mater. Interfaces 2016, 8, 30552-30563.

Hauser, C. A. E.; Zhang, S. Designer self-assembling peptide nanofiber biological materials. Chem. Soc. Rev. 2010, 39, 2780-2790.

Bowerman, C. J.; Ryan, D. M.; Nissan, D. A.; Nilsson, B. L. The Effect of Increasing Hydrophobicity on the Self-Assembly of Amphipathic B-Sheet Peptides. Mol. Biosyst. 2009, 5, 1058-1069.

Susapto, H. H.; Alhattab, D.; Abdelrahman, S.; Khan, Z.; Alshehri, S.; Kahin, K.; Ge, R.; Moretti, M.; Emwas, A. H.; Hauser, C. A. E. Ultrashort Peptide Bioinks Support Automated Printing of Large-Scale Constructs Assuring Long- Term Survival of Printed Tissue Constructs. Nano Lett. 2021, 2719.

Friedrichs, J.; Taubenberger, A.; Franz, C. M.; Muller, D. J. Cellular Remodelling of Individual Collagen Fibrils Visualized by Time-lapse AFM. J. Mol. Biol. 2007, 372, 594-607.

Nakayama, M.; Amano, M.; Katsumi, A.; Kaneko, T.; Kawabata, S.; Takefuji, M.; Kaibuchi, K. Rho-kinase and myosin II activities are required for cell type and environment specific migration. Genes Cells 2005, 10, 107-117.

Beadle, C.; Assanah, M. C.; Monzo, P.; Vallee, R.; Rosenfeld, S. S.; Canoll, P. The Role of Myosin II in Glioma Invasion of the Brain. Mol. Biol. Cell 2008, 19, 3357-3368.

Friedl, P.; Wolf, K.; Lammerding, J. Nuclear mechanics during cell migration. Curr. Opin. Cell Biol. 2011, 23, 55-64.

Balzer, E. M.; Tong, Z.; Paul, C. D.; Hung, W.-C.; Stroka, K. M.; Boggs, A. E.; Martin, S. S.; Konstantopoulos, K. Physical confinement alters tumor cell adhesion and migration phenotypes. FASEB J. 2012, 26, 4045-4056.

Khatau, S. B.; Bloom, R. J.; Bajpai, S.; Razafsky, D.; Zang, S.; Giri, A.; Wu, P.-H.; Marchand, J.; Celedon, A.; Hale, C. M.; Sun, S. X.; Hodzic, D.; Wirtz, D. The distinct roles of the nucleus and nucleus-cytoskeleton connections in three-dimensional cell migration. Sci. Rep. 2012, 2, No. 488.

Wen, J. H.; Vincent, L. G.; Fuhrmann, A.; Choi, Y. S.; Hribar, K. C.; Taylor-Weiner, H.; Chen, S.; Engler, A. J. Interplay of matrix stiffness and protein tethering in stem cell differentiation. Nat. Mater. 2014, 13, 979-987.

Thievessen, I.; Thompson, P. M.; Berlemont, S.; Plevock, K. M.; Plotnikov, S. V.; Zemljic-Harpf, A.; Ross, R. S.; Davidson, M. W.; Danuser, G.; Campbell, S. L.; Waterman, C. M. Vinculin-actin interaction couples actin retrograde low to focal adhesions, but is dispensable for focal adhesion growth. J. Cell Biol. 2013, 202, 163-177.

Humphries, J. D.; Wang, P.; Streuli, C.; Geiger, B.; Humphries, M. J.; Ballestrem, C. Vinculin controls focal adhesion formation by direct interactions with talin and actin. J. Cell. Biol. 2007, 179, 1043-1057.

Ode, A.; Schoon, J.; Kurtz, A.; Gaetjen, M.; Ode, J. E.; Geissler, S.; Duda, G. N. CD73/5'-ecto-nucleotidase acts as a regulatory factor in osteo-/chondrogenic differentiation of mechanically stimulated mesenchymal stromal cells. Eur. Cells Mater. 2013, 25, 37-47.

Aslan, H.; Zilberman, Y.; Kandel, L.; Liebergall, M.; Oskouian, R. J.; Gazit, D.; Gazit, Z. Osteogenic differentiation of honcultured immunoisolated bone marrow-derived CD105+ cells. Stem Cells 2006, 24, 1728-1737.

Huang, S.; Ingber, D. E. The structural and mechanical complexity of cell-growth control. Nat. Cell Biol. 1999, 1, No. E131.

McBeath, R.; Pirone, D. M.; Nelson, C. M.; Bhadriraju, K.; Chen, C. S. Cell shape, cytoskeletal tension, and RhoA regulate stem cell lineage commitment. Dev. Cell 2004, 6, 483-495.

Katz, B.-Z.; Zamir, E.; Bershadsky, A.; Kam, Z.; Yamada, K. M.; Geiger, B. Physical state of the extracellular matrix regulates the structure and molecular composition of cell-matrix adhesions. Mol. Biol. Cell 2000, 11, 1047-1060.

(56)         References Cited

OTHER PUBLICATIONS

Cukierman, E.; Pankov, R.; Stevens, D. R.; Yamada, K. M. Taking cell-matrix adhesions to the third dimension. Science 2001, 294, 1708-1712.

Fischbach, C.; Kong, H. J.; Hsiong, S. X.; Evangelista, M.B.; Yuen, W.; Mooney, D. J. Cancer cell angiogenic capability is regulated by 3D culture and integrin engagement. Proc. Natl. Acad. Sci. U.S.A. 2009, 106, 399-404.

Hsiong, S. X.; Boontheekul, T.; Huebsch, N.; Mooney, D. J. Cyclic arginine-glycine-aspartate peptides enhance three-dimensional stem cell osteogenic differentiation. Tissue Eng., Part A 2009, 15, 263-272.

Park, J. S.; Huang, N. F.; Kurpinski, K. T.; Patel, S.; Hsu, S.; Li, S. Mechanobiology of mesenchymal stem cells and their use in cardiovascular repair. Front. Biosci. 2007, 12, 5098-5116.

Tan, S.; Fang, J. Y.; Yang, Z.; Nimni, M. E.; Han, B. The synergetic effect of hydrogel stiffness and growth factor on osteogenic differentiation. Biomaterials 2014, 35, 5294-5306.

Knight, B.; Laukaitis, C.; Akhtar, N.; Hotchin, N. A.; Edlund, M.; Horwitz, A. R. Visualizing muscle cell migration in situ. Curr. Biol. 2000, 10, 576-585.

Roskelley, C.; Desprez, P.; Bissell, M. Extracellular matrix- dependent tissue-specific gene expression in mammary epithelial cells requires both physical and biochemical signal transduction. Proc. Natl. Acad. Sci. U.S.A. 1994, 91, 12378-12382.

Thievessen, I.; Fakhri, N.; Steinwachs, J.; Kraus, V.; Mclsaac, R. S.; Gao, L.; Chen, B.-C.; Baird, M. A.; Davidson, M. W.; Betzig, E.; et al. Vinculin is required for cell polarization, migration, and extracellular matrix remodeling in 3D collagen. FASEB J. 2015, 29, 4555-4567.

Case, L. B.; Baird, M. A.; Shtengel, G.; Campbell, S. L.; Hess, H. F.; Davidson, M. W.; Waterman, C. M. Molecular mechanism of vinculin activation and nanoscale spatial organization in focal adhesions. Nat. Cell Biol. 2015, 17, 880-892.

Carisey, A.; Ballestrem, C. Vinculin, an adapter protein in control of cell adhesion signalling. Eur. J. Cell Biol. 2011, 90, 157-163.

Xu, W.; Baribault, H.; Adamson, E. D. Vinculin knockout results in heart and brain defects during embryonic development. Development 1998, 125, 327-337.

Kumar, G.; Tison, C. K.; Chatterjee, K.; Pine, P. S.; McDaniel, J. H.; Salit, M. L.; Young, M. F.; Simon, C. G., Jr. The determination of stem cell fate by 3D scaffold structures through the control of cell shape. Biomaterials 2011, 32, 9188 -9196.

Pablo Rodriguez, J.; Gonzalez, M.; Rios, S.; Cambiazo, V. Cytoskeletal organization of human mesenchymal stem cells (MSC) changes during their osteogenic differentiation. J. Cell. Biochem. 2004, 93, 721-731.

Treiser, M. D.; Yang, E. H.; Gordonov, S.; Cohen, D. M.; Androulakis, I. P.; Kohn, J.; Chen, C. S.; Moghe, P. V. Cytoskeleton-based forecasting of stem cell lineage fates. Proc. Natl. Acad. Sci. U.S.A. 2010, 107, 610-615.

Hunter, G. K.; Hauschka, P. V.; Poole, R. A.; Rosenberg, L. C.; Goldberg, H. A. Nucleation and inhibition of hydroxyapatite formation by mineralized tissue proteins. Biochem. J. 1996, 317, 59-64.

Wang, J.; Cui, X.; Zhou, Y.; Xiang, Q. Core-shell PLGA/ collagen nanofibers loaded with recombinant FN/CDHs as bone tissue engineering scaffolds. Connect. Tissue Res. 2014, 55, 292-298.

Khan, S. N.; Lane, J. M. Bone Tissue Engineering: Basic Science and Clinical Concepts. Orthopedic Tissue Engineering; CRC Press, 2004; pp. 177-194.

Oreffo, R. O.; Kusec, V.; Romberg, S.; Triffitt, J. T. Human bone marrow osteoprogenitors express estrogen receptor-alpha and bone morphogenetic proteins 2 and 4 mRNA during osteoblastic differentiation. J. Cell. Biochem. 1999, 75, 382-392.

Frank, O.; Heim, M.; Jakob, M.; Barbero, A.; Schafer, D.; Bendik, I.; Dick, W.; Heberer, M.; Martin, I. Real-time quantitative RT-PCR analysis of human bone marrow stromal cells during osteogenic differentiation in vitro. J. Cell. Biochem. 2002, 85, 737-746.

Miron, R.; Zhang, Y. Osteoinduction: a review of old concepts with new standards. J. Dent. Res. 2012, 91, 736-744.

Rittling, S. R.; Matsumoto, H. N.; Mckee, M. D.; Nanci, A.; An, X. R.; Novick, K. E.; Kowalski, A. J.; Noda, M.; Denhardt, D. T. Mice lacking osteopontin show normal development and bone structure but display altered osteoclast formation in vitro. J. Bone Miner. Res. 1998, 13, 1101-1111.

Chellaiah, M. A.; Kizer, N.; Biswas, R.; Alvarez, U.; Strauss-Schoenberger, J.; Rifas, L.; Rittling, S. R.; Denhardt, D. T.; Hruska, K. A. Osteopontin deficiency produces osteoclast dysfunction due to reduced CD44 surface expression. Mol. Biol. Cell 2003, 14, 173-189.

Bax, D. V.; Rodgers, U. R.; Bilek, M. M.; Weiss, A. S. Cell adhesion to tropoelastin is mediated via the C-terminal GRKRK motif and integrin $\alpha V\beta 3$. J. Biol. Chem. 2009, 284, 28616-28623.

Taddese, S.; Weiss, A. S.; Jahreis, G.; Neubert, R. H.; Schmelzer, C. E. In vitro degradation of human tropoelastin by MMP-12 and the generation of matrikines from domain 24. Matrix Biol. 2009, 28, 84-91.

Getie, M.; Schmelzer, C.; Neubert, R. Characterization of peptides resulting from digestion of human skin elastin with elastase. Proteins 2005, 61, 649-657.

Phillips, J. E.; Petrie, T. A.; Creighton, F. P.; Garcia, A. J. Human mesenchymal stem cell differentiation on self-assembledmonolayers presenting different surface chemistries. Acta Biomater. 2010, 6, 12-20.

Nemir, S.; West, J. L. Synthetic materials in the study of cell response to substrate rigidity. Ann. Biomed. Eng. 2010, 38, 2-20.

Holst, J.; Watson, S.; Lord, M. S.; Eamegdool, S. S.; Bax, D. V.; Nivison-Smith, L. B.; Kondyurin, A.; Ma, L.; Oberhauser, A. F.; Weiss, A. S.; Rasko, J. E. J. Substrate elasticity provides mechanical signals for the expansion of hemopoietic stem and progenitor cells. Nat. Biotechnol. 2010, 28, 1123.

Rowlands, A. S.; George, P. A.; Cooper-White, J. J. Directing osteogenic and myogenic differentiation of MSCs: interplay of stiffness and adhesive ligand presentation. Am. J. Physiol.: Cell Physiol. 2008, 295, C1037-C1044.

Saha, K.; Keung, A. J.; Irwin, E. F.; Li, Y.; Little, L.; Schaffer, D. V.; Healy, K. E. Substrate modulus directs neural stem cell behavior. Biophys. J. 2008, 95, 4426-4438.

Final Official Action received in Japanese Application No. 2019-561848 dated Oct. 11, 2022.

Examination Report received in European Application No. 18 720 665.1 dated Oct. 25, 2022.

Official Action received in Japanese Application No. 2019-561747 dated Sep. 13, 2022.

Examination Report received in Saudi Arabian Application No. 521430991 dated Aug. 18, 2022.

Office Action received in U.S. Appl. No. 16/612,580 dated Sep. 21, 2022.

Office Action received in U.S. Appl. No. 17/401,800 dated Aug. 30, 2022.

International Search Report and Written Opinion received in International Application No. PCT/IB2022/055194 dated Sep. 20, 2022.

International Search Report and Written Opinion received in International Application No. PCT/IB2022/055054 dated Sep. 26, 2022.

Chen et al., "Hydrogelation of the Short Self-Assembling Peptide I3QGK Regulated by Transglutaminase and Use for Rapid Hemostasis", ACS Appl Matter Interfaces, vol. 28, pp. 17833-17841 (2016).

Echalier et al., "Modular bioink for 3D printing of biocompatible hydrogels: sol-gel polymerization of hybrid peptides and polymers", RSC Advances, vol. 7, pp. 12231-12235 (2017).

Holzl et al., "Bioink properties before, during and after 3D printing", Biofabrication, vol. 8, 032002 (2016).

Holz et al., "High-Power 365 nm UV LED Mercury Arc Lamp Replacement for Photochemistry and Chemical Photolithography", ACS Sustainable Chemistry & Engineering, vol. 5, pp. 828-834 (2017).

Lim et al., "New Visible-Light Photoinitiating System for Improved Print Fidelity in Gelatin-Based Bioinks", ACS Biomaterials Science and Engineering, vol. 2, pp. 1752-1762 (2016).

(56)                    References Cited

OTHER PUBLICATIONS

Loo et al., "Bioprinting synthetic self-assembling peptide hydrogels for boimedical applications", Biomedical Materials, vol. 11, No. 1 (2015).

Sekine et al., "Capillary Networks for Bio-Artificial Three-Dimensional Tissues Fabricated Using Cell Sheet Based Tissue Engineering", International Journal of Molecular Sciences, vol. 22, No. 92, pp. 1-12 (2021).

Yan et al., "Advances in portable electrospinning devices for in situ delivery of personalized wound care", Nanoscale, vol. 11, pp. 19166-19178 (2019).

Official Action received in Japanese Application No. 2019-561848 dated Feb. 28, 2023.

Decision of Dismissal of Amendment received in Japanese Application No. 2019-561747 mailed Apr. 18, 2023.

Office Action received in U.S. Appl. No. 17/401,800 mailed Apr. 11, 2022.

Huebsch, N.; Arany, P. R.; Mao, A. S.; Shvartsman, D.; Ali, O. A.; Bencherif, S. A.; Rivera-Feliciano, J.; Mooney, D. J. Harnessing traction-mediated manipulation of the cell/matrix interface to control stem-cell fate. Nat. Mater. 2010, 9, 518.

Kabiri, K.; Omidian, H.; Hashemi, S.; Zohuriaan-Mehr, M. Synthesis of fast-swelling superabsorbent hydrogels: effect of cross-linker type and concentration on porosity and absorption rate. Eur. Polym. J. 2003, 39, 1341-1348.

Hale, B. W.; Goodrich, L. R.; Frisbie, D. D.; McIlwraith, C. W.; Kisiday, J. D. Effect of scaffold dilution on migration of mesenchymal stem cells from fibrin hydrogels. Am. J. Vet. Res. 2012, 73, 313-318.

Cuchiara, M. P.; Allen, A. C.; Chen, T. M.; Miller, J. S.; West, J. L. Multilayer microfluidic PEGDA hydrogels. Biomaterials 2010, 31, 5491-5497.

Cheng, R.; Yan, Y.; Liu, H.; Chen, H.; Pan, G.; Deng, L.; Cui, W. Mechanically enhanced lipo-hydrogel with controlled release of multi-type drugs for bone regeneration. Appl. Mater. Today 2018, 12, 294-308.

Engler, A. J.; Sen, S.; Sweeney, H. L.; Discher, D. E. Matrix elasticity directs stem cell lineage specification. Cell 2006, 126, 677-689.

Sivaraj, K. K.; Adams, R. H. Blood vessel formation and function in bone. Development 2016, 143, 2706-2715.

Kim, S.; Cha, C. Enhanced mechanical and electrical properties of heteroscaled hydrogels infused with aqueous-dispersible hybrid nanofibers. Biofabrication 2020, 12, No. 015020.

Hwang, T. L.; Shaka, A. J., Water Suppression That Works. Excitation Sculpting Using Arbitrary Wave-Forms and Pulsed-Field Gradients. J. Magn. Reson. 1995, 112, (2), 275-279.

Derome, A. E.; Williamson, M. P., Rapid-Pulsing Artifacts in Double-Quantum-Filtered COSY. J. Magn. Reson. 1990, 88, (1), 177-185.

Piotto, M.; Saudek, V.; Sklenář, V., Gradient-Tailored Excitation for Single-Quantum NMR Spectroscopy of Aqueous Solutions. J. Biomol. NMR 1992, 2, (6), 661-665.

Sklenar, V.; Piotto, M.; Leppik, R.; Saudek, V., Gradient-Tailored Water Suppression for 1H-15N HSQC Experiments Optimized to Retain Full Sensitivity. J. Magn. Reson. 1993, 102, (2), 241-245.

Gilbert, D. F.; Erdmann, G.; Zhang, X.; Fritzsche, A.; Demir, K.; Jaedicke, A.; Muehlenberg, K.; Wanker, E. E.; Boutros, M., A novel multiplex cell viability assay for high-throughput RNAi screening. PloS One 2011, 6, (12), e28338.

Arab, "Novel Nanofibrous Peptide Scaffolds for Tissue Regeneration", Dissertation, King Abdullah University of Science and Technology, Thuwal, Saudi Arabia, Apr. 2019.

Ikeno et al., "Effects of self-assembling peptide hydrogel scaffold on bone regeneration with recombinant human bone morphogenetic protein-2"; The International Journal of Oral and Maxillofacial Implants; vol. 28, No. 5, pp. e283-289 (2013).

Liu et al., "Stiffness-mediated mesenchymal stem cell fate decision in 3D-bioprinted hydrogels"; Burns & Trauma, vol. 8, pp. 1-13 (2020).

International Search Report and Written Opinion received in International Application No. PCT/IB2021/057623 mailed Dec. 13, 2021.

Office Action received in Japanese Patent Application No. 2019-561848 mailed Apr. 5, 2022.

Office Action received in Japanese Patent Application No. 2019-561747 mailed Mar. 15, 2022.

Notice of Allowance received in Korean Application No. 10-2019-7036377 dated Apr. 6, 2022.

Search Report and Written Opinion received in PCT Application No. PCT/IB2021/060795.

Ali et al., "A Non-Canonical NRPS Is Involved in the Synthesis of Fungisporin and Related Hydrophobic Cyclic Tetrapeptides in Penicillium chrysogenum", PLOS ONE, vol. 9, Issue 6, pp. 1-10 (2014).

Alrashoudi et al., "Fabrication of a Lateral Flow Assay for Rapid In-Field Detection of COVID-19 Antibodies Using Additive Manufacturing Printing Technologies", International Journal of Bioprinting, vol. 7, Issue 4, pp. 76-84 (2021).

Farrera-Soler et al, "Identification of immunodominant linear epitodes from SARS-CoV-2 patient plasma", PLOS ONE, pp. 1-15 (2020).

Saatci, Newly developed methods for SARS-CoV-2 detection [SARS-CoV-2 saptanmasinda yeni gelistririlen tani yontemleri], Turk J. Biochem., 45 (5), pp. 465-474 (2020).

Vasco et al., "Macrocyclization of Peptide Side Chains by the Ugi Reaction: Achieving Peptide Folding and Exocyclic N-Functionalization in One Shot", Journal of Organic Chemistry, 80, pp. 6697-6707 (2015).

Xiang et al., "A novel double antibody sandwich-lateral flow immunoassay for the rapid and simple detection of hepatitis C virus", International Journal of Molecular Medicine, 30, pp. 1041-1047 (2012).

Examination Report received in European Patent Application No. 18 718 922.0 dated May 20, 2022.

Written Opinion received in Singapore Application No. 10202112455P dated Jul. 11, 2023.

Office Action received in Japanese Application No. 2019-561848 dated May 22, 2023.

Notice of Final Rejection received in Korean Application No. 10-2019-7036272 dated May 25, 2023.

European Search Report received in European Application No. 23159765.9 dated Jun. 22, 2023.

Ali et al., "A Non-Canonical NRPS Is Involved in the Synthesis of Fungisporin and Related Hydrophobic Cyclic Tetrapeptides in Penicillium chrysogenum", PLOS ONE; vol. 9, Issue 6, e98212 (2014).

Pubchem CID: 93078 "L-Aspartyl-L_phenylalanine" (2005).

Vasco et al., "Macrocyclization of Peptide Side Chains by the Ugi Reaction: Achieving Peptide Folding and Exocyclic N-Functionalization in One Shot", The Journal of Organic Chemistry, 80, pp. 6697-6707 (2015).

Zhang et al., "Catechol functionalized hyperbranched polymers as biomedical materials", Polymers in Polymer Science, vol. 78, pp. 47-55 (2018).

Examination Report received in Saudi Arabian Application No. 523442624 mailed Sep. 28, 2023.

International Search Report and Written Opinion received in PCT Application No. PCT/IB2023/056328 mailed Oct. 13, 2023.

Liu et al., "Stiffness-mediated mesenchymal stem cell fate decision in 3D-bioprinted hydrogels", Burns & Trauma, vol. 8 (2020).

Written Opinion received in Singapore Application No. 1020112455P dated Mar. 27, 2024.

Examination Report received in Saudi Arabian Application No. 523442596 dated Mar. 31, 2024.

Non-Final Office Action received in U.S. Appl. No. 18/021,645 dated Apr. 1, 2024.

Pubchem CID: 97078 "L-Aspartyl-L-phenylalanine".

Extended European Search Report received in European Application No. 21857887.0 dated Sep. 23, 2024.

Arab et al., "Evaluation of peptide nanogels for accelerated wound healing in normal micropigs", Frontiers in Nanoscience and Nanotechnology, vol. 4, pp. 1-9 (2018).

Arab, "Novel Nanofibrous Peptide Scaffolds for Tissue Regeneration", PhD Thesis, XP055901075 (2019).

(56)                    References Cited

OTHER PUBLICATIONS

Ceylan et al., "Mussel Inspired Dynamic Cross-Linking of Self-Healing Peptide Nanofiber Network", Advanced Functional Materials, vol. 23, pp. 2081-2090 (2013).

Chakraborty et al., "A Self-Healing, All-Organic, Conducting, Composite Peptide Hydrogel as Pressure Sensor and Electrogenic Cell Soft Substrate", ACS Nano, vol. 13, pp. 163-175 (2019).

Cringoli et al., "Bioadhesive supramolecular hydrogel from unprotected short D,L-peptides with Phe-Phe and Leu-Asp-Val motifs", Royal Society of Chemistry, vol. 56, pp. 3015-2018 (2020).

Dooley et al., "Selective Ligands for the u, S, and x Opiod Receptors Identified from a Single Mixture Based Tetrapeptide Positional Scanning Combinatorial Library", The Journal of Biological Chemistry, vol. 278, No. 30, pp. 18848-18856 (1998).

Duncan et al., "Short Peptides in Minimalistic Biocatalyst Design", Biocatalysis, No. 1, pp. 67-81 (2015).

Extended European Search Report received in European Application No. 21863813.8 dated Sep. 9, 2024.

Extended European Search Report received in European Application No. 21857886.2 dated Jul. 29, 2024.

Extended European Search Report received in European Application No. 21882283.1 dated Sep. 16, 2024.

Feng et al., "Development of a Potent Thrombin Receptor Ligand", J. Med. Chem., vol. 38, pp. 4125-4130 (1995).

Final Office Action received in U.S. Appl. No. 17/401,434 dated Jul. 17, 2024.

Lee et al., "Enzyme-crosslinked gene-activated matrix for the induction of mesenchymal stem cells in osteochondral tissue regeneration", Acta Biomaterialia, vol. 63, pp. 210-226 (2017).

Li et al., "Peptide-Templated Synthesis of TiO2, Nanofibers with Tunable Photocatalytic Activity", Chem. Eur. J., vol. 24, pp. 18123-18129 (2018).

Liu et al., "Stiffness-mediated mesenchymal stem cell fate decision in 3D-bioprinted hydrogels", Burns & Trauma, vol. 8, tkaa029 (2020).

Nakatsu et al., "An Optimized Three-Dimensional In Vitro Model for the Analysis of Angiogenesis", Methods in Enzymology, vol. 443, pp. 65-82 (2008).

Ramirez-Calderon et al., "Delivery of Endothelial Cell-Laden Microgel Elicits Angiogenesis in Self-Assembling Ultrashort Peptide Hydrogels in Vitro", ACS Appl. Mater. Interfaces, vol. 13, pp. 29281-29292 (2021).

Restu et al., "Short Oligopeptides for Biocompatible and Biodegradeable Supremolecular Hydrogels", Langmuir, vol. 34, pp. 8065-8074 (2018).

Notification of the Substantive Examination Report received in Saudi Arabian Application No. 523440449 dated Aug. 27, 2024.

Shin et al., "The position of lysine controls the catechol-mediated surface adhesion and cohesion in underwater mussel adhesion", Journal of Colloid and Interface science, vol. 563, pp. 168-176 (2020).

Thota et al. "Molecular insights into the self-assembly of short amphiphilic peptides FmDn and FmKn", RSC Adv., vol. 4, pp. 60/41-60/48 (2014).

Written Opinion received in Singaporean Application No. 10202112428Y dated Sep. 18, 2024.

Zhang et al., "Compatability of Neural Stem Cells with Functionalized Self-assembling Peptide Scaffold In vitro", Biotechnology and Bioprocess Engineering, vol. 15, pp. 545-551 (2010).

* cited by examiner

PEPTIDE COMPOUND WITH REPETITIVE SEQUENCES

CROSS-REFERENCE TO RELATED APPLICATIONS

This application claims benefit of priority of U.S. Provisional Patent Application No. 63/067,913 entitled, "PEPTIDE COMPOUND WITH REPETITIVE SEQUENCES" filed Aug. 20, 2020. The entire contents and disclosures of these patent applications are incorporated herein by reference in their entirety.

REFERENCE TO A "SEQUENCE LISTING"

The present application includes a Sequence Listing which has been submitted electronically in an ASCII text format. This Sequence Listing is named 114147-23797US01_sequence listing.TXT was created on Apr. 19, 2021, is 12,526 bytes in size and is hereby incorporated by reference in its entirety.

BACKGROUND

Field of the Invention

The present disclosure relates to peptides capable of forming a gel. The present disclosure further relates to a gel comprising a peptide in accordance with the present disclosure, to a method of preparing such gel and to the use of such gel.

Background of the Invention

The use of scaffolds that resemble the extracellular matrix is of utmost importance in fields such as tissue engineering and regenerative medicine. Typically, natural bioinks with application in 3D bioprinting, such as gelatin, collagen, and hyaluronic acid, are obtained from non-human sources[1]. These natural-based materials show better biocompatibility than synthetic polymer inks as they contain inherent biofunctional cues essential for cell attachment and growth[2]. However, due to their weak mechanical strength and inability to maintain good shape fidelity, these bioinks are usually chemically modified with acrylate groups to induce polymerization using UV light[3]. Prolonged cumulative UV exposure of cells during printing and the presence of photoinitiators dramatically reduce the biocompatibility of these bioinks[4]. Additionally, there are other concerns of using these bioinks for clinical applications, such as batch-to-batch variations and immunogenicity[5].

Due to the limitations of the naturally derived scaffolds, there exists a need for a new class of biomaterials.

SUMMARY

It is therefore desirable to provide a biocompatible compound that is capable of forming a hydrogel that meets at least some of the above requirements to a higher extent than currently available hydrogels and that is not restricted by the above mentioned limitations.

According to a first broad aspect of the present disclosure, an ultrashort peptide sequences containing repetitive sequences capable of forming low molecular weight nanogels by self-assembly, wherein the ultrashort peptides are amphiphilic, is provided. The ultrashort peptides are able to self-assemble into supramolecular structures, having a composition of amino acids A, B, X, such as $$A_nB_mX \text{ or } B_mA_nX \text{ or } XA_nB_m \text{ or } XB_mA_n$$

wherein the total number of amino acids of the ultrashort peptide does not exceed 7 amino acids; wherein A are comprised of aliphatic, i.e. non-aromatic, hydrophobic amino acids, selected from the group of aliphatic amino acids, such as isoleucine and leucine, with n being an integer being selected from 0-5; wherein B are comprised of one aromatic amino acid, such as tyrosine, tryptophan, or phenylalanine, preferably the hydrophobic amino acid phenylalanine, or comprised of a peptidomimetic amino acid that is the aliphatic counterpart of the aromatic amino acid, such as cyclohexylalanine, which is the counterpart of amino acid phenylalanine with m being an integer being selected from 0-3; wherein X is comprised of a polar amino acid, selected from the group of aspartic acid, glutamic acid, lysine, arginine, histidine, cysteine, serine, threonine, asparagine, and glutamine; and wherein when m=1, n>2.

According to a second broad aspect of the present disclosure, a hydrogel or organogel comprising the peptides is provided according to the present disclosure.

According to a third broad aspect of the present disclosure, a method of preparing a hydrogel or organogel, the method comprising dissolving a peptide is provided in an aqueous solution or an organic solution, respectively.

The objects of the present disclosure are also solved by a surgical implant, or stent, the surgical implant or stent comprising a peptide and or peptoid scaffold, wherein the peptide and/or peptoid scaffold is formed by a hydrogel according to the present disclosure.

The objects of the present disclosure are also solved by a pharmaceutical and/or cosmetic composition and/or a biomedical device and/or electronic device comprising the amphiphilic peptide and/or peptoid according to the present disclosure.

In one embodiment, the pharmaceutical and/or cosmetic composition and/or the biomedical device, and/or the electronic devices as defined above, further comprises a pharmaceutically active compound.

In one embodiment, the pharmaceutical and/or cosmetic composition as defined above, further comprises a pharmaceutically acceptable carrier.

The objects of the present disclosure are also solved by a kit of parts, the kit comprising a first container with an amphiphilic peptide and/or peptoid according to the present disclosure and a second container with an aqueous solution.

In one embodiment, the aqueous solution of the second container further comprises a pharmaceutically active compound. In one embodiment, the first container with an amphiphilic peptide and/or peptoid further comprises a pharmaceutically active compound.

The objects of the present disclosure are solved by a method of tissue regeneration comprising the steps: providing a hydrogel as defined above, exposing the hydrogel to cells which are to form regenerated tissue, allowing the cells to grow on the hydrogel.

In one embodiment, the method as defined above is performed in-vitro or in-vivo.

In one embodiment, the method as defined above is performed in vivo, wherein, in step a), the hydrogel is provided at a place in a body where tissue regeneration is intended.

In one embodiment, the step a) is performed by injecting the hydrogel at a place in the body where tissue regeneration is intended.

An aspect of the invention provides a surgical implant or stent. The surgical implant or stent includes a peptide and/or peptoid scaffold. The peptide and/or peptoid scaffold is defined by a hydrogel of the present disclosure.

An aspect the invention provides a pharmaceutical and/or cosmetic composition. The pharmaceutical and/or cosmetic composition includes the amphiphilic peptide and/or peptoid according to the present disclosure. The pharmaceutical and/or cosmetic composition may comprise a pharmaceutically active compound. The pharmaceutical and/or cosmetic composition may comprise a pharmaceutically acceptable carrier.

An aspect the invention provides a kit of parts. The kit includes a first container and a second container. The first container includes a peptide and/or peptoid according to the first aspect. The second container includes an aqueous solution. The aqueous solution of the second container may further comprise a pharmaceutically active compound. The first container with an amphiphilic peptide and/or peptoid may further comprise a pharmaceutically active compound.

Other aspects and features of the present disclosure will become apparent to those skilled in the art upon review of the following description of specific embodiments of the invention in conjunction with the accompanying figures.

BRIEF DESCRIPTION OF THE DRAWINGS

The accompanying drawings, which are incorporated herein and constitute part of this specification, illustrate exemplary embodiments of the invention, and, together with the general description given above and the detailed description given below, serve to explain the features of the invention.

DETAILED DESCRIPTION OF THE INVENTION

Definitions

Figure 1:
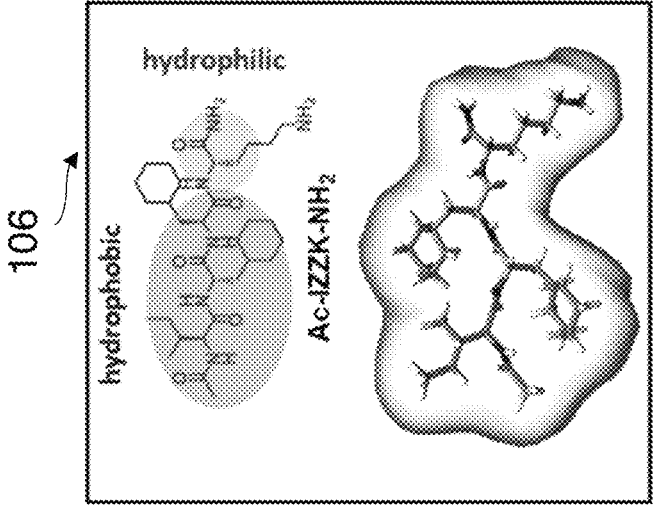
FIG. 1 is a graph showing the molecular structure of IIFK (SEQ ID NO: 1), IIZK (SEQ ID NO: 9) and IZZK (SEQ ID NO: 25) according to an embodiment of the present disclosure.
Figure 1:
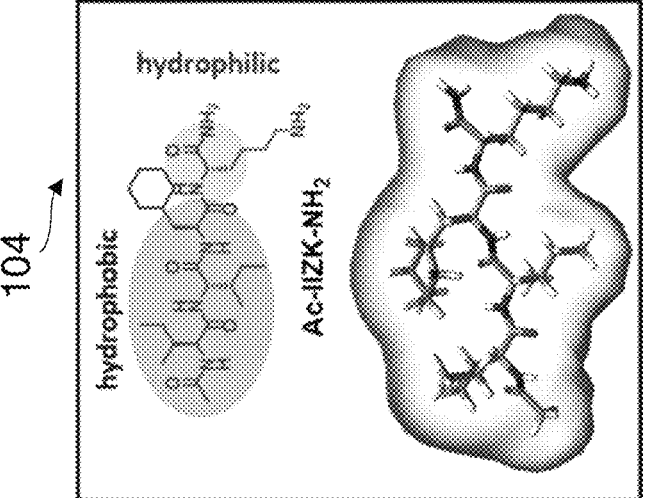
Figure 1:
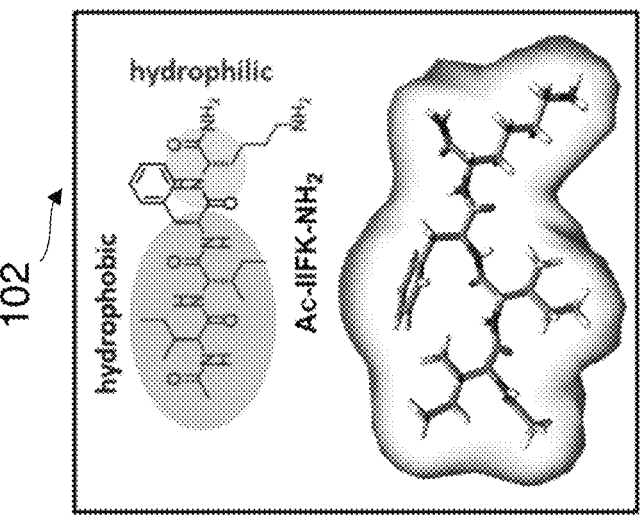

Where the definition of terms departs from the commonly used meaning of the term, applicant intends to utilize the definitions provided below, unless specifically indicated.

Unless defined otherwise, all technical and scientific terms used herein have the same meaning as is commonly understood to which the claimed subject matter belongs. In the event that there is a plurality of definitions for terms herein, those in this section prevail. All patents, patent applications, publications and published nucleotide and amino acid sequences (e.g., sequences available in GenBank or other databases) referred to herein are incorporated by reference. Where reference is made to a URL or other such identifier or address, it is understood that such identifiers can change and particular information on the internet can come and go, but equivalent information can be found by searching the internet. Reference thereto evidences the availability and public dissemination of such information.

It is to be understood that the foregoing general description and the following detailed description are exemplary and explanatory only and are not restrictive of any subject matter claimed. In this application, the use of the singular includes the plural unless specifically stated otherwise. It must be noted that, as used in the specification and the appended claims, the singular forms "a," "an" and "the" include plural referents unless the context clearly dictates otherwise. In this application, the use of "or" means "and/or" unless stated otherwise. Furthermore, use of the term "including" as well as other forms, such as "include", "includes," and "included," is not limiting.

For purposes of the present disclosure, the term "comprising", the term "having", the term "including," and variations of these words are intended to be open-ended and mean that there may be additional elements other than the listed elements.

For purposes of the present disclosure, directional terms such as "top," "bottom," "upper," "lower," "above," "below," "left," "right," "horizontal," "vertical," "up," "down," etc., are used merely for convenience in describing the various embodiments of the present disclosure. The embodiments of the present disclosure may be oriented in various ways. For example, the diagrams, apparatuses, etc., shown in the drawing figures may be flipped over, rotated by 90° in any direction, reversed, etc.

For purposes of the present disclosure, a value or property is "based" on a particular value, property, the satisfaction of a condition, or other factor, if that value is derived by performing a mathematical calculation or logical decision using that value, property or other factor.

For purposes of the present disclosure, it should be noted that to provide a more concise description, some of the quantitative expressions given herein are not qualified with the term "about." It is understood that whether the term "about" is used explicitly or not, every quantity given herein is meant to refer to the actual given value, and it is also meant to refer to the approximation to such given value that would reasonably be inferred based on the ordinary skill in the art, including approximations due to the experimental and/or measurement conditions for such given value.

For purposes of the present disclosure, the term "amphiphilic" or "amphiphilicity" refers to being a compound consisting of molecules having a water-soluble group at one end and a water-insoluble group at the other end.

The term "aliphatic" means, unless otherwise stated, a straight or branched hydrocarbon chain, which may be saturated or mono- or poly-unsaturated and include heteroatoms. An unsaturated aliphatic group contains one or more double and/or triple bonds (alkenyl or alkynyl moieties). The branches of the hydrocarbon chain may include linear chains as well as non-aromatic cyclic elements. The hydrocarbon chain, which may, unless otherwise stated, be of any length, and contain any number of branches. Typically, the hydrocarbon (main) chain includes 1 to 5, to 10, to 15 or to 20 carbon atoms. Examples of alkenyl radicals are straight-chain or branched hydrocarbon radicals which contain one or more double bonds. Alkenyl radicals generally contain about two to about twenty carbon atoms and one or more, for instance two, double bonds, such as about two to about ten carbon atoms, and one double bond. Alkynyl radicals normally contain about two to about twenty carbon atoms and one or more, for example two, triple bonds, preferably such as two to ten carbon atoms, and one triple bond. Examples of alkynyl radicals are straight-chain or branched hydrocarbon radicals which contain one or more triple bonds. Examples of alkyl groups are methyl, ethyl, propyl, butyl, pentyl, hexyl, heptyl, octyl, nonyl, decyl, the n isomers of these radicals, isopropyl, isobutyl, isopentyl, sec-butyl, tert-butyl, neopentyl, 3,3 dimethylbutyl. Both the main chain as well as the branches may furthermore contain heteroatoms as for instance N, O, S, Se or Si or carbon atoms may be replaced by these heteroatoms.

The term "heteroatom" as used herein means an atom of any element other than carbon or hydrogen.

For purposes of the present disclosure, the term "gel", "nanogel" "hydrogel" and "organogel" are used interchangeably. These terms refer to a is a network of polymer chains, entrapping water or other aqueous solutions, such as physiological buffers, of over 99% by weight. In an embodiment of the present disclosure, the polymer chains may be a peptide with repetitive sequences. If the self-assembly of the ultrashort peptides occurs in aqueous solution, hydrogels are formed. If organic solvents are used, organogels are formed.

For purposes of the present disclosure, the term "ultra-short peptide" refers to a sequence containing 3-7 amino acids. The peptides according an aspect of the present disclosure are also particularly useful for formulating aqueous or other solvent compositions, herein also sometimes referred to as "inks" or "bioinks", which may be used as inks for printing structures and as bioinks for printing cellular or tissue structures, in particular 3D structures. Such printed structures make use of the gelation properties of the peptides according to features of the present disclosure.

For purposes of the present disclosure, the term "bioinks" as used herein means materials used to produce engineered/artificial live tissue, cellular grafts and organ substitutes (organoids) using 3D printing. In the present disclosure, these bioinks are mostly composed of hydrogel or organogel with cellular components embedded.

For purposes of the present disclosure, the term "scaffolds" as used herein means the supramolecular network structures made from self-assembling ultra-short peptide or other polymer materials in the bioinks that provide support for the cellular components.

For purposes of the present disclosure, the term "printability" refers to the suitability of peptide for 3D printing. In particular, it refers to the suitable speed of self-assembly at certain concentration, and viscosity. The speed of forming gel and viscosity need to be high enough so that a structure with certain height can be printed without collapsing. On the other hand, the speed and viscosity need to be low enough so that the peptide will not clog the nozzle of bioprinters.

For purposes of the present disclosure, the terms "implant" and "implantation" are used interchangeably. These terms refer to uses and applications of/for surgical or arthroscopic implantation of a hydrogel containing device into a human or animal, e.g. mammalian, body or limb.

For purposes of the present disclosure, the term "biocompatible" (which also can be referred to as "tissue compatible"), as used herein, refers to the property of a hydrogel that produces little if any adverse biological response when used in vivo.

Description

Ultrashort self-assembling peptides are composed of 3-7 naturally occurring amino acids in length. Due to their amphiphilic nature, they tend to self-assemble at physiological conditions to form hydrogels that mimic the structure of the extracellular matrix. These characteristics make ultrashort peptides a suitable biomaterial for tissue engineering[6, 7]. The present disclosure relates to peptides capable of forming a gel by self-assembly and to their use(s), e.g., particularly in tissue engineering and bioprinting. The present disclosure furthermore relates to a gel comprising a peptide in accordance with the present disclosure, to a method of preparing such gel in the presence of solvents and to the use(s) of such gel. In one embodiment, such gel is a hydrogel. The present disclosure furthermore relates a scaffold that can support the growth and maintenance of cells in a 3-dimensional (3D) environment. As such, this scaffold is able to be used for tissue engineering related to applications in regenerative medicine. The 3D cellular scaffold can be used to establish 3D disease models, for example to study cancer or degenerative and particular neurodegenerative diseases. The scaffold can also be used in the presence of cells and tissues for diagnostic and drug screening purposes. The peptide 3D scaffold exerts strong and stably sustainable mechanical properties which enable the use of the peptides as inks for printing and particularly bioprinting purposes. During the printing process, the peptide solution may be used in combination with cells, drugs, nanoparticles, therapeutic agents, nucleic acids and else in order to support the printing applications. The present disclosure relates in addition to a wound dressing or wound healing agent comprising a gel according to the present disclosure and to a surgical implant or stent comprising a peptide scaffold formed by a gel according to the present disclosure. Moreover, the present disclosure also relates to a pharmaceutical and/or cosmetic composition, to a biomedical device or an electronic device comprising the peptide according to the present disclosure. Furthermore, the present disclosure relates to a kit comprising a first container containing a peptide according to the present disclosure, and a second container containing an aqueous or organic solution. Moreover, the present disclosure relates to a method of tissue regeneration, using a gel in accordance with the present disclosure. Furthermore, the present disclosure also relates to a method of printing using the peptide(s) and/or the gel(s) according to the present disclosure. Furthermore, the present disclosure relates to a method of treatment of a wound and/or for wound healing involving the use of a gel and/or peptide(s) according to the present disclosure.

According to a first broad aspect, the present disclosure provides ultrashort peptide sequences containing repetitive sequences capable of forming low molecular weight nanogels by self-assembly, wherein the ultrashort peptides are amphiphilic. The ultrashort peptides are able to self-assemble into supramolecular structures, having a composition of amino acids A, B, X, such as $$A_nB_mX \text{ or } B_mA_nX \text{ or } XA_nB_m \text{ or } XB_mA_n$$

wherein the total number of amino acids of the ultrashort peptide does not exceed 7 amino acids;

wherein A are comprised of aliphatic, i.e. non-aromatic, hydrophobic amino acids, selected from the group of aliphatic amino acids, such as isoleucine and leucine, with n being an integer being selected from 0-5;

wherein B are comprised of one aromatic amino acid, such as tyrosine, tryptophan, or phenylalanine, preferably the hydrophobic amino acid phenylalanine, or comprised of a peptidomimetic amino acid that is the aliphatic counterpart of the aromatic amino acid, such as cyclohexylalanine, which is the counterpart of amino acid phenylalanine with m being an integer being selected from 0-3;

wherein X is comprised of a polar amino acid, selected from the group of aspartic acid, glutamic acid, lysine, arginine, histidine, cysteine, serine, threonine, asparagine, and glutamine; and wherein when m=1, n>2.

In a preferred embodiment, the present disclosure provides ultrashort peptide sequences containing repetitive sequences capable of forming low molecular weight nanogels by self-assembly, wherein the ultrashort peptides are amphiphilic. The ultrashort peptides are able to self-assemble into supramolecular structures, having a composition of amino acids A, B, X, such as $$A_nB_mX \text{ or } B_mA_nX \text{ or } XA_nB_m \text{ or } XB_mA_n$$

wherein the total number of amino acids of the ultrashort peptide does not exceed 7 amino acids;

wherein A are comprised of aliphatic, i.e. non-aromatic, hydrophobic amino acids, selected from the group of aliphatic amino acids, such as isoleucine and leucine, with n being an integer being selected from 2-5;

wherein B are comprised of one aromatic amino acid, such as tyrosine, tryptophan, or phenylalanine, preferably the hydrophobic amino acid phenylalanine, or comprised of a peptidomimetic amino acid that is the aliphatic counterpart of the aromatic amino acid, such as cyclohexylalanine, which is the counterpart of amino acid phenylalanine with m being an integer being selected from 1 and 2; and wherein X is comprised of a polar amino acid, selected from the group of aspartic acid, glutamic acid, lysine, arginine, histidine, cysteine, serine, threonine, asparagine, and glutamine.

The amphiphilic peptide sequences containing repetitive sequences provided in the present disclosure show true supergelating properties, forming low molecular weight nanogels by entrapping water or other aqueous solutions, such as physiological buffers, of over 99% by weight. Therefore, hydrogels can be generated. These amphiphilic peptides have an innate propensity to self-assemble to 3D fibrous networks in form of hydrogels. These gels can also be termed nanogels, because the diameter of the single fibers of the gel's fiber network have nanometer diameters. These peptide compounds are self-driven by non-covalent interactions to form soft solid material. Based on the nature of the peptides involved, generally composed of natural amino acids, these soft materials can easily be used for biomedical applications, for tissue engineering, but also for technical applications.

It should be appreciated that the novel peptides have newly introduced aromatic amino acids in the hydrophobic part of the amphiphilic peptide structure. This is a significant improvement over prior peptides which focus solely on peptides containing aliphatic amino acids. The inclusion of aromatic amino acids is crucial for improving the self-assembly process over prior peptide configurations such as disclosed in WO 2011/123061 A1 which is incorporated herein by reference.

It should be appreciated that the novel peptides have do not focus on the orientation of the hydrophobic part of the peptide compound as being limited to the N-terminus and the polar hydrophilic part limited to the C-terminus as is the case in prior peptides. The present amphiphilic peptides work well with having both orientations, as of N-terminus-hydrophobic part-hydrophilic part-C-terminus as well as N-terminus-hydrophili part-hydrophobi part-C-terminus.

The novel peptides offer the possibility to exchange the aromatic residue to its non-aromatic counterpart, such as using cyclohexylalanine instead of aromatic phenylalanine.

Non-natural amino acids with a cyclic aliphatic ring structure, i.e. the non-aromatic counterparts, such as cyclohexylalanine besides others.

In one embodiment, the peptides are D-peptides.

In a preferred embodiment, the peptides are L-peptides.

In some embodiment, the self-assembly of the ultrashort peptides occurs in aqueous solution forming hydrogels or in organic solvents forming organogels.

In one embodiment, the peptide consists of a sequence selected from

```
                              (SEQ ID NO: 1)
IIFK (SEQ ID NO: 2)
IIFR (SEQ ID NO: 3)
IIFD (SEQ ID NO: 4)
IIFE (SEQ ID NO: 5)
LLFK (SEQ ID NO: 6)
LLFR (SEQ ID NO: 7)
LLFD (SEQ ID NO: 8)
LLFE (SEQ ID NO: 9)
IIZK (SEQ ID NO: 10)
IIZR (SEQ ID NO: 11)
IIZD (SEQ ID NO: 12)
IIZE (SEQ ID NO: 13)
LLZK (SEQ ID NO: 14)
LLZR (SEQ ID NO: 15)
LLZD (SEQ ID NO: 16)
LLZE (SEQ ID NO: 17)
IFFK (SEQ ID NO: 18)
IFFR (SEQ ID NO: 19)
IFFD (SEQ ID NO: 20)
IFFE (SEQ ID NO: 21)
LFFK (SEQ ID NO: 22)
LFFR
```

-continued
```
                              (SEQ ID NO: 23)
LFFD (SEQ ID NO: 24)
LFFE (SEQ ID NO: 25)
IZZK (SEQ ID NO: 26)
IZZR (SEQ ID NO: 27)
IZZD (SEQ ID NO: 28)
IZZE (SEQ ID NO: 29)
LZZK (SEQ ID NO: 30)
LZZR (SEQ ID NO: 31)
LZZD (SEQ ID NO: 32)
LZZE (SEQ ID NO: 33)
FFIK (SEQ ID NO: 34)
ZZIR (SEQ ID NO: 35)
FFID (SEQ ID NO: 36)
FFIE (SEQ ID NO: 37)
FFLK (SEQ ID NO: 38)
FFLR (SEQ ID NO: 39)
FFLD (SEQ ID NO: 40)
FFLE (SEQ ID NO: 41)
ZZIK (SEQ ID NO: 42)
ZZIR (SEQ ID NO: 43)
ZZID (SEQ ID NO: 44)
ZZIE (SEQ ID NO: 45)
ZZLK (SEQ ID NO: 46)
ZZLR (SEQ ID NO: 47)
ZZLD (SEQ ID NO: 48)
ZZLE (SEQ ID NO: 49)
FIIK
```

11
-continued

FIIR (SEQ ID NO: 50)

FIID (SEQ ID NO: 51)

FIIE (SEQ ID NO: 52)

FLLK (SEQ ID NO: 53)

FLLR (SEQ ID NO: 54)

FLLD (SEQ ID NO: 55)

FLLE (SEQ ID NO: 56)

ZIIK (SEQ ID NO: 57)

ZIIR (SEQ ID NO: 58)

ZIID (SEQ ID NO: 59)

ZIIE (SEQ ID NO: 60)

ZLLK (SEQ ID NO: 61)

ZLLR (SEQ ID NO: 62)

ZLLD (SEQ ID NO: 63)

ZLLE (SEQ ID NO: 64)

wherein I is isoleucine, L is leucine, F is phenylalanine, K is lysine, R is arginine, D is aspartic acid, E is glutamic acid, Z is cyclohexylalanine, wherein each of the sequences may be protected or unprotected at the N-terminus, preferably acetylated or non-acetylated, and may be amidated or non-amidated at the C-terminus.

In one embodiment, the N-terminal protecting group is a peptidomimetic molecule, including natural and synthetic amino acid derivatives, wherein the N-terminus of the peptidomimetic molecule may be modified with a functional group selected from the group consisting of carboxylic acid, amide, alcohol, aldehyde, amine, imine, nitrile, an urea analog, phosphate, carbonate, sulfate, nitrate, maleimide, vinyl sulfone, azide, alkyne, alkene, carbohydrate, imide, peroxide, ester, aryl, ketone, sulphite, nitrite, phosphonate, and silane.

In one embodiment, the C-terminal protecting group is selected from the group of small molecules, functional groups and linkers.

In one embodiment, the C-terminal protecting group is selected from functional groups, such as polar or non-polar functional groups, such as (but not limited to)

—COOH, —COOR, —COR, —CONBR or —CONRR' with R and R' being selected from the group consisting of H, unsubstituted or substituted alkyls, and unsubstituted or substituted aryls,

—NH2, —OH, —SH, —CHO, maleimide, imidoester, carbodiimide ester, isocyanate;

small molecules, such as (but not limited to) sugars, alcohols, hydroxy acids, amino acids, vitamins, biotin;

linkers terminating in a polar functional group, such as (but not limited to) ethylenediamine, PEG, carbodiimide ester, imidoester;

linkers coupled to small molecules or vitamins, such as biotin, sugars, hydroxy acids.

In one preferred embodiment, the peptide is selected from IIFK (SEQ ID NO: 1) (Ile-Ile-Phe-Lys-NH$_2$) 102, IIZK (SEQ ID NO: 9) (Ac-Ile-Ile-Cha-Lys-NH$_2$) 104 and IZZK (SEQ ID NO: 25) (Ac-Ile-Cha-Cha-Lys-NH$_2$) 106. The molecular structure of IIFK (SEQ ID NO: 1), IIZK (SEQ ID NO: 9) and IZZK (SEQ ID NO: 25) are illustrated in FIG. 1.

Figure 2:
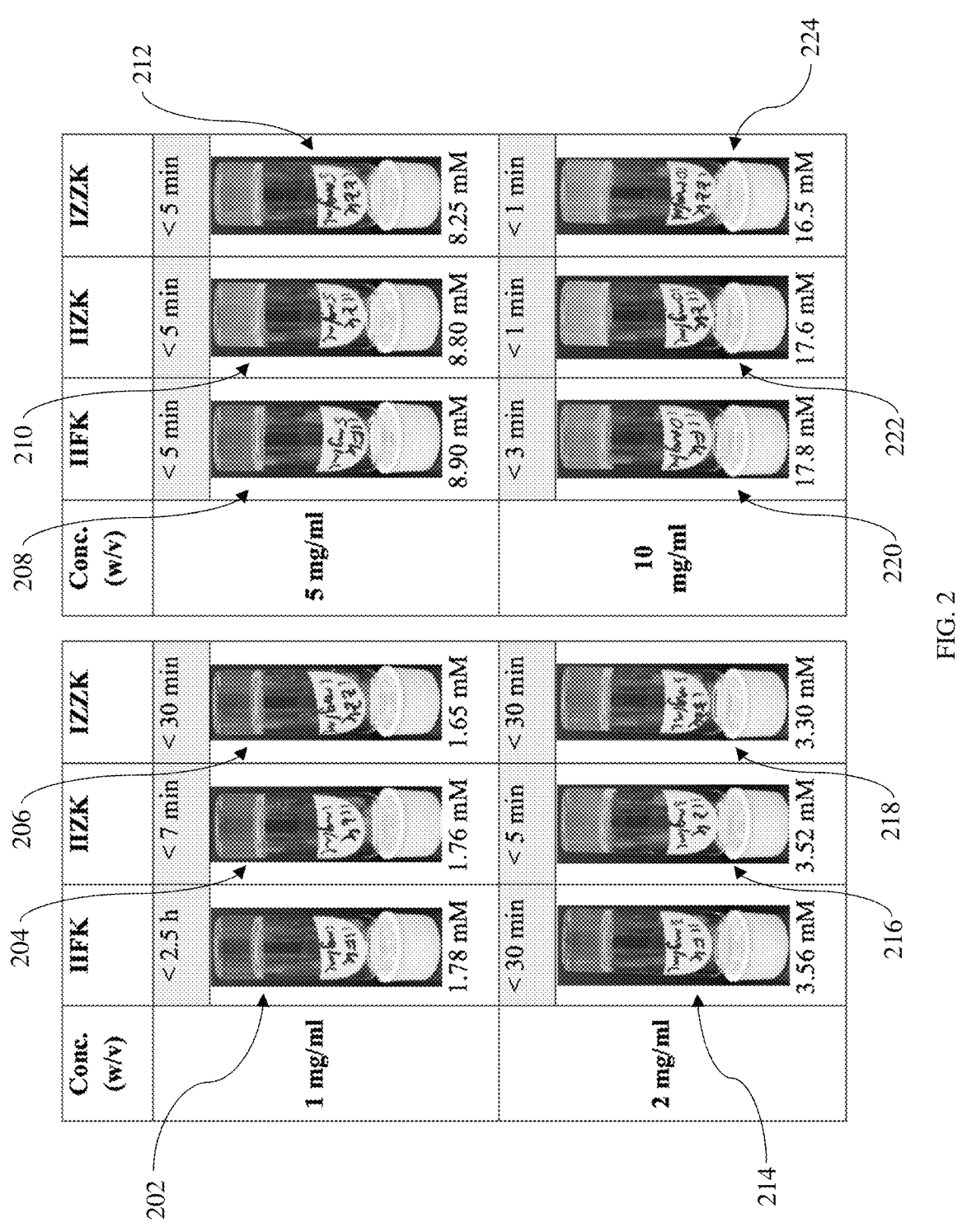
FIG. 2 is a graph showing the time required for IIFK (SEQ ID NO: 1), IIZK (SEQ ID NO: 9) and IZZK (SEQ ID NO: 25) to form a gel at different concentration according to an embodiment of the present disclosure.

The results show that all three peptides are able to form transparent hydrogels at 0.1% (1 mg/ml) w/v in 1×PBS buffer with the shortest gelation time of 7 min for IIZK (SEQ ID NO: 9) (FIG. 2). FIG. 2 shows that at the concentration of 1 mg/ml, the gelation time of IIFK (SEQ ID NO: 1) is less than 2.5 h (202), IIZK (SEQ ID NO: 9) is less than 7 min (204) and IZZK (SEQ ID NO: 25) is less than 30 min (206). At the concentration of 2 mg/ml, the gelation time of IIFK (SEQ ID NO: 1) is less than 30 min (214), IIZK (SEQ ID NO: 9) is less than 5 min (216) and IZZK (SEQ ID NO: 25) is less than 30 min (2) 18. At the concentration of 5 mg/ml, the gelation times of IIFK (SEQ ID NO: 1) (208), IIZK (SEQ ID NO: 9) (210) and IZZK (SEQ ID NO: 25) (212) are all less than 5 min. At the concentration of 10 mg/ml, the gelation time of IIFK (SEQ ID NO: 1) is less than 3 min (202), IIZK (SEQ ID NO: 9) is less than 1 min (222) and IZZK (SEQ ID NO: 25) is less than 1 min (224). Remarkably, their minimum gelation concentrations (MGCs) are one of the lowest gelation concentrations for non-enzymatic supramolecular hydrogel at physiological conditions[8-11]. These initial findings indicated that the three peptides could be promising candidates as bioinks.

In one embodiment, the peptide is dissolved at a concentration from 0.01 µg/ml to 100 mg/ml, preferably at a concentration from 1 mg/ml to 50 mg/ml, more preferably at a concentration from about 1 mg/ml to about 20 mg/ml.

The nature of the self-assembling process depends solely on the sequence information. It was reported previously that an amphiphilic peptide could self-assemble if it passes a minimal hydrophobicity threshold.[12] The presence of an aromatic sidechain for x-stacking and an aromatic interaction can reduce the lag phase of aggregation kinetics, though it is not crucial for forming long-range fiber network which is needed for hydrogelation.[13, 14] FIG. 2 shows that the self-assembly rate of IIFK (SEQ ID NO: 1) is slower than the Cha-containing peptides (IIZK (SEQ ID NO: 9) and IZZK (SEQ ID NO: 25)), as it takes longer for IIFK (SEQ ID NO: 1) to assemble into gel at the concentrations of 1 mg/ml and 10 mg/ml, compared to IIZK (SEQ ID NO: 9) and IZZK (SEQ ID NO: 25). On the other hand, IZZK (SEQ ID NO: 25), which is more hydrophobic than IIZK (SEQ ID NO: 9) form a gel slower than IIZK (SEQ ID NO: 9) (FIG. 2), as it takes longer for IZZK (SEQ ID NO: 25) to form a gel at the concentrations of 1 mg/ml and 2 mg/ml, compared to IIZK (SEQ ID NO: 9).

Figure 3:
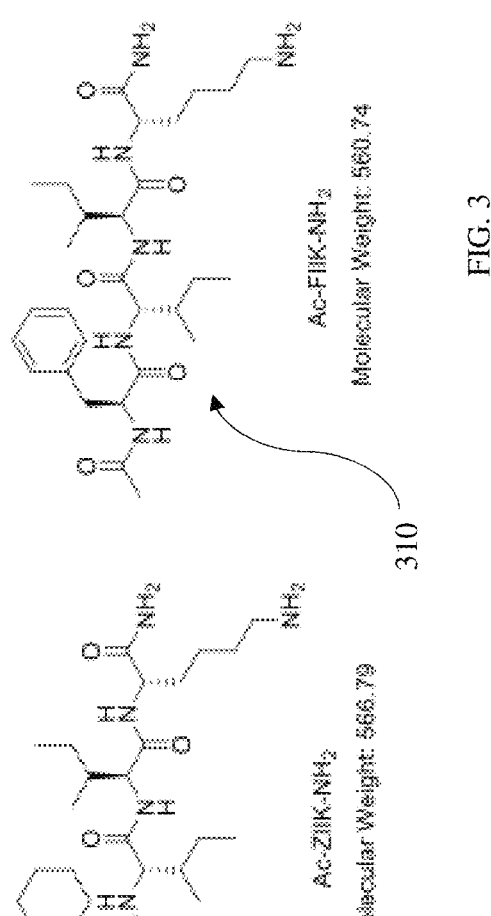
FIG. 3 is a graph showing the molecular structure of IFFK (SEQ ID NO: 17), FFIK (SEQ ID NO: 33), ZZIK (SEQ ID NO: 41), ZIIK (SEQ ID NO: 57), and FIIK (SEQ ID NO: 49) according to an embodiment of the present disclosure.
Figure 4:
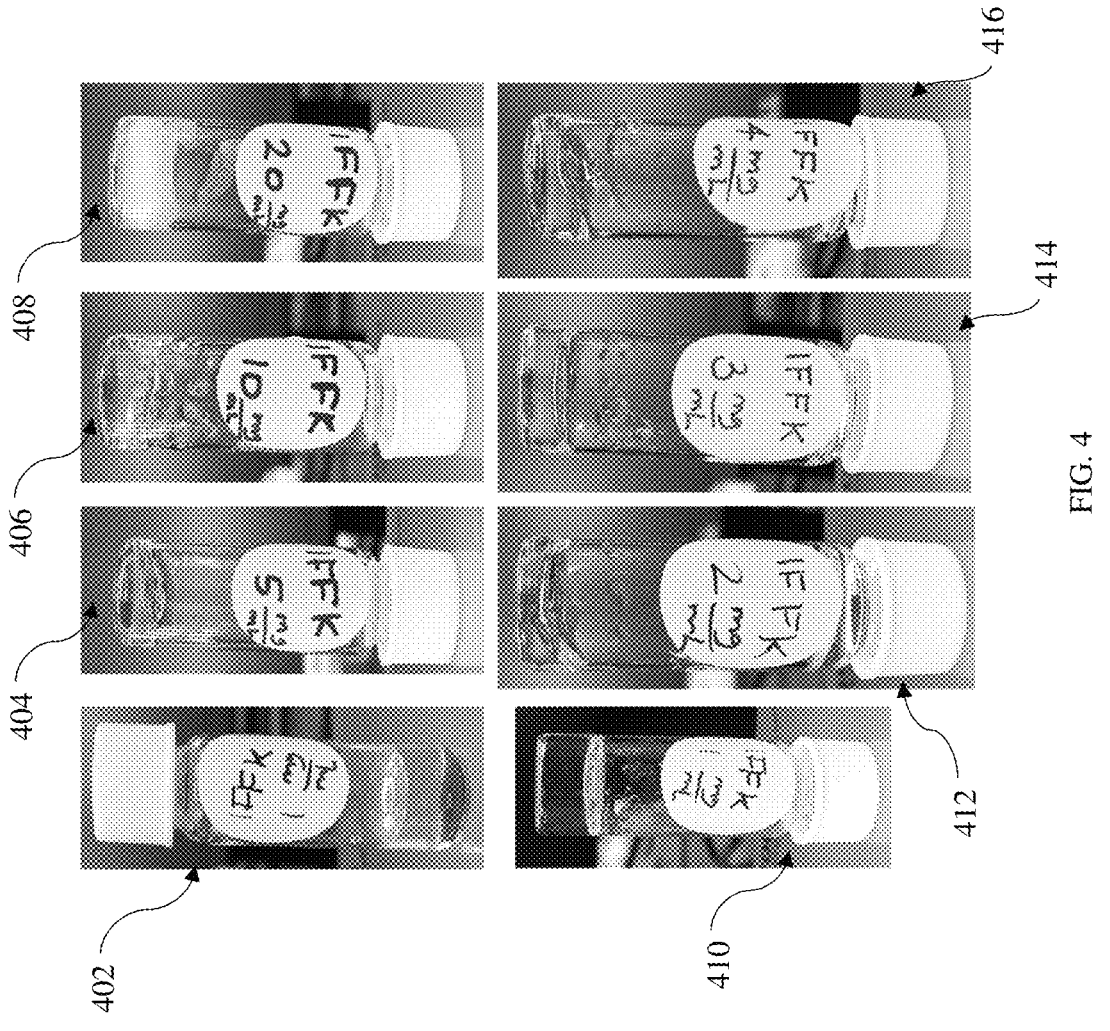
FIG. 4 is a graph showing the IIFK (SEQ ID NO: 1) hydrogel formed at different concentration according to an embodiment of the present disclosure.
Figure 5:
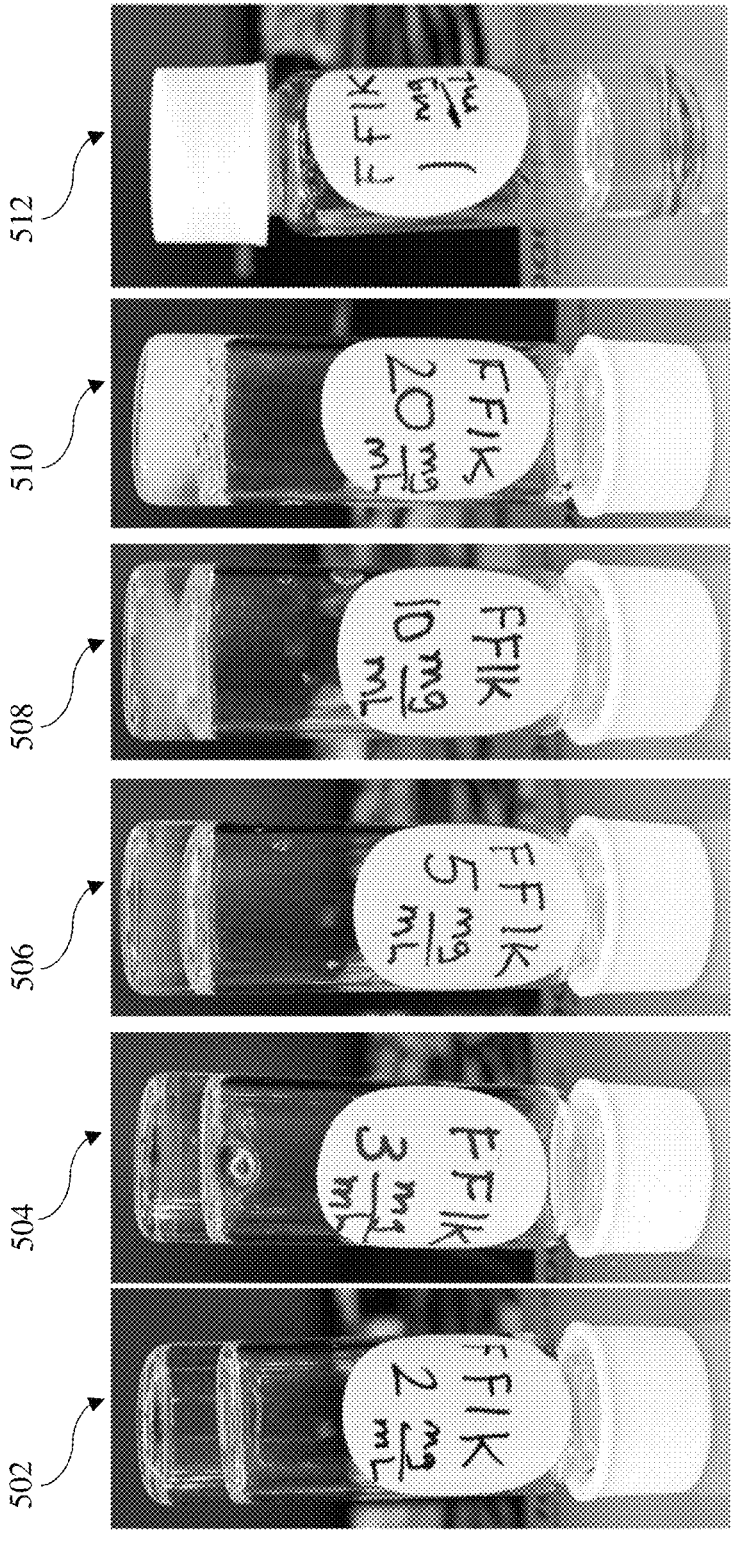
FIG. 5 is a graph showing the FFIK (SEQ ID NO: 33) hydrogel formed at different concentration according to an embodiment of the present disclosure.
Figure 6:
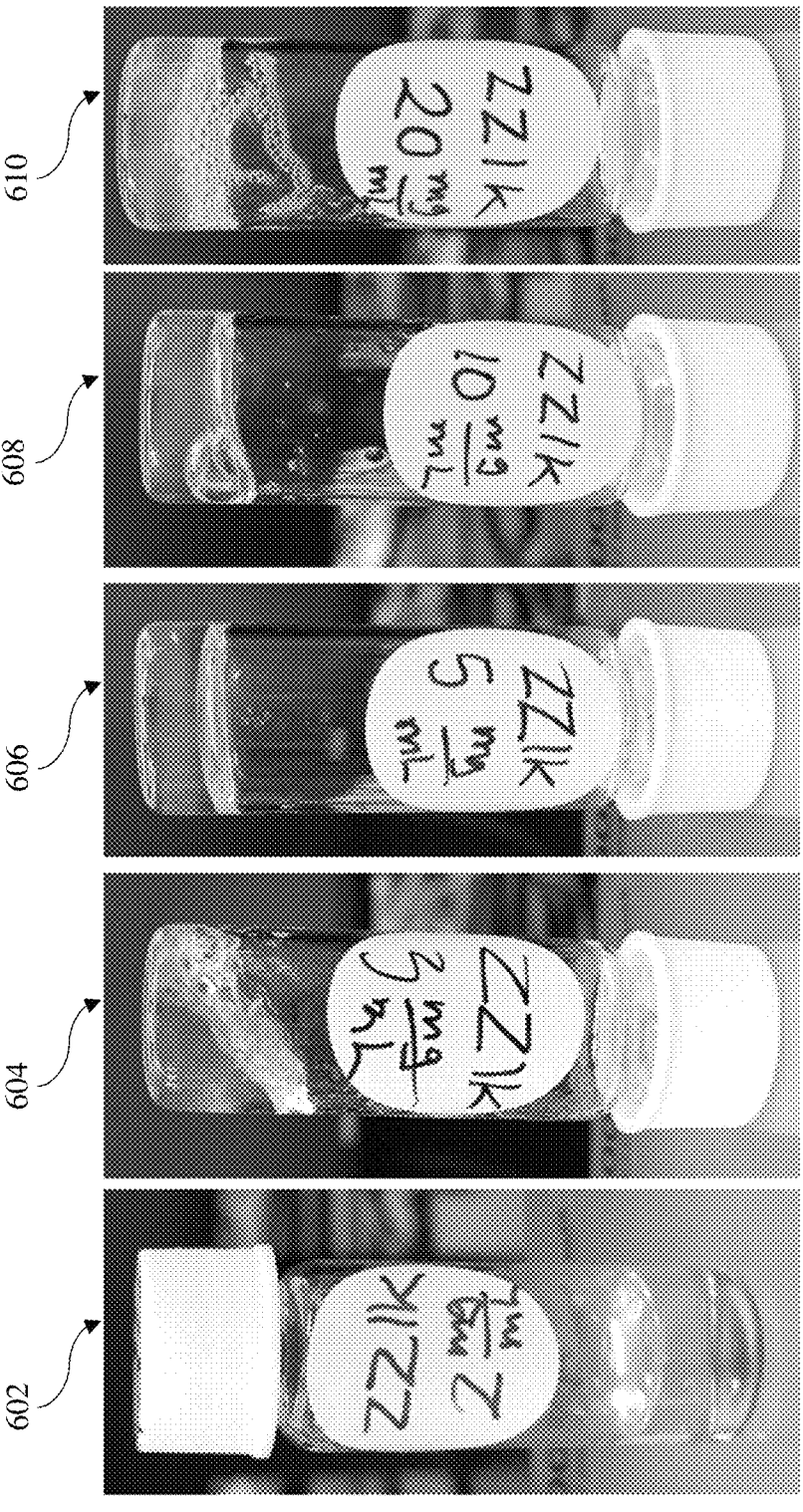
FIG. 6 is a graph showing the ZZIK (SEQ ID NO: 41) hydrogel formed at different concentration according to an embodiment of the present disclosure.
Figure 7:
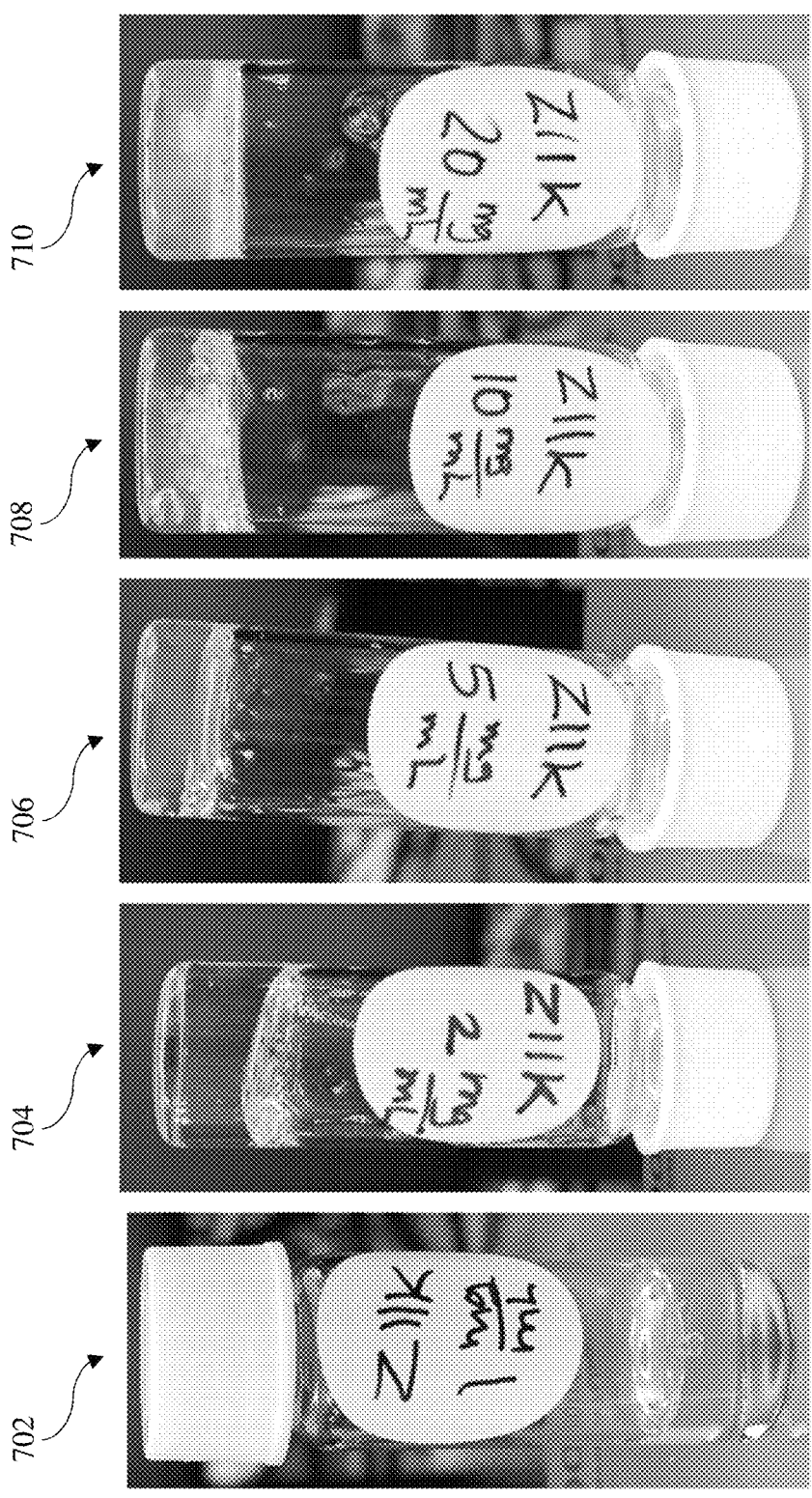
FIG. 7 is a graph showing the ZIIK (SEQ ID NO: 57) hydrogel formed at different concentration according to an embodiment of the present disclosure.
Figure 8:
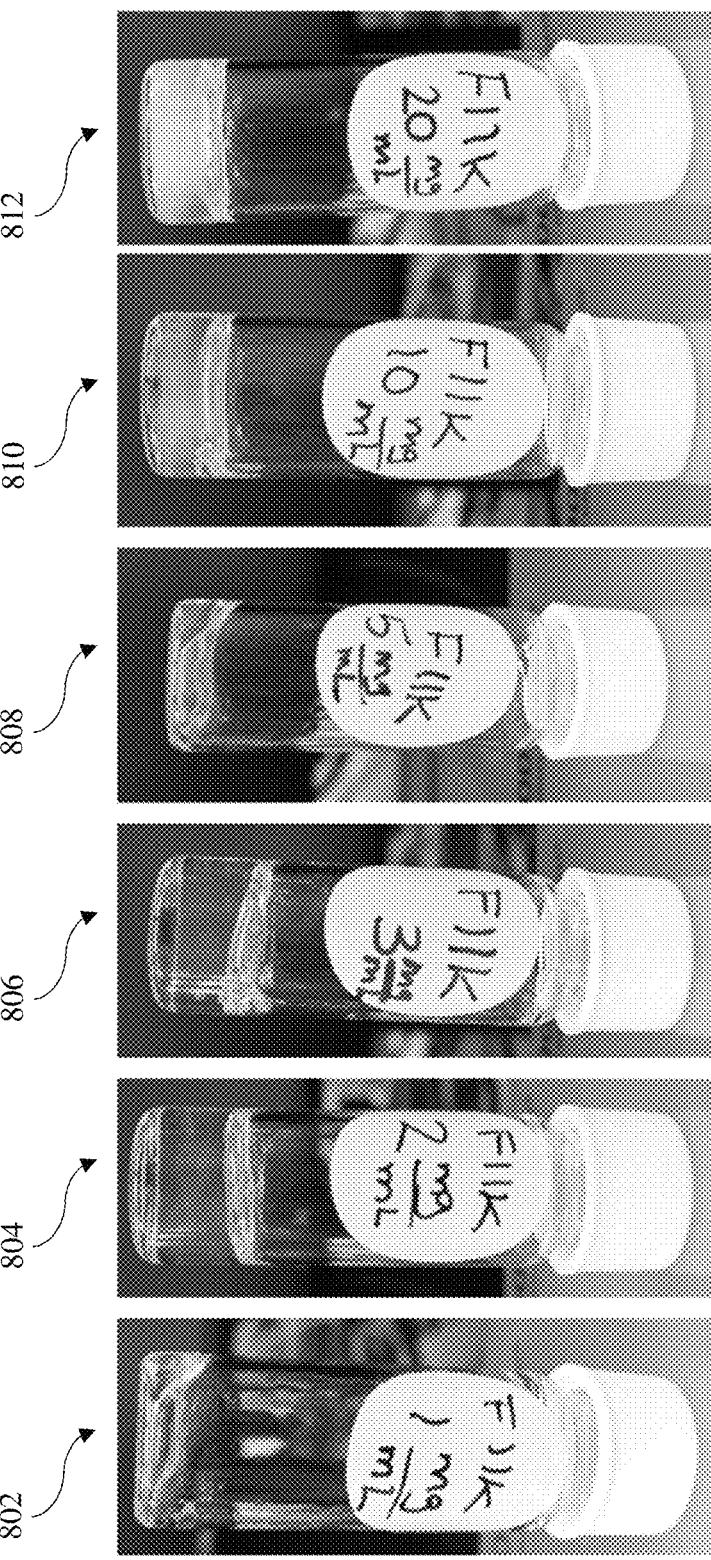
FIG. 8 is a graph showing the FIIK (SEQ ID NO: 49) hydrogel formed at different concentration according to an exemplary embodiment of the present disclosure.

In another embodiment, the peptide is selected from IFFK (SEQ ID NO: 17), FFIK (SEQ ID NO: 33), ZZIK (SEQ ID NO: 41), ZIIK (SEQ ID NO: 57), and FIIK (SEQ ID NO: 49). FIG. 3 shows the molecular structures of IFFK (SEQ ID NO: 17) 302, FFIK (SEQ ID NO: 33) 304, ZZIK (SEQ ID NO: 41) 306, ZIIK (SEQ ID NO: 57) 308, and FIIK (SEQ ID NO: 49) 310. The results (FIGS. 4-8) show that all five peptides can form a gel at the concentration of at least 2 mg/ml. FIG. 4 shows the gel formed by IFFK (SEQ ID NO: 17) at the concentration of 1 mg/ml 402 and 410, 2 mg/ml 412, 3 mg/ml 414, 4 mg/ml 416, 5 mg/ml 404, 10 mg/ml 406, and 20 mg/ml 408. FIG. 5 shows the gel formed by FFIK (SEQ ID NO: 33) at the concentration of 1 mg/ml 512, 2 mg/ml 502, 3 mg/ml 504, 5 mg/ml 506, 10 mg/ml 508, and 20 mg/ml 510. FIG. 6 shows the gel formed by ZZIK (SEQ ID NO: 41) at the concentration of 2 mg/ml 602, 3 mg/ml 604, 5 mg/ml 606, 10 mg/ml 608, and 20 mg/ml 610. FIG. 7 shows the gel formed by ZIIK (SEQ ID NO: 57) at the concentration of 1 mg/ml 702, 2 mg/ml 704, 5 mg/ml 706, 10 mg/ml 708, and 20 mg/ml 710. FIG. 8 shows the gel formed by FIIK (SEQ ID NO: 49) at the concentration of 1 mg/ml 802, 2 mg/ml 804, 3 mg/ml 806, 5 mg/ml 808, 10 mg/ml 810, and 20 mg/ml 812.

The gelation times of each peptide at different concentration are listed in the table below.

| Concentration | IFFK (SEQ ID NO: 17) | FFIK (SEQ ID NO: 33) | ZZIK (SEQ ID NO: 41) | ZIIK (SEQ ID NO: 57) | FIIK (SEQ ID NO: 49) |
|---|---|---|---|---|---|
| 1 mg/ml | >1 h Slightly soft gel | Does not gel in 1 h | — | <1 h Very soft gel | <15 min Soft gel |
| 2 mg/ml | <10 min | <10 min | <10 min Soft gel | <10 min | <5 min |
| 3 mg/ml | <5 min | <10 min | <45 min (<5 min Soft gel) | — | <10 min |
| 4 mg/ml | <5 min | — | — | — | — |
| 5 mg/ml | <5 min | <5 min | <5 min | <10 min | <10 min |
| 10 mg ml | <5 min | <5 min | <5 min | <5 min | <5 min |
| 20 mg/ml | <5 min | <5 min | <5 min | <5 min | <5 min |

Figure 9:
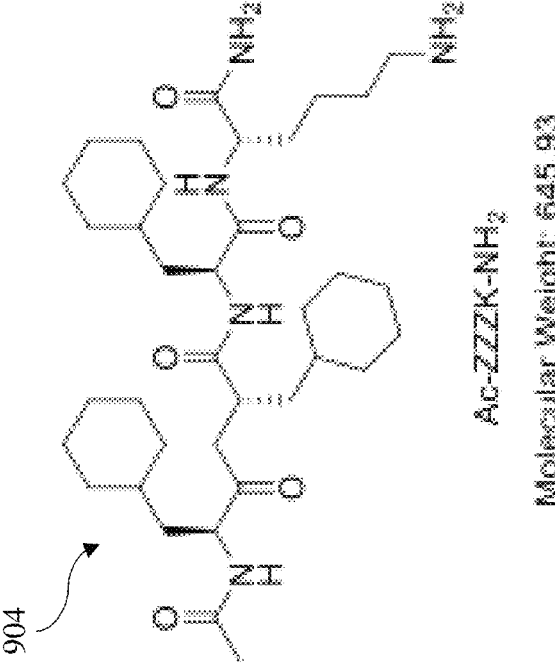
FIG. 9 is a graph showing the molecular structure of FFFK (SEQ ID NO: 65), and ZZZK (SEQ ID NO: 66) according to an exemplary embodiment of the present disclosure.
Figure 10:
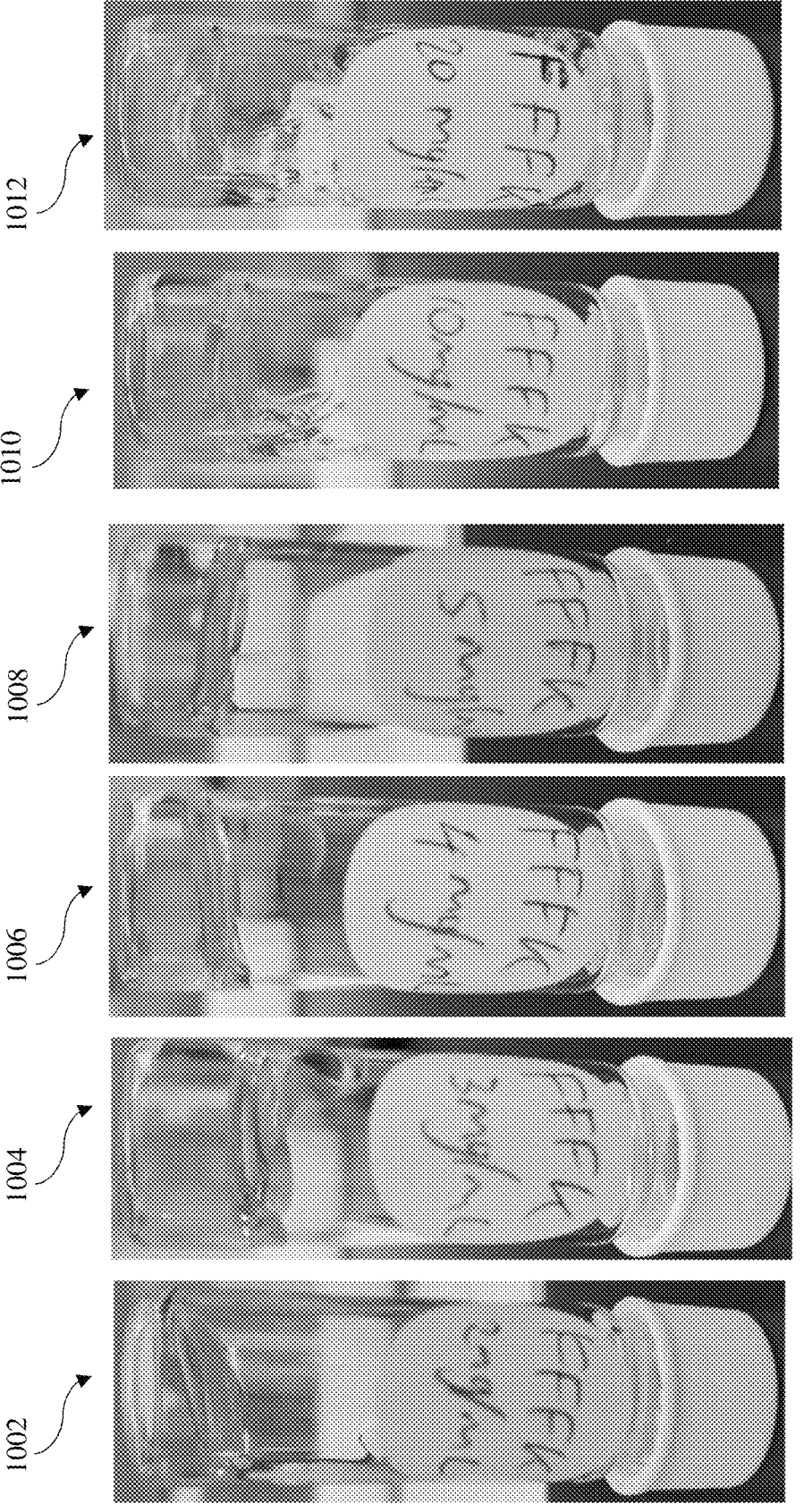
FIG. 10 is a graph showing the FFFK (SEQ ID NO: 65) hydrogel formed at different concentration according to an exemplary embodiment of the present disclosure.
Figure 11:
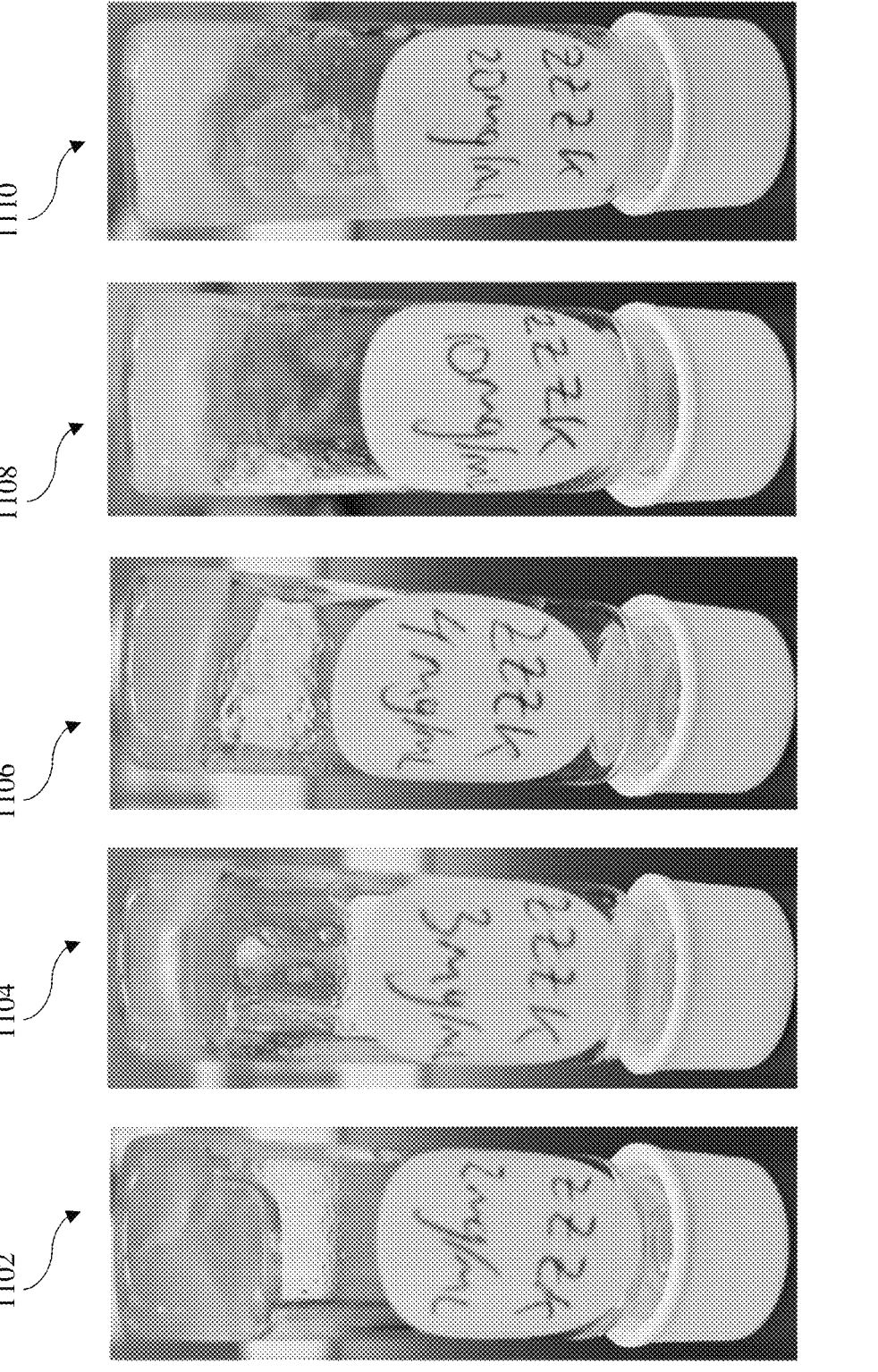
FIG. 11 is a graph showing the ZZZK (SEQ ID NO: 66) hydrogel formed at different concentration according to an exemplary embodiment of the present disclosure.

In another embodiment, the peptide is selected from FFFK (SEQ ID NO: 65) and ZZZK (SEQ ID NO: 66). FIG. 9 shows the molecular structures of FFFK (SEQ ID NO: 65) 902, and ZZZK (SEQ ID NO: 66) 904. The results (FIGS. 10 and 11) show that both peptides can form a gel at the concentration of 2 mg/ml. FIG. 10 shows the gel formed by FFFK (SEQ ID NO: 65) at the concentration of 2 mg/ml 1002, 3 mg/ml 1004, 4 mg/ml 1006, 5 mg/ml 1008, 10 mg/ml 1010, and 20 mg/ml 1012. FIG. 11 shows the gel formed by ZZZK (SEQ ID NO: 66) at the concentration of 2 mg/ml 1102, 3 mg/ml 1104, 4 mg/ml 1106, 10 mg/ml 1108, and 20 mg/ml 1110.

The gelation times of either peptide at different concentration are listed in the table below.

| Concentration | FFFK (SEQ ID NO: 65) | ZZZK (SEQ ID NO: 66) |
|---|---|---|
| 2 mg/ml | <15 min | <30 min |
| 3 mg/ml | <10 min | <30 min |
| 4 mg/ml | <5 min | <30 min |
| 5 mg/ml | <5 min | — |
| 10 mg ml | <2 min | <5 min |
| 20 mg/ml | simultaneously | <3 min |

Figure 12:
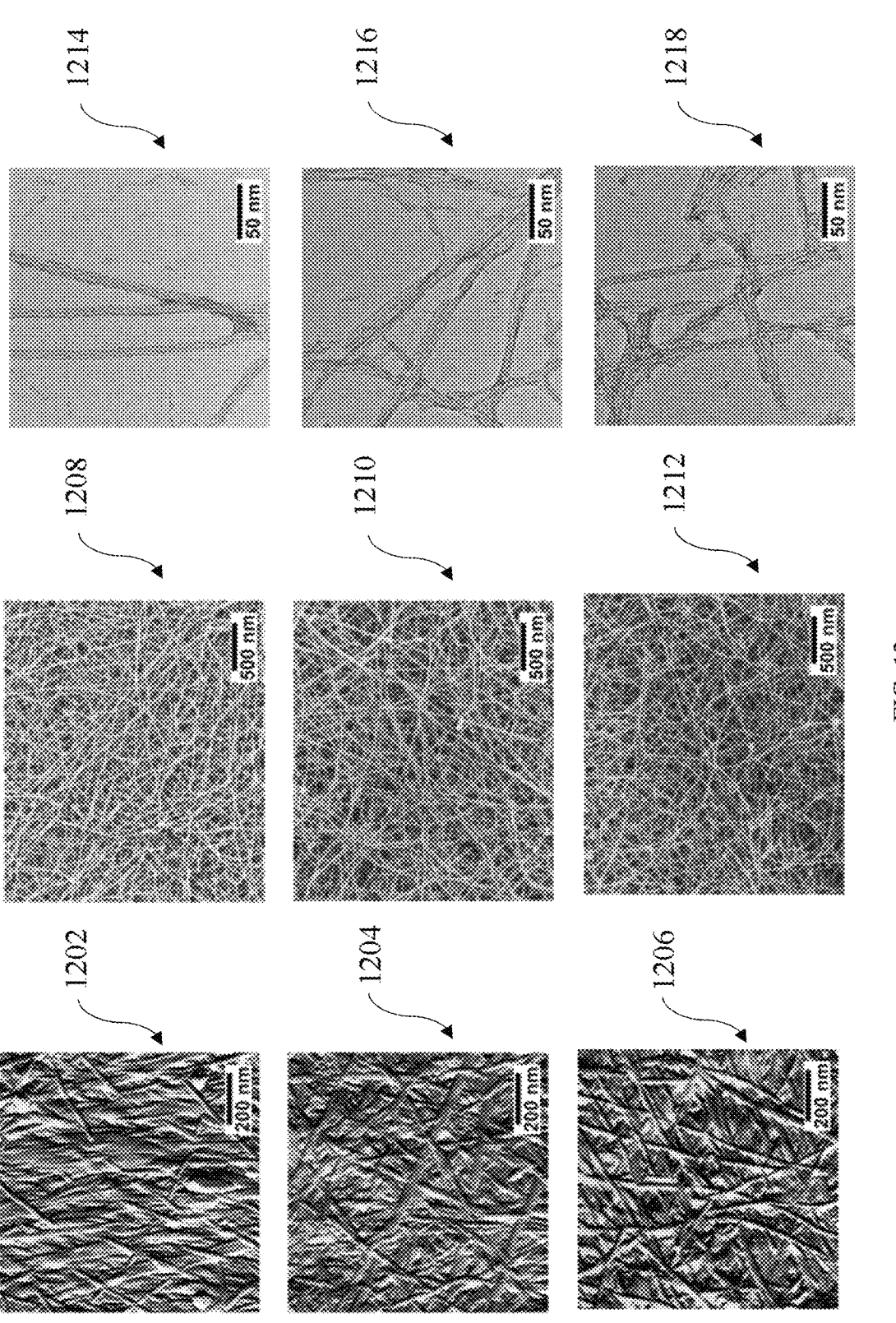
FIG. 12 is an electron micrograph showing the network within the hydrogels formed by IIFK (SEQ ID NO: 1), IIZK (SEQ ID NO: 9) and IZZK (SEQ ID NO: 25) according to an exemplary embodiment of the present disclosure.

In one preferred embodiment, the peptide, selecting from IIFK (SEQ ID NO: 1), IIZK (SEQ ID NO: 9) and IZZK (SEQ ID NO: 25), is dissolved in water at the concentration of 10 mg/ml. The peptide solution is allowed to form a hydrogel for 24 h. Then, the complexity of the fiber structure of the hydrogel is visualized using microscopies. FIG. 12 shows: AFM images of IIFK (SEQ ID NO: 1) (1202), IIZK (SEQ ID NO: 9) (1204), and IZZK (SEQ ID NO: 25) (1206) fibers; SEM micrographs of IIFK (SEQ ID NO: 1) (1208), IIZK (SEQ ID NO: 9) (1210), and IZZK (SEQ ID NO: 25) (1212) gels; and TEM micrographs of IIFK (SEQ ID NO: 1) (1214), IIZK (SEQ ID NO: 9) (1216), and IZZK (SEQ ID NO: 25) (1218) fibers.

In one embodiment, the present disclosure provides a hydrogel or organogel comprising a peptide according to the present disclosure, as defined above.

Figure 13:
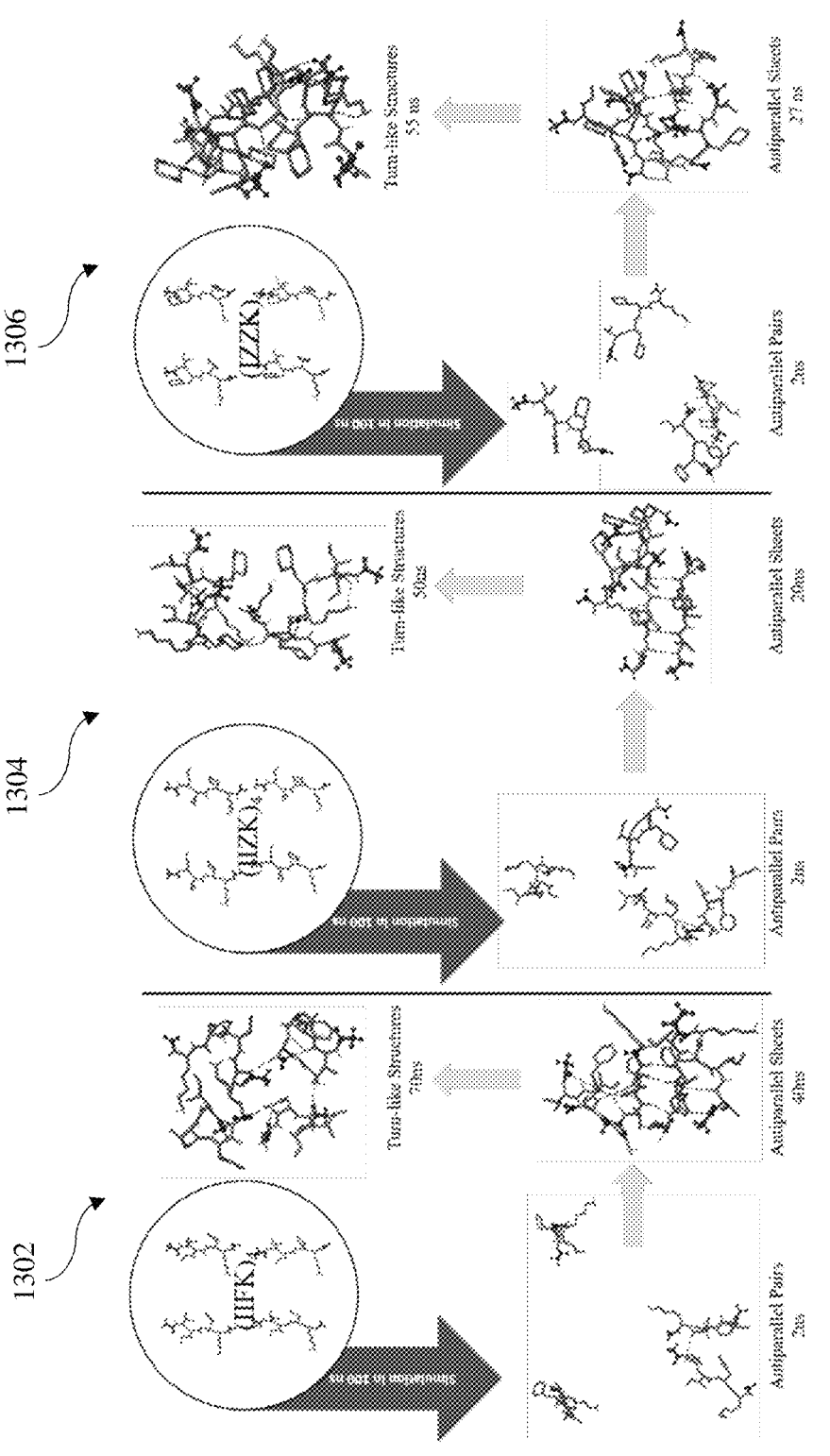
FIG. 13 is a graph illustrating the 4-peptide assemblies of IIFK (SEQ ID NO: 1), IIZK (SEQ ID NO: 9) and IZZK (SEQ ID NO: 25) according to an exemplary embodiment of the present disclosure.
Figure 14:
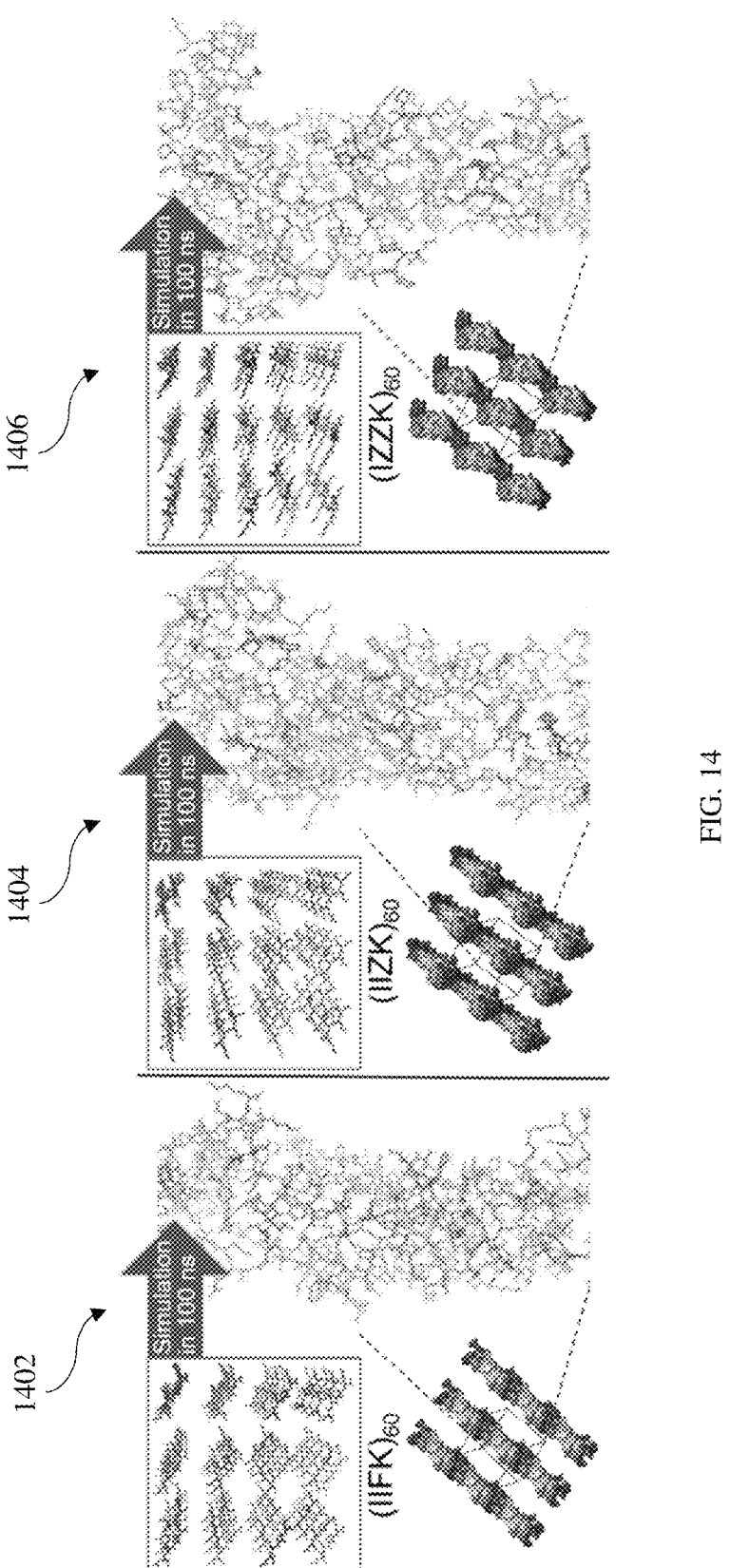
FIG. 14 is a graph illustrating the 60-peptide assemblies of IIFK (SEQ ID NO: 1), IIZK (SEQ ID NO: 9) and IZZK (SEQ ID NO: 25) according to an exemplary embodiment of the present disclosure.

In one embodiment, the self-assembly process is analyzed through molecular dynamic (MD) simulations, simulating the 2-, 4-, and 60-peptide assemblies of IIFK (SEQ ID NO: 1), IIZK (SEQ ID NO: 9), and IZZK (SEQ ID NO: 25) dissolved in water. FIG. 13 shows the 4-peptide assemblies of IIFK (SEQ ID NO: 1) 1302, IIZK (SEQ ID NO: 9) 1304, and IZZK (SEQ ID NO: 25) 1306. FIG. 14 shows the 60-peptide assemblies of IIFK (SEQ ID NO: 1) 1402, IIZK (SEQ ID NO: 9) 1404, and IZZK (SEQ ID NO: 25) 1406. As shown in FIGS. 13 and 14, 4-peptide (FIG. 13) and 60-peptide (FIG. 14) assemblies of IIFK (SEQ ID NO: 1), IIZK (SEQ ID NO: 9), and IZZK (SEQ ID NO: 25) lead to the formation of conformers and a network of hydrogel.

As shown in this simulation, Cha is less solvent accessible than Phe. Distribution of distance between closest water (hydrogen atom HW and oxygen atom OW) and sidechain carbons in F (Phe) and Z (Cha). The median of the distance between sidechain carbons and HW are 0.44 nm (Phe, IIFK (SEQ ID NO: 1)), 0.47 nm (Cha, IIZK (SEQ ID NO: 9)), 0.47 nm (1st Cha, IZZK (SEQ ID NO: 25)) and 0.46 nm (2nd Cha, IZZK (SEQ ID NO: 25)). The median of the distance between sidechain carbons and OW are 0.48 nm (Phe, IIFK (SEQ ID NO: 1)), 0.50 nm (Cha, IIZK (SEQ ID NO: 9)), 0.50 nm (1st Cha, IZZK (SEQ ID NO: 25)) and 0.49 nm (2nd Cha, IZZK (SEQ ID NO: 25)). Therefore, the results confirm that the Cha sidechain in IIZK (SEQ ID NO: 9)/IZZK (SEQ ID NO: 25) played a distinctive role in the fibril assembly.

In one embodiment, the hydrogel is stable in aqueous solution at ambient temperature for a period of at least 1 month, preferably at least 2 to 4 months, more preferably at least 6 to 12 months.

Figure 15:
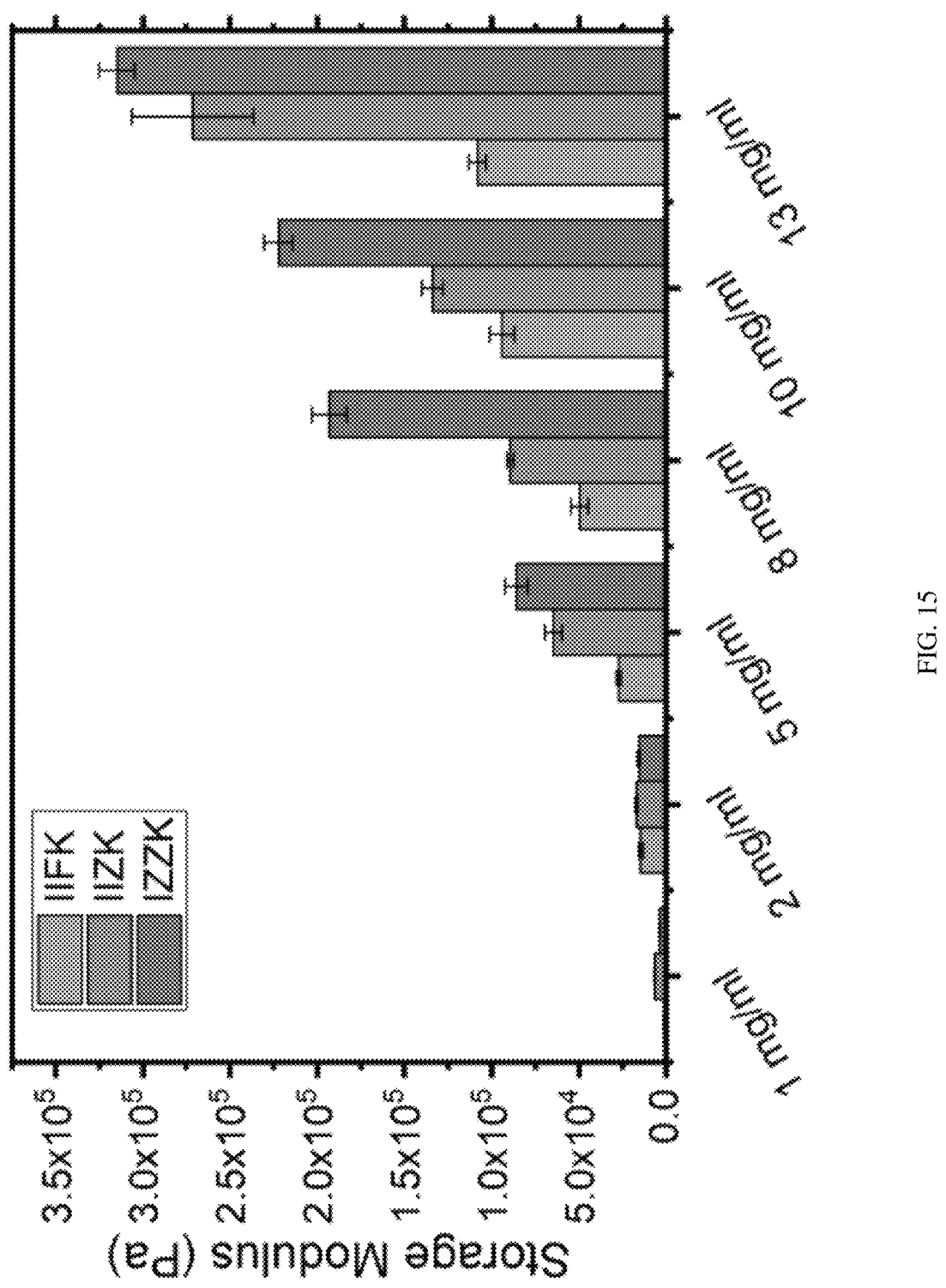
FIG. 15 a graph showing the storage modulus of IIFK (SEQ ID NO: 1), IIZK (SEQ ID NO: 9) and IZZK (SEQ ID NO: 25) at different concentration according to an exemplary embodiment of the present disclosure.

In one embodiment, the hydrogel or organogel is characterized by a storage modulus G' from 1250 Pa to 300,000 Pa, loss modulus G" from around 0.13 KPa to around 54.56 kPa, and loss factor tan δ (G"/G') from 0.08 to 0.17. FIG. 15 shows the storage modulus G', loss modulus G" and loss factor tan δ (G"/G') of hydrogels formed by IIFK (SEQ ID NO: 1), IIZK (SEQ ID NO: 9), and IZZK (SEQ ID NO: 25) at different concentrations, which is also summarized in the table below.

| Peptide | Concentration | Storage Modulus (G', kPa) | Loss Modulus (G', kPa) | tan δ (G''/G') |
|---|---|---|---|---|
| IIFK (SEQ ID NO: 1) | 1 mg/mL (1.78 mM) | 1.25 ± 0.86 | 0.13 ± 0.04 | 0.10 |
| | 2 mg/mL (3.56 mM) | 14.45 ± 1.37 | 1.31 ± 0.12 | 0.09 |
| | 5 mg/mL (8.90 mM) | 27.26 ± 1.30 | 2.39 ± 0.11 | 0.09 |
| | 8 mg/mL (14.2 mM) | 49.74 ± 5.02 | 5.00 ± 0.31 | 0.10 |
| | 10 mg/mL (17.8 mM) | 94.18 ± 7.12 | 9.04 ± 0.56 | 0.10 |
| | 13 mg/mL (23.1 mM) | 108.21 ± 5.02 | 8.90 ± 0.36 | 0.08 |
| IIZK (SEQ ID NO: 9) | 1 mg/mL (1.76 mM) | 6.52 ± 0.18 | 0.88 ± 0.04 | 0.13 |
| | 2 mg/mL (3.52 mM) | 16.82 ± 0.72 | 2.02 ± 0.09 | 0.12 |
| | 5 mg/mL (8.80 mM) | 64.74 ± 4.89 | 7.08 ± 0.59 | 0.11 |
| | 8 mg/mL (14.1 mM) | 89.40 ± 1.86 | 10.91 ± 0.44 | 0.12 |
| | 10 mg/mL (17.6 mM) | 134.04 ± 5.99 | 15.54 ± 0.68 | 0.12 |
| | 13 mg/ml (22.9 mM) | 271.34 ± 35.09 | 37.76 ± 2.38 | 0.14 |
| IZZK (SEQ ID NO: 25) | 1 mg/mL (1.65 mM) | 3.71 ± 0.19 | 0.36 ± 0.08 | 0.10 |
| | 2 mg/mL (3.30 mM) | 15.53 ± 0.74 | 1.44 ± 0.07 | 0.09 |
| | 5 mg/mL (8.25 mM) | 85.87 ± 6.50 | 11.60 ± 0.51 | 0.14 |
| | 8 mg/ml (13.2 mM) | 193.09 ± 10.13 | 29.70 ± 1.54 | 0.15 |
| | 10 mg/mL (16.5 mM) | 222.13 ± 8.16 | 39.71 ± 1.50 | 0.18 |
| | 13 mg/mL (21.5 mM) | 314.91 ± 10.10 | 54.56 ± 1.46 | 0.17 |

In one embodiment, the hydrogel or organogel has a higher mechanical strength than collagen or its hydrolyzed form (gelatin).

In one embodiment, the hydrogel formed by IIFK (SEQ ID NO: 1), IIZK (SEQ ID NO: 9), and IZZK (SEQ ID NO: 25) is characterized by a viscosity in the range of 0.4-0.6 Pa's, at the concentration of 13 mg/ml in 1×PBS buffer at a shear rate 29.7 s$^{-1}$. The viscosities of the solution of and gel formed by each peptide is summarized in the table below. The viscosities of peptide hydrogels are examined under continuous flow with increasing shear rate and can provide an insight into their potential use as bioinks for extrusion-based bioprinting. The results confirm that hydrogels formed by IIFK (SEQ ID NO: 1), IIZK (SEQ ID NO: 9), and IZZK (SEQ ID NO: 25) are suitable for extrusion bioprinters.

| Peptides | Viscosity (Pa · s) |
|---|---|
| IIFK (SEQ ID NO: 1) gel | 0.56 |
| IZZK (SEQ ID NO: 25) gel | 0.48 |
| IIZK (SEQ ID NO: 9) gel | 0.47 |
| IIFK (SEQ ID NO: 1) solution | 0.09 |
| IZZK (SEQ ID NO: 25) solution | 0.06 |
| IIZK (SEQ ID NO: 9) solution | 0.03 |

In one embodiment, IIFK (SEQ ID NO: 1), IIZK (SEQ ID NO: 9), and IZZK (SEQ ID NO: 25) are used for bioprinting with printing parameters: dissolved in 7×PBS, flow rates of 60 μL/min for peptide and 20 μL/min for PBS, and peptide concentration of 13 mg/ml.

Figure 16:
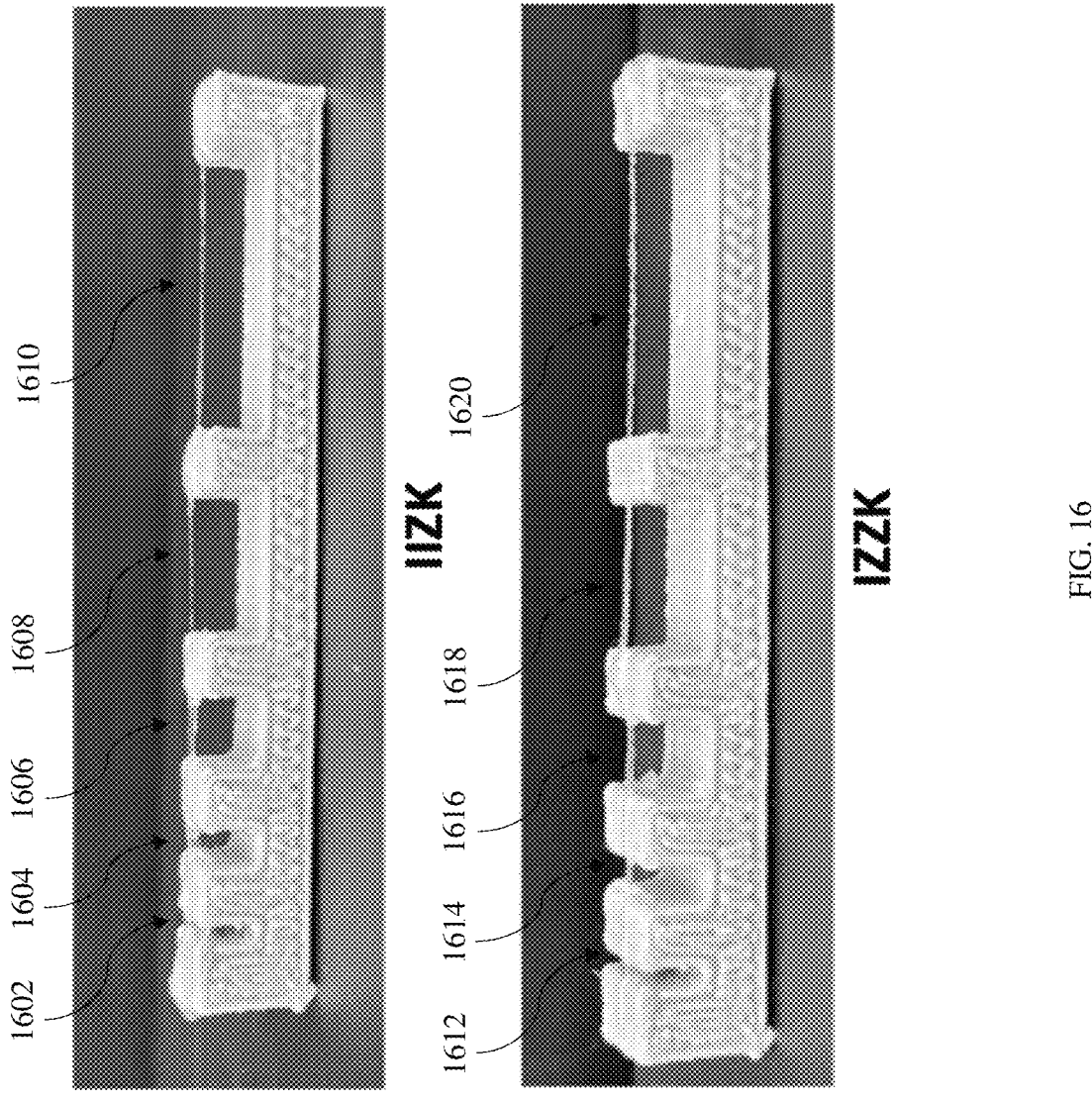
FIG. 16 a graph showing the filament construct formed by IIZK (SEQ ID NO: 9) and IZZK (SEQ ID NO: 25) hydrogels according to an exemplary embodiment of the present disclosure.

In one embodiment, hydrogel constructs formed by IIZK (SEQ ID NO: 9), and IZZK (SEQ ID NO: 25) are characterized by mechanical stiffness allowing the printed filament to hold its shape without or with only slight sagging over 1, 2, 4, 8, and 16 mm gaps. FIG. 16 shows the IIZK (SEQ ID NO: 9) filament over 1 mm (1602), 2 mm (1604), 4 mm (1606), 8 mm (1608), and 16 mm (1610) gaps and IZZK (SEQ ID NO: 25) filament over 1 mm (1612), 2 mm (1614), 4 mm (1616), 8 mm (1618), and 16 mm (1620) gaps.

Figure 17:
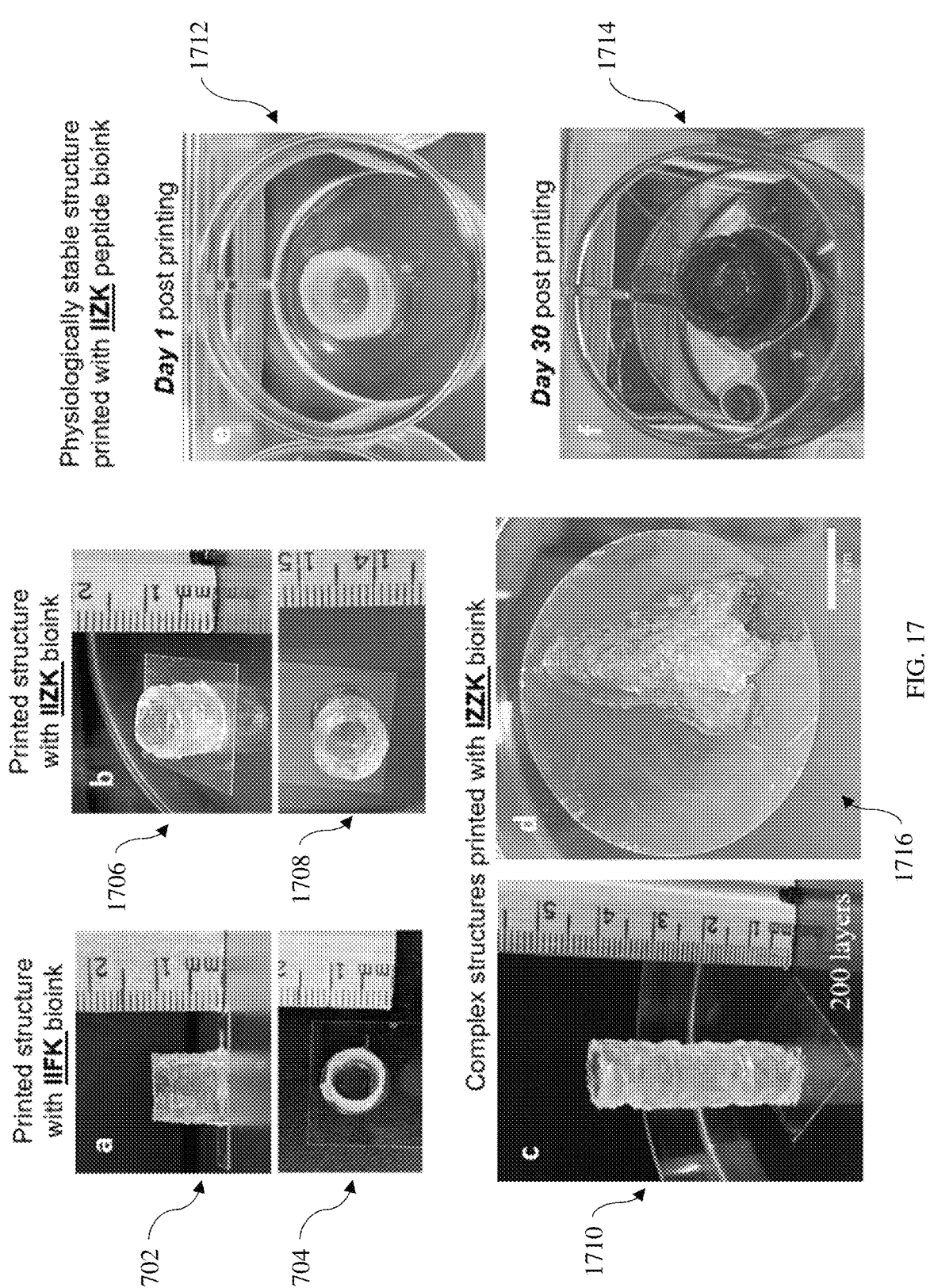
FIG. 17 a graph showing the hollow cylindrical constructs and human-like nose construct printed using the hydrogels described in the present disclosure according to an exemplary embodiment of the present disclosure.

In another embodiment, the hydrogel constructs formed by IIFK (SEQ ID NO: 1), IIZK (SEQ ID NO: 9), and IZZK (SEQ ID NO: 25) are hollow cylindrical constructs and can hold their shapes with a height of 10 mm or higher (multiple layers). As shown in FIG. 17, the IZZK (SEQ ID NO: 25) construct of 40 mm height (200 layers) 1710 is printed using 6 mL of the peptide without any deformation. The IIZK (SEQ ID NO: 9) construct is able to achieve a height of 38 mm (180 layers) using 4 ml of the peptide (not shown). The IIFK (SEQ ID NO: 1) construct 1702 and IIZK (SEQ ID NO: 9) construct 1706 are able to achieve a height of 10 mm. The diameters of the IIFK (SEQ ID NO: 1) construct 1704 and IIZK (SEQ ID NO: 9) construct 1708 are about 10 mm.

In another embodiment, the hollow cylindrical construct can hold its shape for up to 30 days 1714 as shown in FIG. 17.

In a preferred embodiment, the IZZK (SEQ ID NO: 25) bioink prints a human-like nose construct 1716, hence further demonstrating the peptide's printability for complex constructs and intrinsically-detailed shapes (FIG. 17).

In a further aspect, the present disclosure also relates to a method of preparing a hydrogel or organogel, the method comprising dissolving a peptide according to the present disclosure in an aqueous solution or an organic solution, respectively.

In one embodiment, the dissolved peptide in aqueous or organic solution is further exposed to temperature, wherein the temperature is in the range from 20° C. to 90° C., preferably from 20° C. to 70° C. Embodiments of the present disclosure also include a hydrogel, which can be taken to be a water-swollen water-insoluble polymeric material. The hydrogel includes, including contains and consists of, a peptide and/or peptoid as defined above. Since a hydrogel maintains a three-dimensional structure, a hydogel of an embodiment of the invention may be used for a variety of applications. Since the hydrogel has a high-water content and includes amino acids, it is typically of excellent bio-compatibility. A hydrogel according to an embodiment of the invention is typically formed by self-assembly. The inventors have observed that the peptides/peptoids assemble into fibers that form mesh-like structures. Without being bound by theory hydrophobic interaction between non-polar portions of peptides/peptoids of an embodiment of the invention are contemplated to assist such self-assembly process.

The method of forming the hydrogel includes dissolving the peptide/peptoid in aqueous solution. Agitation, including mixing such as stirring, and/or sonication may be employed to facilitate dissolving the peptide/peptoid. In some embodiments the aqueous solution with the peptide/peptoid therein is exposed to a temperature below ambient temperature, such as a temperature selected from about 2° C. to about 15° C. In some embodiments the aqueous solution with the peptide/peptoid therein is exposed to an elevated temperature, i.e. a temperature above ambient temperature. Typically, the aqueous solution is allowed to attain the temperature to which it is exposed. The aqueous solution may for example be exposed to a temperature from about 25° C. to about 85° C. or higher, such as from about 25° C. to about 75° C., from about 25° C. to about 70° C., from about 30° C. to about 70° C., from about 35° C. to about 70° C., from about 25° C. to about 60° C., from about 30° C. to about 60° C., from about 25° C. to about 50° C., from about 30° C. to about 50° C. or from about 40° C. to about 65° C., such as e.g. a temperature of about 40° C., about 45° C., about 50° C., about 55° C., about 60° C. or about 65° C. The aqueous solution with the peptide/peptoid therein may be maintained at this temperature for a period of about 5 min to about 10 hours or more, such as about 10 min to about 6 hours, about 10 min to about 4 hours, about 10 min to about 2.5 hours, about 5 min to about 2.5 hours, about 10 min to about 1.5 hours or about 10 min to about 1 hour, such as about 15 min, about 20 min, about 25 min, about 30 min, about 35 min or about 40 min.

A hydrogel according to an embodiment of the invention may be included in a fuel cell, where it may for example provide a substrate between the anode and the cathode, a liquid electrolyte may be encompassed by the hydrogel. Likewise, a hydrogel according to an embodiment of the invention may provide a substrate between two electrodes in an electrophoresis apparatus. The hydrogel may also be conducting. The hydrogel may also serve in enhancing the efficiency of charge-separated states and/or slowing down charge recombination. The hydrogel may thus be applied in any form photovoltaics, including a solar cell.

In some embodiments a hydrogel disclosed herein is a biocompatible, including a pharmaceutically acceptable hydrogel. The term thus generally refers to the inability of a hydrogel to promote a measurably adverse biological response in a cell, including in the body of an animal, including a human. A biocompatible hydrogel can have one or more of the following properties: non-toxic, non-muta-genic, non-allergenic, non-carcinogenic, and/or non-irritat-ing. A biocompatible hydrogel, in the least, can be innocuous and tolerated by the respective cell and/or body. A biocom-patible hydrogel, by itself, may also improve one or more functions in the body.

Depending on the amino acids that are included in the peptide/peptoid that is included in a hydrogel, a respective hydrogel may be biodegradable. A biodegradable hydrogel gradually disintegrates or is absorbed in vivo over a period of time, e.g., within months or years. Disintegration may for instance occur via hydrolysis, may be catalysed by an enzyme and may be assisted by conditions to which the hydrogel is exposed in a human or animal body, including a tissue, a blood vessel or a cell thereof. Where a peptide is made up entirely of natural amino acids, a respective peptide can usually be degraded by enzymes of the human/animal body.

A hydrogel according to an embodiment of the invention may also serve as a depot for a pharmaceutically active compound such as a drug. A hydrogel according to an embodiment of the invention may be designed to mimic the natural extracellular matrix of an organism such as the human or animal body. A fiber formed from the peptide/peptoid of an embodiment of the invention, including a respective hydrogel, may serve as a biological scaffold. A hydrogel of an embodiment of the invention may be included in an implant, in a contact lens or may be used in tissue engineering. In one embodiment, the peptides consist typically of 3-7 amino acids and are able to self-assemble into complex fibrous scaffolds which are seen as hydrogels, when dissolved in water or aqueous solution. These hydro-gels can retain water up to 99.9% and possess sufficiently high mechanical strength. Thus, these hydrogels can act as artificial substitutes for a variety of natural tissues without the risk of immunogenicity. The hydrogels in accordance with the present disclosure may be used for cultivating suitable primary cells and thus establish an injectable cell-matrix compound in order to implant or re-implant the newly formed cell-matrix in vivo. Therefore, the hydrogels in accordance with the present disclosure are particularly useful for tissue regeneration or tissue engineering applica-tions. Arthroscopic techniques are taken herein as a subset of surgical techniques, and any reference to surgery, surgical, etc., includes arthroscopic techniques, methods and devices. A surgical implant that includes a hydrogel according to an embodiment of the invention may include a peptide and/or peptoid scaffold. This the peptide and/or peptoid scaffold may be defined by the respective hydrogel. A hydrogel of an embodiment of the invention may also be included in a wound cover such as gauze or a sheet, serving in maintain-ing the wound in a moist state to promote healing.

Depending on the amino acid sequence used in the peptide/peptoid the hydrogel may be temperature-sensitive. It may for instance have a lower critical solution temperature or a temperature range corresponding to such lower critical solution temperature, beyond which the gel collapses as hydrogen bonds by water molecules are released as water molecules are released from the gel.

The disclosed subject matter also provides improved chiral amphiphilic natural-based peptides and/or peptoids that assemble to peptide/peptoid hydrogels with very favor-able material properties. The advantage of these peptide/peptoid hydrogels is that they are accepted by a variety of different primary human cells, thus providing peptide scaf-folds that can be useful in the repair and replacement of various tissues. Depending on the chirality of the peptide monomer the character of the hydrogels can be designed to be more stable and less prone to degradation though still biocompatible.

A hydrogel and/or a peptide/peptoid described herein can be administered to an organism, including a human patient per se, or in pharmaceutical compositions where it may include or be mixed with pharmaceutically active ingredi-ents or suitable carriers or excipient(s). Techniques for formulation and administration of respective hydrogels or peptides/peptoids resemble or are identical to those of low molecular weight compounds well established in the art. Exemplary routes include, but are not limited to, oral, transdermal, and parenteral delivery. A hydrogel or a pep-tide/peptoid may be used to fill a capsule or tube or may be provided in compressed form as a pellet. The peptide/peptoid or the hydrogel may also be used in injectable or sprayable form, for instance as a suspension of a respective peptide/peptoid.

A hydrogel of an embodiment of the invention may for instance be applied onto the skin or onto a wound. Further suitable routes of administration may, for example, include depot, oral, rectal, transmucosal, or intestinal administra-tion; parenteral delivery, including intramuscular, subcuta-neous, intravenous, intramedullary injections, as well as intrathecal, direct intraventricular, intraperitoneal, intrana-sal, or intraocular injections: It is noted in this regard that for administering microparticles a surgical procedure is not required. Where the microparticles include a biodegradable polymer there is no need for device removal after release of the anticancer agent. Nevertheless, the microparticles may be included in or on a scaffold, a coating, a patch, composite material, a gel or a plaster.

In some embodiments one may administer a hydrogel and/or a peptide/peptoid in a local rather than systemic manner, for example, via injection or transdermal patch.

Pharmaceutical compositions that include a hydrogel and/or a peptide/peptoid of an embodiment of the present disclosure may be manufactured in a manner that is itself known, e.g., by means of conventional mixing, dissolving, granulating, dragee-making, levigating, emulsifying, encap-sulating, entrapping or lyophilizing processes.

Pharmaceutical compositions for use in accordance with an embodiment of the present disclosure thus may be formulated in conventional manner using one or more physiologically acceptable carriers including excipients and auxiliaries that facilitate processing of the hydrogel and/or peptide/peptoid into preparations that can be used pharmaceutically. Proper formulation is dependent upon the route of administration chosen.

For injection, the peptide/peptoid of an embodiment of the invention may be formulated in aqueous solutions, for instance in physiologically compatible buffers such as Hanks's solution, Ringer's solution, or physiological saline buffer. For transmucosal administration, penetrants appropriate to the barrier to be permeated are used in the formulation. Such penetrants are generally known in the art.

For oral administration, the hydrogel and/or peptide/peptoid can be formulated readily by combining them with pharmaceutically acceptable carriers well known in the art. Such carriers enable the hydrogel and/or peptide/peptoid, as well as a pharmaceutically active compound, to be formulated as tablets, pills, dragees, capsules, liquids, gels, syrups, slurries, suspensions and the like, for oral ingestion by a patient to be treated. Pharmaceutical preparations for oral use can be obtained by adding a solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatine, gum tragacanth, methyl cellulose, hydroxypropylmethyl-cellulose, sodium carboxymethylcellulose, and or polyvinylpyr-rolidone (PVP). If desired, disintegrating agents may be added, such as the cross-linked polyvinyl pyrrolidone, agar, or alginic acid or a salt thereof such as sodium alginate.

Dragee cores are provided with suitable coatings. For this purpose, concentrated sugar solutions may be used, which may optionally contain gum arabic, talc, polyvinyl pyrrolidone, car-bopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations that can be used orally include push-fit capsules made of gelatine, as well as soft, sealed capsules made of gelatine and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the peptides/peptoids may be suspended in suitable liquids, such as fatty oils, liquid paraffin, or liquid polyethylene glycols. In addition, stabilizers may be added. All formulations for oral administration should be in dosages suitable for such administration. For buccal administration, the compositions may take the form of tablets or lozenges formulated in conventional manner.

The hydrogel and/or peptide/peptoid may be formulated for parenteral administration by injection, e.g., by intramuscular injections or bolus injection or continuous infusion. Formulations for injection may be presented in unit dosage form, e. g., in ampules or in multi-dose containers, with an added preservative. The respective compositions may take such forms as suspensions, solutions or emulsions in oily or aqueous vehicles, and may contain formulatory; agents such as suspending, stabilizing and/or dispersing agents.

The hydrogel and/or peptide/peptoid may be formulated for other drug delivery systems like implants, or trandermal patches or stents.

Figure 18:
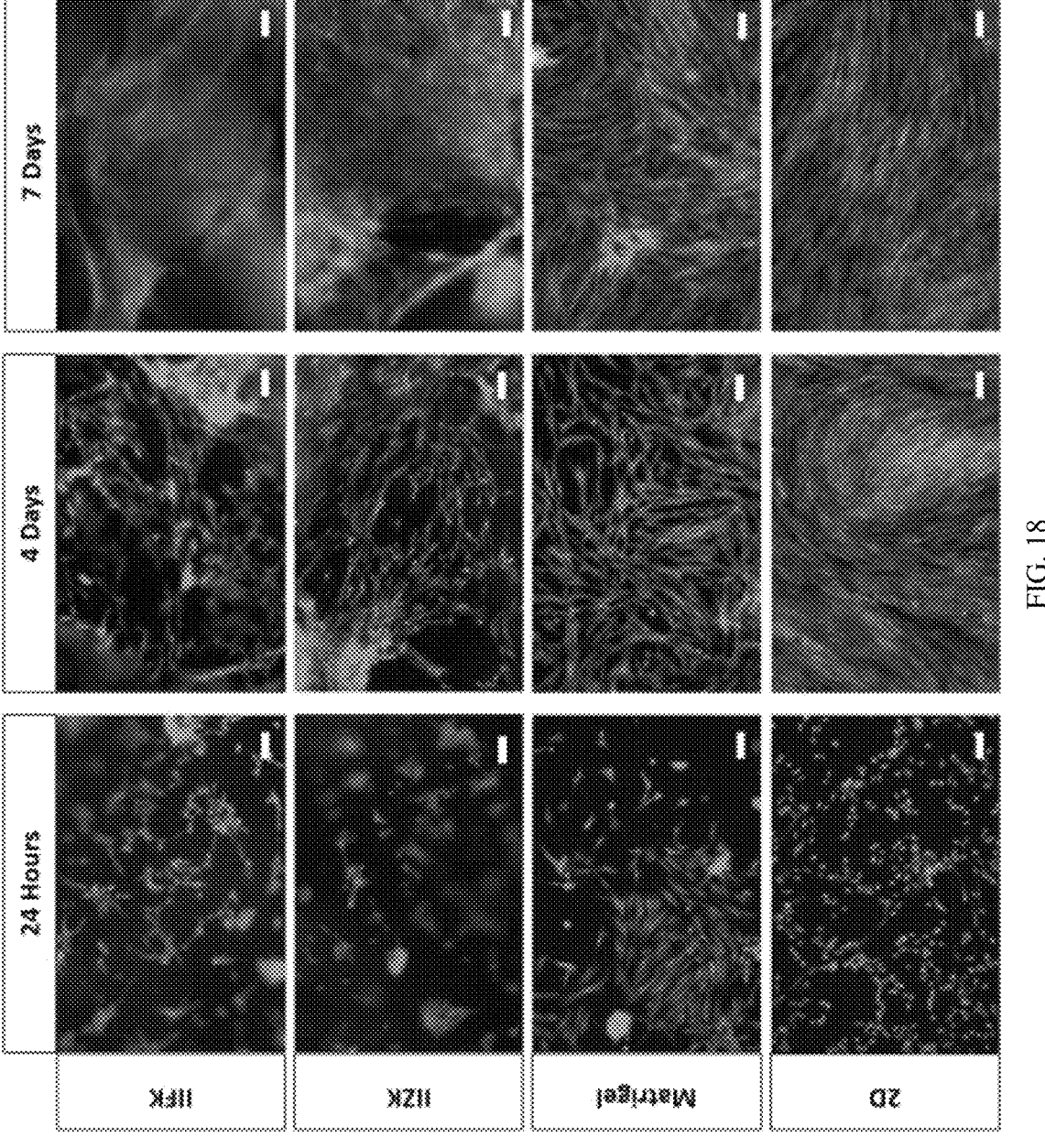
FIG. 18 is a graph showing the cell viability of hDFn within IIFK (SEQ ID NO: 1) and IIZK (SEQ ID NO: 9) peptide hydrogels according to an embodiment of the present disclosure.
Figure 19:
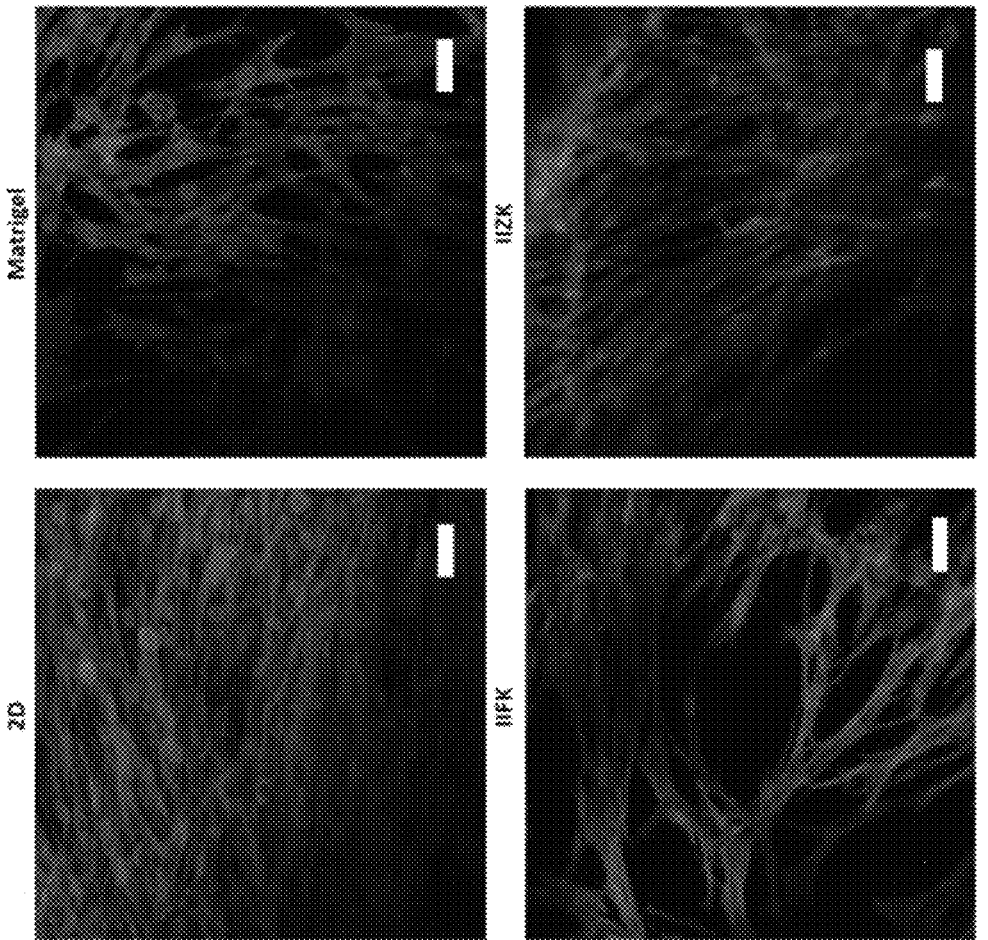
FIG. 19 is a graph showing the cell mophology of hDFn within IIFK (SEQ ID NO: 1) and IIZK (SEQ ID NO: 9) peptide hydrogels versus 2D culture according to an embodiment of the present disclosure.
Figure 20:
FIG. 20 is a graph showing the hDFn proliferation through quantitation of ATP production according to an embodiment of the present disclosure.
Figure 20:
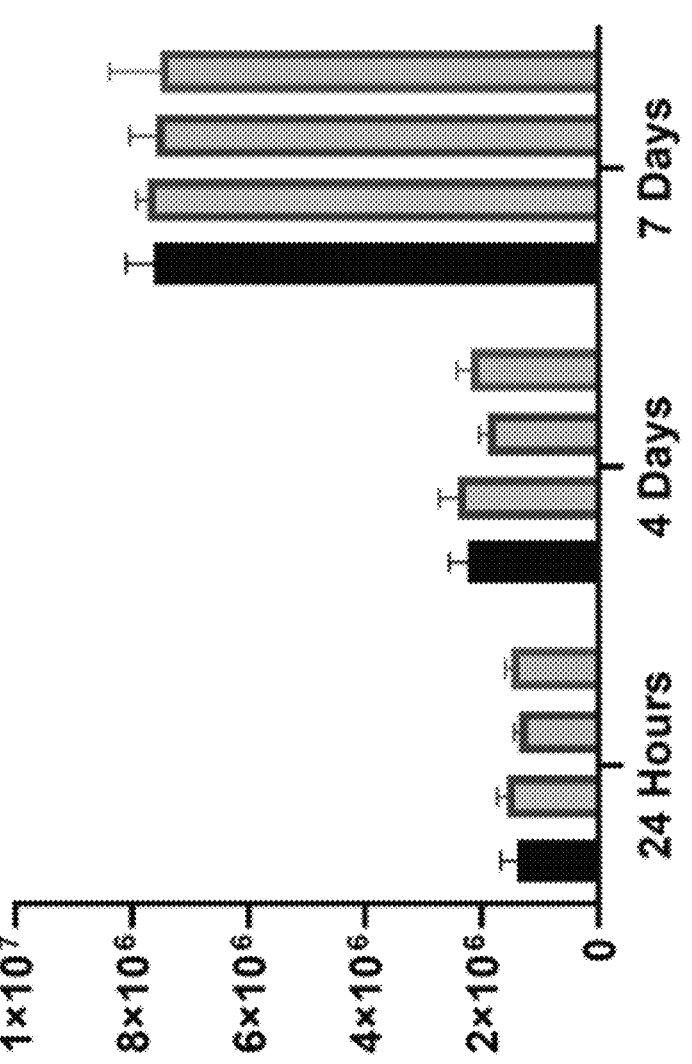

In one embodiment, human dermal fibroblasts (hDF) are cultured within the 3D constructs formed by peptide hydrogels, and cell viability, metabolic activity, and morphology are analyzed. Upon 3D culturing, high cell viability and metabolic activity are confirmed. As shown in FIG. 18-19, the cells cultured in 3D hydrogel constructs are highly stretched and elongated, with well-defined actin fibers. FIG. 20 shows the proliferation of 3D cultured cells through quantitation of ATP production in metabolically active cells. There is an apparent change in cell morphology, as compared to 2D cultured cells, which was also reported by other studies.[23, 24] The biocompatibility of a biomaterial, as indicated by cell viability, cell morphology and metabolic activity, is an essential factor for its potential use as a bioink and in regenerative medicine applications.

In one embodiment, the stiffness of the tetrameric peptide biomaterial in the present disclosure may be modulated, ranging from 3 kPa up to 130 kPa, enabling control over mechanical factors. In vivo cells reside in 3D niches in which different factors, such as mechanical cues, interact and play an essential role in cell function and fate.[30] The ECM provides key cues to cells; for instance, matrix elasticity was found to provide potent cues directing MSCs differentiation without the need for induction cocktails.[31-34] Even with the use of pluripotent stem cells, differentiation toward mature and functional cells was impaired unless used in combination with appropriate cell substrate.[35]

In one embodiment, the peptide bioinks provided in the present disclosure may be used for printing different cell-laden 3D constructs. In one preferred embodiment, cell-laden cuboids with 10 mm edges and 2.6 mm height are printed. In another preferred embodiment, cell-laden cylinders with 10 mm diameter, 1-2 mm wall thickness, and 10 mm height are printed.

Figure 21:
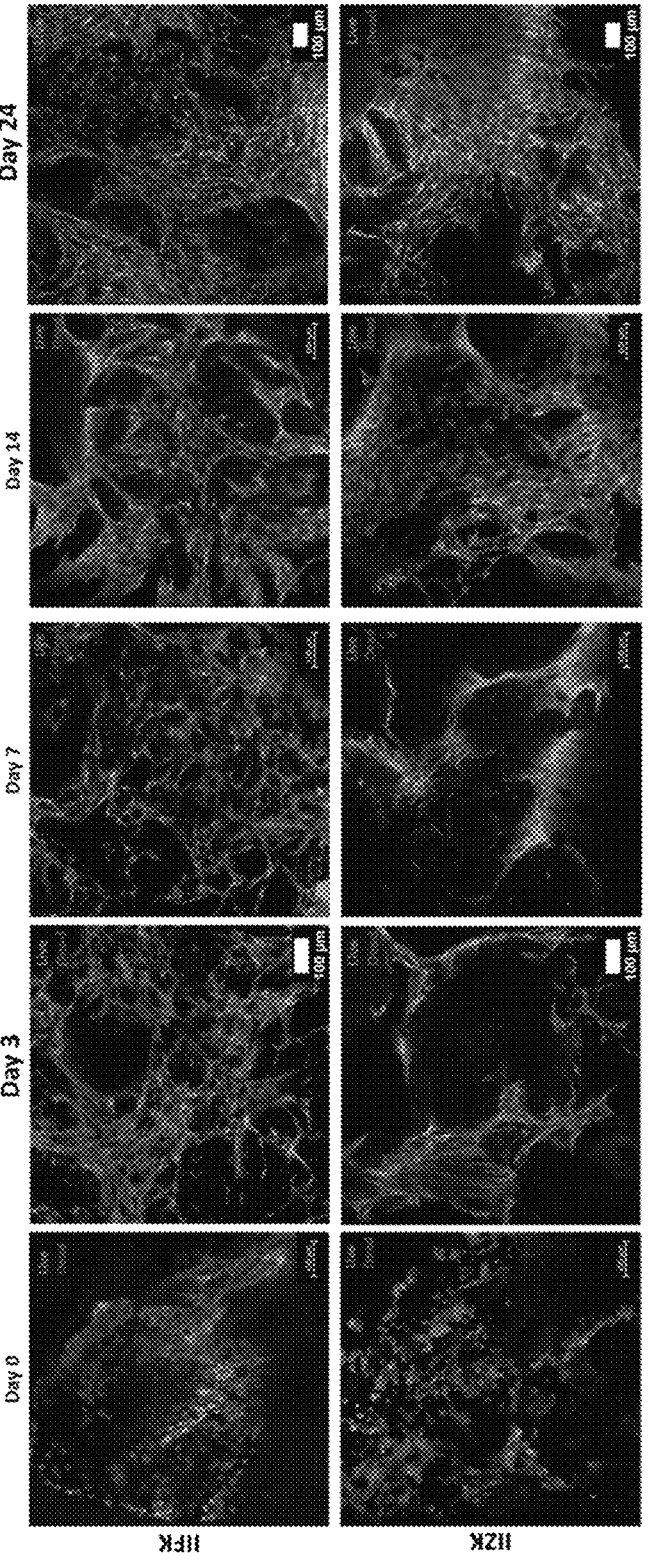
FIG. 21 is a graph showing the cell viability of hDFn within IIFK (SEQ ID NO: 1) and IIZK (SEQ ID NO: 9) peptide hydrogels on different days according to an exemplary embodiment of the present disclosure.
Figure 22:
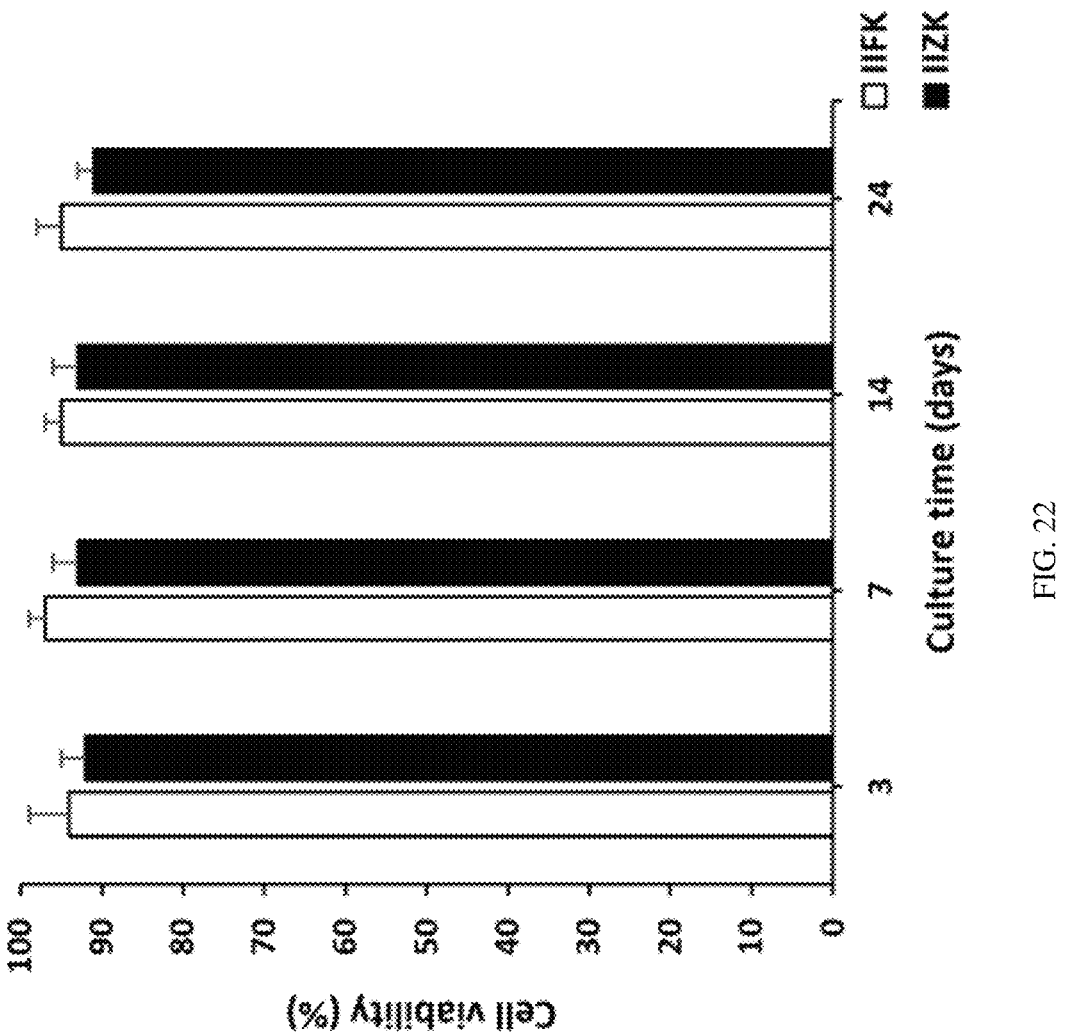
FIG. 22 is a graph showing the percentage cell viability of hDFn within IIFK (SEQ ID NO: 1) and IIZK (SEQ ID NO: 9) peptide hydrogels according to an exemplary embodiment of the present disclosure.

The results of cell-laden cuboids show a high percentage of cell viability (>90%) immediately after bioprinting (day 0), which is also preserved over time up to 24-day (FIG. 21 and FIG. 22). This maintained rate is either better or comparable to other bioinks such as GelMA [40], alginate/nanocellulose [41], and KCA-nanosilicate.[42] Using IIFK (SEQ ID NO: 1) peptide, no there is no difference in cell viability between the center and the edge of the filled cube structure. As for IIZK (SEQ ID NO: 9) and IZZK (SEQ ID NO: 25), cell viability in the center of the structure is slightly lower as compared to the edges, respectively.

Having described the many embodiments of the present disclosure in detail, it will be apparent that modifications and variations are possible without departing from the scope of the invention defined in the appended claims. Furthermore, it should be appreciated that all examples in the present disclosure, while illustrating many embodiments of the invention, are provided as non-limiting examples and are, therefore, not to be taken as limiting the various aspects so illustrated.

EXAMPLES

Example 1

Peptide Design

Three peptide sequences have been designed to demonstrate the novel features of the class of the inventive peptides; this includes Ac-Ile-Ile-Phe-Lys-NH$_2$ (IIFK (SEQ ID NO: 1)), Ac-Ile-Ile-Cha-Lys-NH$_2$ (IIZK (SEQ ID NO: 9)), and Ac-Ile-Cha-Cha-Lys-NH$_2$ (IZZK (SEQ ID NO: 25)). These peptides are a category of amphiphilic peptide composed of a hydrophilic headgroup at the C-terminus and a hydrophobic block at N-terminus. At the C-terminus lysine, a positively charged residue is chosen to increase the peptide solubility in water. For IIFK (SEQ ID NO: 1), the hydroaphobic block contained three hydrophobic amino acids; the most hydrophobic residue (Ile) is placed the first at the N-terminal, followed by another Ile and Phe. Besides the hydrophobicity, the Phe is chosen to investigate further the role of stacking interaction of the aromatic side-chain in the self-assembly process. In addition, IIZK (SEQ ID NO: 9) and IZZK (SEQ ID NO: 25) that have the cyclohexylalanine (Cha) residue in the middle of the peptide sequence are designed, which is in comparison to Phe, a more hydrophobic and ring-shaped amino acid, but not aromatic. All peptides are amidated and acetylated at the C-terminus and N-terminus, respectively, to neutralize the charge effects from both terminals.

Example 2

Peptide Synthesis and Purification

Ac-Ile-Ile-Phe-Lys-NH$_2$ (IIFK (SEQ ID NO: 1)), Ac-Ile-Ile-Cha-Lys-NH$_2$ (IIZK (SEQ ID NO: 9)), and Ac-Ile-Cha-Cha-Lys-NH$_2$ (IZZK (SEQ ID NO: 25)) peptides are synthesized by solid-phase peptide synthesis (SPPS) using CS136X CS Biopeptide synthesizer. The peptide coupling is conducted on rink amide resin by aging the resin in a mixture of TBTU (3 eq.), HOBt (3 eq.) DIPEA (6 eq.), and Fmoc-protected amino acid (3 eq.). Piperidine/DMF with concentration of 20% (v/v) is used to deprotect the fmoc group on the N-terminus of the peptide sequence to continue to the next coupling step. After coupling the last amino acid to the peptide sequence on the resin, the sequence is capped with an acetyl group. All of those steps are conducted inside the synthesizer. The resin is then transferred out of the synthesizer and cleaved with an acidic solution of TFA, TIS, and water for a minimum of 2 hrs. The peptide is subsequently collected in a round bottom flask. Afterward, cold diethyl ether is added to further induce peptide precipitation and left standing overnight at 4° C. The precipitated peptide is separated from the supernatant by centrifugation and kept in a vacuum desiccator for drying. The collected peptides are purified using Agilent 1260 Infinity Prep-HPLC with Zorbax® PrepHT SB-C18 column for 12 minutes at the flow rate of 20 mL/min. Milli-Q® water and Acetonitrile containing 0.1% formic acid are used as mobile phases. The purity of the peptides is further analyzed by analytical LC-MS and NMR.

Example 3

Liquid Chromatography-Mass Spectroscopy (LC-MS)

1 mg/ml of the peptide in water are analyzed using Agilent 1260 Infinity LC equipped with Agilent 6130 Quadrupole MS. Agilent Zorbax® SB-C18 4.6×250 mm column is used together with a mixture of two different solutions of 0.1% (v/v) formic acid-water (A) and 0.1% (v/v) formic acid-acetonitrile (B). The flow of the mobile phase is 1.5 mL/min, with a composition of 98% A-2% B in the first 30 seconds. From 0.5 to 16.5 mins, the flow of B increased to 98% B and turned back again to 2%. LC chromatogram is obtained at a wavelength of 220 nm. The molecular weight of the peptides is confirmed by electrospray ionization mass spectrometry in positive mode.

Example 4

1D Nuclear Magnetic Resonance 1D (1H and 13C) NMR spectra of all purified peptide are recorded using Bruker Avance III 500 MHz NMR spectrometer equipped with a cryoprobe. The samples are prepared by dissolving 5 mg peptide powder in 700 µL of d6-DMSO, which are then transferred into an NMR tube.

Example 5

Peptide Gelation Studies

The peptide powder is dissolved in 0.90 mL of Milli-Q® water and vortexed until a clear and homogeneous solution is observed. Then 0.10 mL of 10×PBS buffer (w/o Ca$^{2+}$ and Mg$^{2+}$) is added to the peptide solution. The glass vial is kept undisturbed, and the hydrogel formation is observed using the vial inversion method. The time and minimum concentration at which each peptide has formed a hydrogel are noted.

Example 6

2D (TOCSY and NOESY) NMR and 1H NMR

Spectra are acquired on a Bruker Avance III 600 Mhz equipped with a 5 mm Z-gradient SmartProbe® BB (F)-H-D. The NMR samples are prepared by dissolving the peptide in a mixture of 900 µL of 1 mM sodium trimethylsilylpropanesulfonate (DSS) and 100 µL of D$_2$O. First, 1H-NMR is scanned for 32 scans using a pulse program of zgesgp and water suppression using excitation sculpting with gradients.[1] The chemical shift of each proton is then assigned from TOCSY acquisition that is conducted with the time domain of 2048 (F2)×512 (F1), 16 number of scans, a pulse program of cosydfgpph19, and water suppression using Mar. 9, 2019 pulse sequence.[2-4] NOESY acquisition is performed with a time-domain size of 2048 (F2)×512 (F1), 24 scan numbers, a pulse program of noesyesgpph 19, a mixing time of 400 ms, and water suppression using Mar. 9, 2019 pulse sequence. Data processing is performed using Topspin® software.

Example 7

Circular Dichroism (CD)

CD spectra are measured at 25° C. using an AVIV-430 spectrophotometer equipped with a Peltier temperature controller. The peptide is dissolved in water without any buffer addition. Each peptide solution is then transferred into a demountable quartz cuvette with a path length of 0.1 mm. Samples are scanned at a wavelength from 190-300 nm with a spectral bandwidth of 1 nm and a scan speed of 1 nm/s. The voltage HT signal is monitored during the acquisition and kept below 800 V. When the voltage exceeded the limit, the measurement is repeated using the narrower cuvette (0.01 mm). The ellipticity signals are normalized to molar ellipticity [θ], according to the equation below:

$$[\theta] = \frac{100\,\theta}{C \times l}$$

[θ]: molar ellipticity (deg·cm$^2$·dmol$^{-1}$); θ: measured ellipticity (deg); C: peptide concentration (molar); l: cell path length (cm).

The secondary structure is then determined from the collected CD spectra using BestSel, a web server for secondary structure prediction.[5]

Example 8

Attenuated Total Reflection-Fourier Transform Infrared Spectroscopy (ATR-FTIR)

The secondary structure of the peptide is also determined using Thermo Scientific® Nicolet iS10 with Smart iTR diamond crystal. The spectra are recorded in the range of 4000-500 cm$^{-1}$ with a 1 cm$^{-1}$ interval.

Example 9

Raman Spectroscopy

Raman spectroscopy on IIFK (SEQ ID NO: 1), IIZK (SEQ ID NO: 9), and IZZK (SEQ ID NO: 25) is performed at 10 mg/ml concentration in 1×PBS buffer. The solution is allowed to gelate for 10 minutes, after which a small quantity is placed on a CaF$_2$ substrate and let to evaporate for ten minutes. Witec Alpha 300 RA confocal Raman spectrometer equipped with Andor® CCD camera (DU970N thermoelectrically cooled at −75° C.) is used to perform the Raman measurements in the backscattered configuration. The samples are excited through a 50× objective (Zeiss™ LD EC Epiplan-Neofluar) with linearly polarized 632.8 nm wavelength excitation laser (HeNe, High power laser, Research Electro-optics). Lasers' power is set at 1.5 mW, with an acquisition time of 10 or 20 seconds, according to the performance of the sample. Afterward, the spectra where the cosmic rays are removed, the baseline is subtracted with a polynomial of fif$^{th}$-order, and the signal intensity values are normalized to the 1445 cm$^{-1}$ peak. The three spectra are afterward averaged and compared. Several Voigt functions are fitted setting the peaks at 1653±3, 1663±3 and 1680±3 cm$^{-1}$, corresponding to α-helix, β-turn, and unordered β-turn. FWHM is kept at max to a value of 25, based on other studies[6] and after observing that the 1663 and 1680 peak in these samples never went above this value. Regions out of the Amide I area are introduced to improve the fitting performance, such as the peak at about 1580 and 1610 cm$^{-1}$ related to phenylalanine. A$_n$ additional peak at about 1635 cm$^{-1}$ is introduced in the fitting to include the water component, lysine, and isoleucine amino acid shifts.

Example 10

Atomic Force Microscopy (AFM)

The samples for the AFM measurement are prepared as follows; each peptide is dissolved in Milli-Q® water at a concentration of 10 mg/ml. After 24 hours, 20 μl of the solution is dropped on a freshly cleaved mica sheet and left to dry overnight under vacuum. The samples are measured the following day. AFM measurements are performed in air in a JPK Nanowizard III (Bruker) mounted on an inverted Olympus™ IX73 optical microscope. AFM probe OMCL-AC240TS-R3 (Olympus™) with a nominal resonance frequency of 70 kHz and a spring constant of 2 N/m is used in AC mode.

Example 11

Transmission Electron Microscopy (TEM)

The TEM samples are prepared by diluting peptide hydrogel in water. A drop of the diluted solution is added on a carbon-coated copper grid, treated with glow discharge plasma before being used. After 1 minute, the drop is blotted using filter paper. Subsequently, the grid is stained with 2% uranyl acetate for 30 seconds and then rinsed with water. The grid is allowed to dry for at least one day before imaging.

TEM images of peptide nanofibers are taken using FEI Titan G2 80-300 CT with a 300 kV emission gun. The protofilaments dimensions are retrieved from the 2D-FFT profile of random areas across the fibrils. (The average diameter of nanofibers are measured using ImageJ and Origin software from 100 fibers.)

Example 12

Scanning Electron Microscopy (SEM)

The SEM samples are prepared by dehydrating peptide hydrogels on a cover glass. The dehydration of peptide gel is done by immersing the gel in a gradually increasing ethanol concentration. The dehydrated gels that are immersed in 100% ethanol solution are then dried in a Tousimis Automegasamdri-916B series C Critical Point Dryer. The dried peptides are sputter-coated with 5 nm Ir before imaging. SEM images are taken using a FEI Magellan XHR Scanning Electron Microscope with an accelerating voltage of 3 kV.

Example 13

Viscoelastic Characterization of Peptide Hydrogels

The viscoelastic characteristics of peptide hydrogels, including the mechanical stiffness and viscosity, are analyzed using TA Ares-G2 Rheometer equipped with advanced Peltier system (APS). The mechanical stiffness of the peptide gels is measured using an 8 mm parallel plate with a gap of 1.8 mm, between the upper and lower plates, and at 22° C. The hydrogels are prepared, one day before the measurement, by mixing 135 μl of peptide solution, and 15 μl of 10×PBS inside a 9 mm internal diameter Sigmacote® coated glass casting ring. The rings are then kept inside Petri dishes at room temperature with water surrounding and tightly sealed to avoid dehydration. For each peptide, six replicates are prepared to control the accuracy of the measurements. The stiffness is analyzed through three successive tests, which are time-sweep, frequency-sweep, and amplitude-sweep. Time-sweep is first performed for 5 minutes with angular frequency and a strain of 1 rad/s and 0.1%, respectively. A frequency sweep is subsequently performed on the sample for a range of angular frequency of 0.1-100 rad/s with the same strain of 0.1%. The tests are completed with the amplitude sweep by applying a gradual increase of strain from 0.01% to 100% at 1 rad/s angular frequency.

The viscosity of the peptide solution before and after gelation is determined using the same rheometer, 25 mm parallel plate geometry, and a gap of 0.5 mm at 25° C. For the peptide solution, 250 μl of 13 mg/mL peptide solution is dropped on the Peltier plate and measured. For peptide gel samples, the peptide solution and 10×PBS buffer are mixed with the ratio of 1:10 on the Peltier plate and directly measured. The flow experiment is set up by starting the shear rate from 0.1 to 1500 s-1 for a 200-seconds duration. The value of the shear rate that we choose for our printing system is calculated using the equation below: 51

$$\gamma = \frac{8Q}{\pi d^3}$$

γ: shear rate (s−1); Q: flow rate (95 μL/s); d: diameter of needle (0.514 mm).

Example 14

Molecular Dynamics Simulation of Peptide Assembly

Molecular dynamics simulations of IIFK (SEQ ID NO: 1), IIZK (SEQ ID NO: 9), and IZZK (SEQ ID NO: 25) peptides in water are performed to study fiber formation on the atomic scale. Setups for simulation boxes are summarized in tables below.

| 2- peptide assembly: Ar-IIIEV Ala Ac-117It-RIH2 | | | |
|---|---|---|---|
| | Ac-IIFK (SEQ ID NO: 1)-NH$_2$ | Ac-IIZK (SEQ ID NO: 9)-NH$_2$ | Ac-IZZK (SEQ ID NO: 25)-NH$_2$ |
| Box size | 3.9 | 3.9 | 3.9 |
| Number of Water | 1718 | 1724 | 1715 |
| Number of Peptides | 2 | 2 | 2 |
| Net Charge in Peptide | 0 | 0 | 0 |
| Mole Fraction | 0.001 | 0.001 | 0.001 |
| Speed on Shaheen | 760 ns/1 day/ 512 cores | 760 ns/1 day/ 512 cores | 760 ns/1 day/ 512 cores |

| 4-peptide assembly: | | | |
|---|---|---|---|
| | Ac-IIFK (SEQ ID NO: 1)-NH$_2$ | Ac-IIZK (SEQ ID NO: 9)-NH$_2$ | Ac-IZZK (SEQ ID NO: 25)-NH$_2$ |
| Box size | 4.8 | 4.8 | 4.8 |
| Number of Water | 3531 | 3527 | 3530 |
| Number of Peptides | 4 | 4 | 4 |
| Net Charge in Peptide | 0 | 0 | 0 |
| Mole Fraction | 0.001 | 0.001 | 0.001 |
| Speed on Shaheen | 440 ns/1 day/ 512 cores | 440 ns/1 day/ 512 cores | 440 ns/1 day/ 512 cores |

| 60-peptide assembly: | | | |
|---|---|---|---|
| | Ac-IIFK (SEQ ID NO: 1)-NH$_2$ | Ac-IIZK (SEQ ID NO: 9)-NH$_2$ | Ac-IZZK (SEQ ID NO: 25)-NH$_2$ |
| Box size | 7.8 | 7.4 | 8.5 |
| Number of Water | 13622 | 11093 | 18076 |
| Number of Peptides | 60 | 60 | 60 |
| Net Charge in Peptide | 0 | 0 | 0 |
| Mole Fraction | 0.0045 | 0.0055 | 0.0033 |
| Speed on Shaheen | 130 ns/1 day/ 512 cores | 120 ns/1 day/ 512 cores | 120 ns/1 day/ 512 cores |

The simulation is conducted with an OPLS force-field,[52] parameters for the unnatural amino acid (Cha) are obtained by LigParGen webserver.[53] Water molecules are described using an SPC/E model. Simulations are conducted under GROMACS 2018.54 Systems are propagated at intervals of 2 fs. All trajectories are done in cubic periodic boundaries applied in all three directions. For efficiency, long-ranged non-bonded interactions are handled by the Particle Mesh Ewald Method;[55] electrostatic and Lennard-Jones interactions within 1.4 nm are considered short-ranged. Before the production simulation, the system had gone through energy minimization and equilibration steps under position and bond length restraints on heavy atoms. The final production run is handled as an isobaric-isothermic ensemble (NPT ensemble), and the system is coupled to a Berendsen Barostat[12] with reference pressure at 1 bar and a V-Rescale Thermostat[13] with reference temperature at 300 K. For all investigated peptides, the total simulation time is 100 ns. Calculations are performed on 512 Intel™ Haswell cores at 2.3 GHZ.

During the simulation, three cases are considered for each of the peptides; 2-peptides assembly, 4-peptides assembly, and 60-peptides assembly. The peptides are initially placed evenly in the simulation box and solvated with water, ten independent trajectories accumulating a simulation time of 1 us for each kind of case are attempted.

2-peptides assembly and 4-peptides assembly correspond to a diluted situation where peptide to water mole fraction is 0.001, which allows the study of the pair formation and local assembly behavior.

Example 15

Printer Setup and Parameter Optimization

The bioprinting experiments are conducted with an in-house developed robotic 3D bioprinter. The printer components included a five degrees-of-freedom robotic arm, a custom-designed coaxial nozzle, microfluidic pumps, and a heated bed. The robotic arm is interfaced with Repetier-Host to slice files into gcode for 3D printing, and printing files are designed in SolidWorks®. The coaxial nozzle is fabricated to house three inlets and a single outlet, with a final inner diameter of 0.5 mm. The commercial microfluidic pumps are controlled simultaneously during printing through a graphical user interface. Different printing parameters are investigated, including; peptide and PBS concentration, pump flow rates, printing speed, and line space. The optimal peptide concentration is set to 13 mg/mL for all three peptides. A concentration of 7×PBS is used for the gelation of all three peptides. The heatbed is set to 37 C. The pump flow rates are optimized at a range of 55-60 µl/min for peptide, 15-20 µl/min for PBS, and 10 µl/min for cells.

Example 16

Printability and Shape Fidelity Assessment

The three peptides, IIFK (SEQ ID NO: 1), IZZK (SEQ ID NO: 25), and IIZK (SEQ ID NO: 9), are compared for printability and shape fidelity. For bioprinting, three solutions are prepared-peptide hydrogel, phosphate buffer (PBS), and cells in 1×PBS. Each solution is dispensed into an individual inlet of the coaxial nozzle through the microfluidic pumps. Each of the three peptides, IIFK (SEQ ID NO: 1), IIZK (SEQ ID NO: 9), and IZZK (SEQ ID NO: 25), are weighed out as 13 mg/ml. Immediately before printing, the selected peptide is dissolved in Milli-Q® water and loaded in Pump 1. A solution of 7×PBS is loaded in Pump 2. A solution of 1×PBS is loaded in Pump 3. Flow rates of the microfluidic pumps are optimized at a range of 55-60 µl/min for Pump 1, 15-20 µl/min for Pump 2, and 10 µl/min for Pump 3. The flow rates are adjusted within the optimized range, depending on the viscosity of the peptide being used. Four structures are designed in SolidWorks®, converted into g-code and bioprinted. The structures included a filled cube (10×10×1.5 mm), a hollow cylinder (10×10×10 mm), and a baby-size human nose. samples are Multiple printed for each shape to assess shape fidelity. Print resolution, refinement of details, and heights of the samples are compared. A rubric for fidelity assessment is developed to examine printed constructs. The best quality constructs are expected to have excellent resolution, visibly refined details, a consistent thread of gel without any gaps within layers, and to hold shape with taller structures without sagging due to excess water. Imperfect quality constructs had signs of sagging, clumpy deposits of gel, low-resolution shapes, and could not define structure details.

Example 17

Filament Collapse Test

A small platform is designed in SolidWorks® consisting of multiple cubes 3D printed on to a solid base and spaced apart at different lengths: 1, 2, 4, 8, and 16 mm. The platform is 3D printed in PLA material at a fill density of 100% to create a stable base. Each of the three peptides-IIFK (SEQ ID NO: 1), IIZK (SEQ ID NO: 9), and IZZK (SEQ ID NO: 25)—are extruded from the coaxial nozzle as the robotic arm moved from one end of the platform to the other. The deposited thread of gel is examined for any signs of sagging.

Example 18

Cell Culture

The biocompatibility of the peptide biomaterials is tested using three different cell types. Those are human neonatal dermal fibroblasts (hDFn). hDFn is a kind gift from Professor Abdalla Awidi at The University of Jordan/Cell Therapy Center in Jordan. Cells at passages 4-7 are used in cell culture experiments. The study is approved by the Institutional Biosafety and Bioethics Committee (IBEC) and the Institutional Animal Care and Use Committee (IACUC) at King Abdulla University of Science and Technology (KAUST).

For all 3D cell culture experiments, the minimum gelation concentration of IIZK (SEQ ID NO: 9) (1 mg/ml) and IIFK (SEQ ID NO: 1) (2 mg/ml) peptides are used. Before its use in 3D cell culture experiments, peptides powder is sterilized using the UV light for 30 minutes.

Example 19

3D Culture of hDFn

To establish 3D cell culture, first, peptide base coating of cell culture wells is performed, by adding IIFK (SEQ ID NO: 1) or IIZK (SEQ ID NO: 9) peptide dissolved in cell culture grade water and then adding PBS at a final concentration of 1×. The plates are then incubated for 15 minutes at 37° C. until the hydrogels are formed. Subsequently, the 3D cell construct is prepared by adding a peptide solution in cell culture grade water on top of the peptide base and then mixing it gently by swirling with cells in 1×PBS. Alternatively, 100 μl 3D constructs in the 96-well plate are formed by mixing the peptide solution with cells suspended in PBS. Culture plates are incubated for 10 minutes at 37° C., and complete media is added carefully to the culture plates.

For hDFn, the culture media consisted of DMEM/high-glucose supplemented with Glutamax, 10% FBS, and 1% Penicillin/streptomycin (all from GIBCO®, ThermoFisher®, USA). The seeding density of the cells is $20 \times 10^3$ cells/well in 96 wells plate, and $40 \times 10^3$ cells/well 48 wells plate. Three biological replicates are used, with each including 3-4 technical replicates. For comparison purposes, controls included 2D culture and 3D cultured cells in 3 mg/ml Matrigel.

Example 20

Cell Viability Testing

The viability of 3D cultured cells is assessed using the LIVE/DEAD Viability/Cytotoxicity Kit (ThermoFisher®, USA). In which, calcein acetoxymethyl ester (Calcein-AM) is used to detect viable cells and ethidium homodimer-I (EthD-I) is used to detect dead cells. Cell-laden 3D constructs are washed twice with dulbecco's phosphate-buffered saline (D-PBS). Then a staining solution of 2 μM of Calcein-AM and 4 μM of EthD-1 are added to the 3D cell-laden constructs and incubated for 30 minutes at room temperature. After the incubation period, the staining solution is discarded, and 1×DPBS is added to each well before imaging. Stained cells are imaged with an inverted confocal microscope (Zeiss™ LSM 710 Inverted Confocal Microscope, Germany) or ZEISS™ fluorescent microscope. The Viability of HDFn is assessed after 24 hours, 4, and 7 days.

Example 21

Cell Proliferation Assessment

The CellTiter-Glo® luminescent 3D cell viability assay is used to determine the proliferation rate of the cells in 3D peptide hydrogel in comparison to controls. This assay relies on ATP quantitation via measuring luminescent signal produced from metabolically active cells in the presence of thermostable luciferase. The intensity of the signal produced is directly proportional to the amount of ATP present.[59] The protocol is done following the manufacturer's recommendations. A volume of the CellTiter-Glo® 3D reagent equivalent to that of the cell culture medium is added to each well and thoroughly mixed for 5 minutes. The cell culture plates are then incubated for 30 minutes at room temperature and read using a plate reader (PHERAstar® FS, Germany). The metabolic activity of HDFn is assessed after 24 hours, 4, and 7 days.

Example 22

Karyotyping of 3D Cultured hDFn Cells

In order to assess possible genomic instability due to 3D culturing of cells in peptide hydrogel, karyotyping is performed on hDFn 3D cultured in IIFK (SEQ ID NO: 1) and IIZK (SEQ ID NO: 9) peptide hydrogel for 7 days using standard protocols.[16, 17] hDFn cells cultured in 2D are used as a control. Briefly, after 3D culture, cells are collected and arrested at the metaphase by incubation with Colcemid. Cells are then treated with a hypotonic solution to preserve their state, followed by the addition of a fixative solution (methanol: glacial acetic acid) (3:1). Harvested cells are then dropped in the middle of a glass slide and subsequently dried/aged overnight at 56° C. G-banding is performed using trypsin and Leishman staining and analyzed using the Cyto Vision® platform and its associated software (Leica®).

Example 23

Cytoskeleton Staining

Rhodamine Phalloidin (Invitrogen®, ThermoFisher®, USA) is used for the staining of F-Actin (ex/em~540 nm/~565 nm) in hDFn. Culture media is removed, and cells are washed with 1×DPBS then fixed using 4% methanol free formaldehyde (Thermofisher®, USA) for 30 minutes. Cells are subsequently washed one more time with 1×DPBS after discarding the fixative solution followed by a 5 minutes incubation in pre-chilled cytoskeleton buffer containing 3 mM $MgCl^2$, 300 mM sucrose and 0.5% Triton X-100 in PBS solution. Cells are then incubated for 30 minutes at room temperature in blocking buffer containing 5% FBS, 0.1% Tween-20, and 0.02% Sodium Azide in 1×PBS. Rhodamine-Phalloidin diluted 1:40 in 1×PBS is added to each well after discarding the blocking buffer and incubated for 1 hour at room temperature. Cells are then washed with 1×PBS and incubated for 5 minutes with 1:2000 diluted 4',6-diamidino-2-phenylindole (DAPI) in sterile water. Images are acquired using a laser scanning confocal microscope (Zeiss™ LSM 880 Inverted Confocal Microscope, Germany).

Example 24

Cell Migration Assay (Fibrin Drop Assay)

A three-dimensional cell-migration assay is performed to evaluate the cellular behavior in IIFK (SEQ ID NO: 1) and IIZK (SEQ ID NO: 9) peptide hydrogel. The assay is performed as described previously by first forming a cell-loaded fibrin clot and then embedding it within the peptide hydrogel. To form a cell-loaded fibrin clot fibrinogen is diluted up to 2 mg/ml in PBS, and then cells are added to a final concentration of $60 \times 10^3$ per 2 μl fibrinogen. Drops of 2 μl fibrinogen and cells are placed in a tissue culture plate, and then thrombin is added to a final concentration of 0.25 unit/ml. The drops are left to polymerize for 15 minutes in the $CO_2$ incubator and then embedded within IIFK (SEQ ID NO: 1) and IIZK (SEQ ID NO: 9) peptide hydrogel. Complete media are added gently, and cultures are kept in the $CO_2$ incubator until analyzed. Cells are imaged by an inverted phase-contrast microscopy and laser scanning confocal microscope (Zeiss™ LSM 880 Inverted Confocal Microscope, Germany).

Example 25

Bioprinting of Cell-Laden Constructs hDF is used in bioprinting experiments. Each cell type is cultured in its complete growth media, as described before, and cells at passages 4-8 are used in printing experiments. For bioprinting, hDF is mixed with PBS at a final concentration of $5 \times 10^6$ and $8 \times 10^6$ cells/ml, respectively, and loaded into the microfluidic tubing of the robotic arm bioprinter. In the printing process, the flow rates are 10 μl/min, 55 μl/min, and 8 μl/min for cells, peptide solution, and 5×PBS, respectively. Different cell-laden structures are printed including cuboids with 10 mm edges and 2.6 mm height, and cylinders with 10 mm diameter, and a height of 10 mm. After printing, the printed cell-laden constructs are placed in the $CO_2$ incubator for 5 min before the addition of complete growth media. The printed cell-laden constructs are placed in standard conditions (37° C., 5% $CO_2$, and 95% relative humidity), and the media are changed every three days.

Example 26

Characterization of Bioprinted Constructs

LIVE/DEAD® Cell Viability/Cytotoxicity Kit (ThermoFisher®, USA) is used to assess the viability of cells within the 3D printed constructs. The same protocol, as described earlier, is followed except for increasing the incubation time to 1 hour. The viability of cells is assessed immediately after printing, within 1 hour, designated as day 0 and at days 3, 7, 17 and 24 post-printing. For each time point, two cell-laden constructs are analyzed, and images are taken from different areas of the construct, including the center, edges, top, and bottom. Stained printed cell-laden constructs are imaged using an inverted laser scanning confocal microscope (Zeiss™ LSM 880 Inverted Confocal Microscope, Germany). The number of live and dead cells are counted using imageJ software, and the percentage of cell viability is calculated as the average ratio of live to total cells.

For observation of cell morphology, and evaluating the 3D distribution of cells and cell-matrix interaction post bioprinting, immunofluorescent staining of the cytoskeleton is performed. The same protocol, as described earlier, is performed. Z-stack images are acquired using an inverted laser scanning confocal microscope (Zeiss™ LSM 880 Inverted Confocal Microscope, Germany), and 3D image reconstruction is performed using Imaris software.

For chondrogenic differentiated constructs, immunofluorescent staining of collagen II is performed. Briefly, hydrogel sections are fixed with 4% paraformaldehyde (ThermoFisher®, USA) for 45 minutes and then permeabilized with 0.5% Triton X-100 for 20 minutes, and blocked with blocking buffer (5% FBS, 0.1% Tween-20, and 0.02% Sodium Azide) for 30 minutes at room temperature. Constructs are then incubated with rabbit anti-human Collage II (Invitrogen®, ThermoFisher®, USA) overnight at 4° C. followed by incubation with anti-rabbit Alexa® Fluor 555 secondary (Invitrogen,® ThermoFisher®, USA) antibody for 2 hours at room temperature and counterstained with DAPI for 5 minutes at room temperature. Controls with only secondary antibodies are also performed. Images are acquired using a fluorescent microscope (Zeiss™, Germany). For histological analysis, proteoglycan is stained by Alcian blue and observed by light microscopy (Zeiss™, Germany)

It is intended that the invention not be limited to the particular embodiment disclosed herein contemplated for carrying out this invention, but that the invention will include all embodiments falling within the scope of the claims.

All documents, patents, journal articles and other materials cited in the present application are incorporated herein by reference.

The many features and advantages of the invention are apparent from the detailed specification, and thus, it is intended by the appended claims to cover all such features and advantages of the invention which fall within the true spirit and scope of the invention. Further, since numerous modifications and variations will readily occur to those skilled in the art, it is not desired to limit the invention to the exact construction and operation illustrated and described, and accordingly, all suitable modifications and equivalents may be resorted to, falling within the scope of the invention.

REFERENCES

The following references are referred to above and are incorporated herein by reference:

1. Gungor-Ozkerim, P. S.; Inci, I.; Zhang, Y. S.; Khadem-hosseini, A.; Dokmeci, M. R. *Biomaterials Science* 2018, 6, (5), 915-946.
2. Donderwinkel, I.; van Hest, J. C. M.; Cameron, N. R. *Polymer Chemistry* 2017, 8, (31), 4451-4471.
3. Gopinathan, J.; Noh, I. *Biomater Res* 2018, 22, 11-11.
4. Khademhosseini, A.; Camci-Unal, G., 3*D Bioprinting in Regenerative Engineering: Principles and Applications.* CRC Press: 2018.
5. Gjorevski, N.; Sachs, N.; Manfrin, A.; Giger, S.; Bragina, M. E.; Ordonez-Moran, P.; Clevers, H.; Lutolf, M. P. *Nature* 2016, 539, (7630), 560-564.
6. Hauser, C. A. E.; Deng, R.; Mishra, A.; Loo, Y.; Khoe, U.; Zhuang, F.; Cheong, D. W.; Accardo, A.; Sullivan, M. B.;

Riekel, C.; Ying, J. Y.; Hauser, U. A. *Proceedings of the National Academy of Sciences* 2011, 108, (4), 1361-1366.

7. Loo, Y.; Lakshmanan, A.; Ni, M.; Toh, L. L.; Wang, S.; Hauser, C. A. E. *Nano Letters* 2015, 15, (10), 6919-6925.

8. Seow, W. Y.; Salgado, G.; Lane, E. B.; Hauser, C. A. E. *Scientific Reports* 2016, 6, 32670.

9. Chan, K. H.; Xue, B.; Robinson, R. C.; Hauser, C. A. E. *Scientific Reports* 2017, 7, (1), 12897.

10. Wang, H.; Ren, C.; Song, Z.; Wang, L.; Chen, X.; Yang, Z. *Nanotechnology* 2010, 21, (22), 225606.

11. Raeburn, J.; Pont, G.; Chen, L.; Cesbron, Y.; Lévy, R.; Adams, D. J. *Soft Matter* 2012, 8, (4), 1168-1174.

12. Betush, R. J.; Urban, J. M.; Nilsson, B. L. *Peptide Science* 2018, 110, (1), e23099.

13. Lakshmanan, A.; Cheong, D. W.; Accardo, A.; Di Fabrizio, E.; Riekel, C.; Hauser, C. A. *Proc Natl Acad Sci USA* 2013, 110, (2), 519-24.

14. Bowerman, C. J.; Ryan, D. M.; Nissan, D. A.; Nilsson, B. L. *Molecular BioSystems* 2009, 5, (9), 1058-1069.

15. Senguen, F. T.; Lee, N. R.; Gu, X.; Ryan, D. M.; Doran, T. M.; Anderson, E. A.; Nilsson, B. L. *Molecular BioSystems* 2011, 7, (2), 486-496.

16. Surewicz, W. K.; Mantsch, H. H.; Chapman, D. *Biochemistry* 1993, 32, (2), 389-394.

17. Goormaghtigh, E.; Cabiaux, V.; Ruysschaert, J.-M. *European Journal of Biochemistry* 1990, 193, (2), 409-420.

18. Williams, R. W.; Dunker, A. K. *Journal of Molecular Biology* 1981, 152, (4), 783-813.

19. Rivas-Arancibia, S.; Rodríguez-Martínez, E.; Badillo-Ramírez, I.; López-González, U.; Saniger, J. M. *Frontiers in Molecular Neuroscience* 2017, 10, (137).

20. Seow, W. Y.; Salgado, G.; Lane, E. B.; Hauser, C. A. E. *Scientific Reports* 2016, 6.

21. Tuncaboylu, D. C.; Argun, A.; Sahin, M.; Sari, M.; Okay, O. *Polymer* 2012, 53, (24), 5513-5522.

22. Murphy, S. V.; Atala, A. *Nature Biotechnology* 2014, 32, (8), 773-785.

23. Grinnell, F. *Trends in cell biology* 2003, 13, (5), 264-269.

24. Franco-Barraza, J.; Beacham, D. A.; Amatangelo, M. D.; Cukierman, E. *Current protocols in cell biology* 2016, 71, (1), 10.9. 1-10.9. 34.

25. Seliktar, D. *Science* 2012, 336, (6085), 1124-1128.

26. Baker, B. M.; Chen, C. S. *Journal of cell science* 2012, 125, (13), 3015-3024.

27. Even-Ram, S.; Yamada, K. M. *Current opinion in cell biology* 2005, 17, (5), 524-532.

28. Lutolf, M. P.; Lauer-Fields, J. L.; Schmoekel, H. G.; Metters, A. T.; Weber, F. E.; Fields, G. B.; Hubbell, J. A. *Proceedings of the National Academy of Sciences* 2003, 100, (9), 5413-5418.

29. Mazzeo, M. S.; Chai, T.; Daviran, M.; Schultz, K. M. *ACS applied bio materials* 2018, 2, (1), 81-92.

30. Discher, D. E.; Mooney, D. J.; Zandstra, P. W. *Science* 2009, 324, (5935), 1673-1677.

31. Engler, A. J.; Sen, S.; Sweeney, H. L.; Discher, D. E. *Cell* 2006, 126, (4), 677-689.

32. Chaudhuri, O.; Gu, L.; Klumpers, D.; Darnell, M.; Bencherif, S. A.; Weaver, J. C.; Huebsch, N.; Lee, H.-p.; Lippens, E.; Duda, G. N. *Nature materials* 2016, 15, (3), 326-334.

33. Dalby, M. J.; Gadegaard, N.; Tare, R.; Andar, A.; Riehle, M. O.; Herzyk, P.; Wilkinson, C. D.; Oreffo, R. O. *Nature materials* 2007, 6, (12), 997-1003.

34. Haugh, M. G.; Vaughan, T. J.; Madl, C. M.; Raftery, R. M.; McNamara, L. M.; O'Brien, F. J.; Heilshorn, S. C. *Biomaterials* 2018, 171, 23-33.

35. Silbernagel, N.; Körner, A.; Balitzki, J.; Jaggy, M.; Bertels, S.; Richter, B.; Hippler, M.; Hellwig, A.; Hecker, M.; Bastmeyer, M. *Biomaterials* 2020, 227, 119551.

36. Darnell, M.; Gu, L.; Mooney, D. *Biomaterials* 2018, 181, 182-188.

37. Kahin, K.; Khan, Z.; Albagami, M.; Usman, S.; Bahnshal, S.; Alwazani, H.; Majid, M.; Rauf, S.; Hauser, C. In *Development of a robotic 3D bioprinting and microfluidic pumping system for tissue and organ engineering*, Microfluidics, BioMEMS, and Medical Microsystems XVII, 2019; International Society for Optics and Photonics: p 108750Q.

38. Mouser, V. H. M.; Melchels, F. P. W.; Visser, J.; Dhert, W. J. A.; Gawlitta, D.; Malda, *J. Biofabrication* 2016, 8, (3), 035003.

39. Chimene, D.; Peak, C. W.; Gentry, J. L.; Carrow, J. K.; Cross, L. M.; Mondragon, E.; Cardoso, G. B.; Kaunas, R.; Gaharwar, A. K. *ACS Applied Materials & Interfaces* 2018, 10, (12), 9957-9968.

40. Bertassoni, L. E.; Cardoso, J. C.; Manoharan, V.; Cristino, A. L.; Bhise, N. S.; Araujo, W. A.; Zorlutuna, P.; Vrana, N. E.; Ghaemmaghami, A. M.; Dokmeci, M. R. *Biofabrication* 2014, 6, (2), 024105.

41. Markstedt, K.; Mantas, A.; Tournier, I.; Martínez Ávila, H. c.; Hagg, D.; Gatenholm, P. *Biomacromolecules* 2015, 16, (5), 1489-1496.

42. Wilson, S. A.; Cross, L. M.; Peak, C. W.; Gaharwar, A. K. *ACS applied materials & interfaces* 2017, 9, (50), 43449-43458.

43. Bernal, P. N.; Delrot, P.; Loterie, D.; Li, Y.; Malda, J.; Moser, C.; Levato, R. *Advanced materials* 2019, 31, (42), 1904209.

44. Kang, H.-W.; Lee, S. J.; Ko, I. K.; Kengla, C.; Yoo, J. J.; Atala, A. *Nature biotechnology* 2016, 34, (3), 312.

45. Hwang, T. L.; Shaka, A. J. *Journal of Magnetic Resonance, Series A* 1995, 112, (2), 275-279.

46. Derome, A. E.; Williamson, M. P. *Journal of Magnetic Resonance* (1969) 1990, 88, (1), 177-185.

47. Piotto, M.; Saudek, V.; Sklenář, V. *Journal of Biomolecular NMR* 1992, 2, (6), 661-665.

48. Sklenar, V.; Piotto, M.; Leppik, R.; Saudek, V. *Journal of Magnetic Resonance, Series A* 1993, 102, (2), 241-245.

49. Micsonai, A.; Wien, F.; Kernya, L.; Lee, Y.-H.; Goto, Y.; Réfrégiers, M.; Kardos, J. Proceedings of the National Academy of Sciences 2015, 112, (24), E3095.

50. Maiti, N. C.; Apetri, M. M.; Zagorski, M. G.; Carey, P. R.; Anderson, V. E. *Journal of the American Chemical Society* 2004, 126, (8), 2399-2408.

51. Li, Z.; Huang, S.; Liu, Y.; Yao, B.; Hu, T.; Shi, H.; Xie, J.; Fu, X. *Scientific Reports* 2018, 8, (1), 8020.

52. Jorgensen, W. L.; Tirado-Rives, J. *Proceedings of the National Academy of Sciences of the U.S. Pat. No.* 2005, 102, (19), 6665.

53. Dodda, L. S.; Cabeza de Vaca, I.; Tirado-Rives, J.; Jorgensen, W. L. *Nucleic Acids Research* 2017, 45, (W1), W331-W336.

54. Abraham, M. J.; Murtola, T.; Schulz, R.; Páll, S.; Smith, J. C.; Hess, B.; Lindahl, E. *SoftwareX* 2015, 1-2, 19-25.

55. Darden, T.; York, D.; Pedersen, L. *The Journal of Chemical Physics* 1993, 98, (12), 10089-10092.

56. Berendsen, H. J. C.; Postma, J. P. M.; Gunsteren, W. F. v.; DiNola, A.; Haak, J. R. *The Journal of Chemical Physics* 1984, 81, (8), 3684-3690.

57. Bussi, G.; Donadio, D.; Parrinello, M. *The Journal of Chemical Physics* 2007, 126, (1), 014101.

33

34

58. Kim, Y. H.; Baek, N. S.; Han, Y. H.; Chung, M.-A.; Jung, S.-D. *Journal of neuroscience methods* 2011, 202, (1), 38-44.

59. Riss, T. L.; Valley, M. P.; Zimprich, C. A.; Niles, A. L.; Kupcho, K. R.; Lazar, D. F.

60. Howe, B.; Umrigar, A.; Tsien, F. *JoVE (Journal of Visualized Experiments)* 2014, (83), e50203.

61. Worton, R. G.; Duff, C., Karyotyping. In *Methods in enzymology*, Elsevier: 1979; Vol. 58, pp 322-344.

62. Perrier, A. L.; Tabar, V.; Barberi, T.; Rubio, M. E.; Bruses, J.; Topf, N.; Harrison, N. L.; Studer, L. *Proceedings of the National Academy of Sciences* 2004, 101, (34), 12543-12548.

63. Kang, J.; Lee, I. *Cardiovascular Pathology* 2006, 15, (4), 218-221.

2. Blakely, B. D.; Bye, C. R.; Fernando, C. V.; Horne, M. K.; Macheda, M. L.; Stacker, S. A.; Arenas, E.; Parish, C. L. *PloS one* 2011, 6, (3), e18373.

The foregoing applications, and all documents cited therein or during their prosecution ("appln cited documents") and all documents cited or referenced in the appln cited documents, and all documents cited or referenced herein ("herein cited documents"), and all documents cited or referenced in herein cited documents, together with any manufacturer's instructions, descriptions, products specifications, and product sheets for any products mentioned herein or in any document incorporated by reference herein, are hereby incorporated herein by reference, and may be employed in the practice of the invention. More specifically, all referenced documents are incorporated by reference to the same extent as if each individual document was specifically and individually indicated to be incorporated by reference.

While the present disclosure has been disclosed with references to certain embodiments, numerous modifications, alterations, and changes to the described embodiments are possible without departing from the sphere and scope of the present disclosure, as defined in the appended claims. Accordingly, it is intended that the present disclosure is not limited to the described embodiments, but that it has the full scope defined by the language of the following claims, and equivalents thereof.

---

What is claimed is:

1. An ultrashort peptide consisting of a sequence selected from the group consisting of:

(SEQ ID NO: 2)
IIFR (SEQ ID NO: 3)
IIFD (SEQ ID NO: 4)
IIFE (SEQ ID NO: 5)
LLFK (SEQ ID NO: 6)
LLFR (SEQ ID NO: 7)
LLFD (SEQ ID NO: 8)
LLFE (SEQ ID NO: 9)
IIZK (SEQ ID NO: 10)
IIZR (SEQ ID NO: 11)
IIZD (SEQ ID NO: 12)
IIZE (SEQ ID NO: 13)
LLZK (SEQ ID NO: 14)
LLZR (SEQ ID NO: 15)
LLZD (SEQ ID NO: 16)
LLZE (SEQ ID NO: 17)
IFFK (SEQ ID NO: 18)
IFFR (SEQ ID NO: 19)
IFFD (SEQ ID NO: 20)
IFFE (SEQ ID NO: 21)
LFFK (SEQ ID NO: 22)
LFFR (SEQ ID NO: 23)
LFFD (SEQ ID NO: 24)
LFFE (SEQ ID NO: 25)
IZZK (SEQ ID NO: 26)
IZZR

-continued (SEQ ID NO: 27)
IZZD (SEQ ID NO: 28)
IZZE (SEQ ID NO: 29)
LZZK (SEQ ID NO: 30)
LZZR (SEQ ID NO: 31)
LZZD (SEQ ID NO: 32)
LZZE (SEQ ID NO: 33)
FFIK (SEQ ID NO: 34)
ZZIR (SEQ ID NO: 35)
FFID (SEQ ID NO: 36)
FFIE (SEQ ID NO: 37)
FFLK (SEQ ID NO: 38)
FFLR (SEQ ID NO: 39)
FFLD (SEQ ID NO: 40)
FFLE (SEQ ID NO: 41)
ZZIK (SEQ ID NO: 42)
ZZIR (SEQ ID NO: 43)
ZZID (SEQ ID NO: 44)
ZZIE (SEQ ID NO: 45)
ZZLK (SEQ ID NO: 46)
ZZLR (SEQ ID NO: 47)
ZZLD (SEQ ID NO: 48)
ZZLE (SEQ ID NO: 49)
FIIK (SEQ ID NO: 50)
FIIR (SEQ ID NO: 51)
FIID (SEQ ID NO: 52)
FIIE (SEQ ID NO: 53)
FLLK -continued

```
                                       (SEQ ID NO: 55)
FLLD (SEQ ID NO: 56)
FLLE (SEQ ID NO: 57)
ZIIK (SEQ ID NO: 58)
ZIIR (SEQ ID NO: 59)
ZIID (SEQ ID NO: 60)
ZIIE (SEQ ID NO: 61)
ZLLK (SEQ ID NO: 62)
ZLLR (SEQ ID NO: 63)
ZLLD (SEQ ID NO: 64)
ZLLE (SEQ ID NO: 66)
ZZZK,
``` wherein I is isoleucine, L is leucine, F is phenylalanine, K is lysine, R is arginine, D is aspartic acid, E is glutamic acid, Z is cyclohexylalanine, wherein each of the sequences is connected to an acetylated or non-acetylated N-terminal protecting group, and may be amidated or non-amidated by a C-terminal protecting group, wherein the ultrashort peptide is capable of forming a gel by self-assembly, wherein the N-terminal protecting group is a peptidomimetic molecule, wherein the N-terminus of the peptidomimetic molecule may be modified with a functional group selected from the group consisting of: carboxylic acid, amide, alcohol, aldehyde, amine, imine, nitrile, an urea analog, phosphate, carbonate, sulfate, nitrate, maleimide, vinyl sulfone, azide, alkyne, alkene, carbohydrate, imide, peroxide, ester, aryl, ketone, sulphite, nitrite, phosphonate, and silane.

2. The ultrashort peptide recited in claim 1, wherein the amino acids in the peptide are either L-amino acids or D-amino acids.

3. The ultrashort peptide recited in claim 1, wherein the ultrashort peptide is capable of self-assembling into a hydrogel.

4. The ultrashort peptide recited in claim 1, wherein the ultrashort peptide is capable of self-assembling into an organogel.

5. The ultrashort peptide recited in claim 1, wherein the C-terminal protecting group is selected from the group consisting of: of small molecules, functional groups and linkers.

6. The ultrashort peptide recited in claim 1, wherein the C-terminal protecting group is selected from the group consisting of:

polar or non-polar functional groups;

—COOH, —COOR, —COR, —CONHR or —CONRR' with R and R' being selected from the group consisting of H, unsubstituted or substituted alkyls, and unsubstituted or substituted aryls;

—NH$_2$, —OH, —SH, —CHO, maleimide, imidoester, carbodiimide ester, isocyanate;

small molecules, comprising sugars, alcohols, hydroxy acids, amino acids, vitamins, or biotin;

linkers terminating in a polar functional group, comprising ethylenediamine, PEG, carbodiimide ester, or imidoester; and linkers coupled to small molecules or vitamins, comprising biotin, sugars, or hydroxy acids.

7. The ultrashort peptide recited in claim 1, being stable in aqueous solution at physiological conditions at ambient temperature for a period of time in the range from 1 day to at least 12 months.

8. A hydrogel comprising the ultrashort peptide recited in claim 1.

9. The hydrogel of claim 8, wherein the hydrogel is stable in aqueous solution at ambient temperature for a period of at least 1 month.

10. The hydrogel of claim 8, wherein the hydrogel is characterized by a loss factor tan δ (G"/G') in the range of 0.08 to 0.17.

11. The hydrogel of claim 8, wherein the hydrogel is characterized by a storage modulus G' from 1250 Pa to 300,000 Pa.

12. The hydrogel of claim 8, wherein the hydrogel has a higher mechanical strength than collagen or gelatin.

13. The hydrogel of claim 8, wherein the hydrogel is characterized by viscosity in the range of 0.4-0.6 Pa·s.

14. The hydrogel of claim 8, comprising fibers of the peptide of claim 1, the fibers defining a network that is capable of entrapping at least one of a microorganism, a virus particle, a peptide, a peptoid, a protein, a nucleic acid, an oligosaccharide, a polysaccharide, a vitamin, an inorganic molecule, a synthetic polymer, a micro- or nanoparticle, a small organic molecule or a pharmaceutically active compound.

15. The hydrogel of claim 8, wherein the hydrogel comprises at least one of a microorganism, a virus particle, a peptide, a peptoid, a protein, a nucleic acid, an oligosaccharide, a polysaccharide, a vitamin, an inorganic molecule, a synthetic polymer, a small organic molecule, a micro- or nanoparticle, or a pharmaceutically active compound entrapped by a network of fibers.

16. The hydrogel of claim 14, wherein the fibers are coupled to the at least one of a microorganism, a virus particle, a peptide, a peptoid, a protein, a nucleic acid, an oligosaccharide, a polysaccharide, a vitamin, an inorganic molecule, a synthetic polymer, a small organic molecule, a micro- or nanoparticle, or a pharmaceutically active compound entrapped by the network of fibers.

17. The hydrogel of claim 8, wherein the hydrogel is comprised in at least one of a fuel cell, a solar cell, an electronic cell, a biosensing device, a medical device, an implant, a pharmaceutical composition and a cosmetic composition.

18. The hydrogel of claim 8, which is injectable.

19. An organogel comprising the ultrashort peptide recited in claim 1.

20. The organogel of claim 19, wherein the hydrogel is stable in aqueous solution at ambient temperature for a period of at least 1 month.

21. The organogel of claim 19, wherein the hydrogel is characterized by a storage modulus G' from 1250 Pa to 300,000 Pa.

22. The organogel of claim 19, wherein the hydrogel has a higher mechanical strength than collagen or gelatin.

23. The organogel of claim 19, wherein the hydrogel is characterized by viscosity in the range of 0.4-0.6 Pa·s.

24. The organogel of claim 19, comprising fibers of the peptide of claim 1, the fibers defining a network that is capable of entrapping at least one of a microorganism, a virus particle, a peptide, a peptoid, a protein, a nucleic acid, an oligosaccharide, a polysaccharide, a vitamin, an inorganic molecule, a synthetic polymer, a micro- or nanoparticle, a small organic molecule or a pharmaceutically active compound.

25. The organogel of claim 19, wherein the hydrogel comprises at least one of a microorganism, a virus particle, a peptide, a peptoid, a protein, a nucleic acid, an oligosaccharide, a polysaccharide, a vitamin, an inorganic molecule, a synthetic polymer, a small organic molecule, a micro- or nanoparticle, or a pharmaceutically active compound entrapped by a network of fibers.

26. The organogel of claim 24, wherein the fibers are coupled to the at least one of a microorganism, a virus particle, a peptide, a peptoid, a protein, a nucleic acid, an oligosaccharide, a polysaccharide, a vitamin, an inorganic molecule, a synthetic polymer, a small organic molecule, a micro- or nanoparticle, or a pharmaceutically active compound entrapped by the network of fibers.

27. The organogel of claim 19, wherein the hydrogel is comprised in at least one of a fuel cell, a solar cell, an electronic cell, a biosensing device, a medical device, an implant, a pharmaceutical composition and a cosmetic composition.

28. The organogel of claim 19, which is injectable.

29. A method of preparing a hydrogel or organogel, the method comprising:
dissolving an ultrashort peptide recited in claim 1 in an aqueous solution or an organic solution, respectively.

30. The method of claim 29, wherein the dissolved peptide in aqueous or organic solution is further exposed to temperature, wherein the temperature is in the range from 20° C. to 90° C.

31. The method of claim 29, wherein the ultrashort peptide is dissolved at a concentration from about 0.01 µg/ml to 100 mg/ml.

32. The method of claim 29, wherein the ultrashort peptide is dissolved at a concentration from about 1 mg/ml to 50 mg/ml.

33. The method of claim 29, wherein the ultrashort peptide is dissolved at a concentration from about 1 mg/ml to about 20 mg/ml.

34. A wound dressing or wound healing agent comprising a hydrogel of claim 8.

35. A wound dressing or wound healing agent comprising an organogel of claim 19.

36. A surgical implant, or stent, the surgical implant or stent comprising a peptide scaffold, wherein the peptide scaffold is formed by a hydrogel of claim 8.

37. A surgical implant, or stent, the surgical implant or stent comprising a peptide scaffold, wherein the peptide scaffold is formed by an organogel of claim 19.

38. A pharmaceutical composition comprising the ultrashort peptide of claim 1.

39. The pharmaceutical composition of claim 38, further comprising a pharmaceutically active compound.

40. The pharmaceutical composition of claim 38, wherein the pharmaceutical composition is provided in the form of a topical gel or cream, a spray, a powder, or a sheet, patch or membrane.

41. The pharmaceutical composition of claim 38, wherein the pharmaceutical composition is provided in the form of an injectable solution, a topical gel or cream, a spray, a powder, or a sheet, patch or membrane.

42. A cosmetic composition comprising the ultrashort peptide of claim 1.

43. A biomedical device comprising the ultrashort peptide of claim 1.

44. An electronic device comprising the ultrashort peptide of claim 1.

45. A kit of parts, the kit comprising a first container with an ultrashort peptide of claim 1 and a second container with an aqueous or organic solution.

46. The kit of parts of claim 45, wherein the first container further comprises a pharmaceutically active compound.

47. The kit of parts of claim 45, wherein the second container further comprises a pharmaceutically active compound.

48. The kit of parts of claim 45, wherein the first container further comprises a pharmaceutically active compound and wherein the second container further comprises a pharmaceutically active compound.

49. An in vitro or in vivo method of tissue regeneration comprising the steps:
(a) providing a hydrogel of claim 8,
(b) exposing the hydrogel to cells which are to form regenerated tissue,
(c) allowing the cells to grow on the hydrogel.

50. The method of claim 49, which is performed in vivo, wherein, in step a), the hydrogel is provided at a place in a body where tissue regeneration is intended,
wherein the step a) is performed by injecting the hydrogel at a place in the body where tissue regeneration is intended.

51. An in vitro or in vivo method of tissue regeneration comprising the steps:
(a) providing an organogel of claim 19,
(b) exposing the organogel to cells which are to form regenerated tissue,
(c) allowing the cells to grow on the organogel.

52. The method of claim 51, which is performed in vivo, wherein, in step a), the organogel is provided at a place in a body where tissue regeneration is intended,
wherein the step a) is performed by injecting the organogel at a place in the body where tissue regeneration is intended.

53. A 2D or 3D cell culture substrate comprising a hydrogel of claim 8.

54. A 2D or 3D cell culture substrate comprising an organogel of claim 19.

55. An ultrashort peptide sequences containing repetitive sequences, the peptide having a general formula selected from:

$$A_nB_mX \text{ and } XB_mA_n$$

wherein the total number of amino acids of the ultrashort peptide does not exceed 7 amino acids;
wherein A is an aliphatic amino acids, selected from the group consisting of: isoleucine, leucine or any combination thereof, with n being an integer being selected from 0-5;
wherein B is comprised of at least one aromatic amino acid selected from the group consisting of: tyrosine, tryptophan, phenylalanine, hydrophobic amino acid phenylalanine, or comprised of a peptidomimetic amino acid that is the aliphatic counterpart of the aromatic amino acid;
wherein X is comprised of a polar amino acid, selected from the group consisting of: aspartic acid, glutamic acid, lysine, arginine, histidine, cysteine, serine, threo-
nine, asparagine, and glutamine.

56. The ultrashort peptide recited in claim 55, wherein the
peptide consists of a sequence selected from the group
consisting of:

```
                        (SEQ ID NO: 17)
IFFK
                        (SEQ ID NO: 18)
IFFR
                        (SEQ ID NO: 19)
IFFD
                        (SEQ ID NO: 20)
IFFE
                        (SEQ ID NO: 21)
LFFK
                        (SEQ ID NO: 22)
LFFR
                        (SEQ ID NO: 23)
LFFD
                        (SEQ ID NO: 24)
LFFE
```

66

```
-continued
                        (SEQ ID NO: 25)
IZZK
                        (SEQ ID NO: 26)
IZZR
                        (SEQ ID NO: 27)
IZZD
                        (SEQ ID NO: 28)
IZZE
                        (SEQ ID NO: 29)
LZZK
                        (SEQ ID NO: 30)
LZZR
                        (SEQ ID NO: 31)
LZZD
                        (SEQ ID NO: 32)
LZZE
``` wherein I is isoleucine, L is leucine, F is phenylalanine, K
is lysine, R is arginine, D is aspartic acid, E is glutamic
acid, Z is cyclohexylalanine,
wherein each of the sequences may be optionally con-
nected to an acetylated or non-acetylated N-terminal
protecting group, and may be amidated or non-ami-
dated by a C-terminal protecting group.

* * * * *

SEQUENCE LISTING

```
<160> NUMBER OF SEQ ID NOS: 66

<210> SEQ ID NO 1
<211> LENGTH: 4
<212> TYPE: PRT
<213> ORGANISM: Artificial Sequence
<220> FEATURE:
<223> OTHER INFORMATION: Synthetic

<400> SEQUENCE: 1

Ile Ile Phe Lys
1

<210> SEQ ID NO 2
<211> LENGTH: 4
<212> TYPE: PRT
<213> ORGANISM: Artificial Sequence
<220> FEATURE:
<223> OTHER INFORMATION: Synthetic

<400> SEQUENCE: 2

Ile Ile Phe Arg
1

<210> SEQ ID NO 3
<211> LENGTH: 4
<212> TYPE: PRT
<213> ORGANISM: Artificial Sequence
<220> FEATURE:
<223> OTHER INFORMATION: Synthetic

<400> SEQUENCE: 3

Ile Ile Phe Asp
1

<210> SEQ ID NO 4
<211> LENGTH: 4
<212> TYPE: PRT
<213> ORGANISM: Artificial Sequence
<220> FEATURE:
<223> OTHER INFORMATION: Synthetic

<400> SEQUENCE: 4

Ile Ile Phe Glu
```

1

```
<210> SEQ ID NO 5
<211> LENGTH: 4
<212> TYPE: PRT
<213> ORGANISM: Artificial Sequence
<220> FEATURE:
<223> OTHER INFORMATION: Synthetic

<400> SEQUENCE: 5

Leu Leu Phe Lys
1

<210> SEQ ID NO 6
<211> LENGTH: 4
<212> TYPE: PRT
<213> ORGANISM: Artificial Sequence
<220> FEATURE:
<223> OTHER INFORMATION: Synthetic

<400> SEQUENCE: 6

Leu Leu Phe Arg
1

<210> SEQ ID NO 7
<211> LENGTH: 4
<212> TYPE: PRT
<213> ORGANISM: Artificial Sequence
<220> FEATURE:
<223> OTHER INFORMATION: Synthetic

<400> SEQUENCE: 7

Leu Leu Phe Asp
1

<210> SEQ ID NO 8
<211> LENGTH: 4
<212> TYPE: PRT
<213> ORGANISM: Artificial Sequence
<220> FEATURE:
<223> OTHER INFORMATION: Synthetic

<400> SEQUENCE: 8

Leu Leu Phe Glu
1

<210> SEQ ID NO 9
<211> LENGTH: 4
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (3)..(3)
<223> OTHER INFORMATION: Xaa is cyclohexylalanine

<400> SEQUENCE: 9

Ile Ile Xaa Lys
1

<210> SEQ ID NO 10
<211> LENGTH: 4
<212> TYPE: PRT
<213> ORGANISM: Artificial Sequence
<220> FEATURE:
<223> OTHER INFORMATION: Synthetic
<220> FEATURE:
```

```
<221> NAME/KEY: misc_feature
<222> LOCATION: (3)..(3)
<223> OTHER INFORMATION: Xaa is cyclohexylalanine

<400> SEQUENCE: 10

Ile Ile Xaa Arg
1

<210> SEQ ID NO 11
<211> LENGTH: 4
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (3)..(3)
<223> OTHER INFORMATION: Xaa is cyclohexylalanine

<400> SEQUENCE: 11

Ile Ile Xaa Asp
1

<210> SEQ ID NO 12
<211> LENGTH: 4
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (3)..(3)
<223> OTHER INFORMATION: Xaa is cyclohexylalanine

<400> SEQUENCE: 12

Ile Ile Xaa Glu
1

<210> SEQ ID NO 13
<211> LENGTH: 4
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (3)..(3)
<223> OTHER INFORMATION: Xaa is cyclohexylalanine

<400> SEQUENCE: 13

Leu Leu Xaa Lys
1

<210> SEQ ID NO 14
<211> LENGTH: 4
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (3)..(3)
<223> OTHER INFORMATION: Xaa is cyclohexylalanine

<400> SEQUENCE: 14

Leu Leu Xaa Arg
1

<210> SEQ ID NO 15
```

```
<211> LENGTH: 4
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (3)..(3)
<223> OTHER INFORMATION: Xaa is cyclohexylalanine

<400> SEQUENCE: 15

Leu Leu Xaa Asp
1

<210> SEQ ID NO 16
<211> LENGTH: 4
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (3)..(3)
<223> OTHER INFORMATION: Xaa is cyclohexylalanine

<400> SEQUENCE: 16

Leu Leu Xaa Glu
1

<210> SEQ ID NO 17
<211> LENGTH: 4
<212> TYPE: PRT
<213> ORGANISM: Artificial Sequence
<220> FEATURE:
<223> OTHER INFORMATION: Synthetic

<400> SEQUENCE: 17

Ile Phe Phe Lys
1

<210> SEQ ID NO 18
<211> LENGTH: 4
<212> TYPE: PRT
<213> ORGANISM: Artificial Sequence
<220> FEATURE:
<223> OTHER INFORMATION: Synthetic

<400> SEQUENCE: 18

Ile Phe Phe Arg
1

<210> SEQ ID NO 19
<211> LENGTH: 4
<212> TYPE: PRT
<213> ORGANISM: Artificial Sequence
<220> FEATURE:
<223> OTHER INFORMATION: Synthetic

<400> SEQUENCE: 19

Ile Phe Phe Asp
1

<210> SEQ ID NO 20
<211> LENGTH: 4
<212> TYPE: PRT
<213> ORGANISM: Artificial Sequence
<220> FEATURE:
<223> OTHER INFORMATION: Synthetic
```

```
<400> SEQUENCE: 20

Ile Phe Phe Glu
1

<210> SEQ ID NO 21
<211> LENGTH: 4
<212> TYPE: PRT
<213> ORGANISM: Artificial Sequence
<220> FEATURE:
<223> OTHER INFORMATION: Synthetic

<400> SEQUENCE: 21

Leu Phe Phe Lys
1

<210> SEQ ID NO 22
<211> LENGTH: 4
<212> TYPE: PRT
<213> ORGANISM: Artificial Sequence
<220> FEATURE:
<223> OTHER INFORMATION: Synthetic

<400> SEQUENCE: 22

Leu Phe Phe Arg
1

<210> SEQ ID NO 23
<211> LENGTH: 4
<212> TYPE: PRT
<213> ORGANISM: Artificial Sequence
<220> FEATURE:
<223> OTHER INFORMATION: Synthetic

<400> SEQUENCE: 23

Leu Phe Phe Asp
1

<210> SEQ ID NO 24
<211> LENGTH: 4
<212> TYPE: PRT
<213> ORGANISM: Artificial Sequence
<220> FEATURE:
<223> OTHER INFORMATION: Synthetic

<400> SEQUENCE: 24

Leu Phe Phe Glu
1

<210> SEQ ID NO 25
<211> LENGTH: 4
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (2)..(3)
<223> OTHER INFORMATION: Xaa is cyclohexylalanine

<400> SEQUENCE: 25

Ile Xaa Xaa Lys
1

<210> SEQ ID NO 26
<211> LENGTH: 4
<212> TYPE: PRT
<213> ORGANISM: Artificial Sequence
```

```
<220> FEATURE:
<223> OTHER INFORMATION: Synthetic
<220> FEATURE:
<221> NAME/KEY: misc_feature
<222> LOCATION: (2)..(3)
<223> OTHER INFORMATION: Xaa is cyclohexylalanine

<400> SEQUENCE: 26

Ile Xaa Xaa Arg
1

<210> SEQ ID NO 27
<211> LENGTH: 4
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (2)..(3)
<223> OTHER INFORMATION: Xaa is cyclohexylalanine

<400> SEQUENCE: 27

Ile Xaa Xaa Asp
1

<210> SEQ ID NO 28
<211> LENGTH: 4
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (2)..(3)
<223> OTHER INFORMATION: Xaa is cyclohexylalanine

<400> SEQUENCE: 28

Ile Xaa Xaa Glu
1

<210> SEQ ID NO 29
<211> LENGTH: 4
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (2)..(3)
<223> OTHER INFORMATION: Xaa is cyclohexylalanine

<400> SEQUENCE: 29

Leu Xaa Xaa Lys
1

<210> SEQ ID NO 30
<211> LENGTH: 4
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (2)..(3)
<223> OTHER INFORMATION: Xaa is cyclohexylalanine

<400> SEQUENCE: 30

Leu Xaa Xaa Arg
1
```

```
<210> SEQ ID NO 31
<211> LENGTH: 4
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (2)..(3)
<223> OTHER INFORMATION: Xaa is cyclohexylalanine

<400> SEQUENCE: 31

Leu Xaa Xaa Asp
1

<210> SEQ ID NO 32
<211> LENGTH: 4
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (2)..(3)
<223> OTHER INFORMATION: Xaa is cyclohexylalanine

<400> SEQUENCE: 32

Leu Xaa Xaa Glu
1

<210> SEQ ID NO 33
<211> LENGTH: 4
<212> TYPE: PRT
<213> ORGANISM: Artificial Sequence
<220> FEATURE:
<223> OTHER INFORMATION: Synthetic

<400> SEQUENCE: 33

Phe Phe Ile Lys
1

<210> SEQ ID NO 34
<211> LENGTH: 4
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(2)
<223> OTHER INFORMATION: Xaa is cyclohexylalanine

<400> SEQUENCE: 34

Xaa Xaa Ile Arg
1

<210> SEQ ID NO 35
<211> LENGTH: 4
<212> TYPE: PRT
<213> ORGANISM: Artificial Sequence
<220> FEATURE:
<223> OTHER INFORMATION: Synthetic

<400> SEQUENCE: 35

Phe Phe Ile Asp
1
```

```
<210> SEQ ID NO 36
<211> LENGTH: 4
<212> TYPE: PRT
<213> ORGANISM: Artificial Sequence
<220> FEATURE:
<223> OTHER INFORMATION: Synthetic

<400> SEQUENCE: 36

Phe Phe Ile Glu
1

<210> SEQ ID NO 37
<211> LENGTH: 4
<212> TYPE: PRT
<213> ORGANISM: Artificial Sequence
<220> FEATURE:
<223> OTHER INFORMATION: Synthetic

<400> SEQUENCE: 37

Phe Phe Leu Lys
1

<210> SEQ ID NO 38
<211> LENGTH: 4
<212> TYPE: PRT
<213> ORGANISM: Artificial Sequence
<220> FEATURE:
<223> OTHER INFORMATION: Synthetic

<400> SEQUENCE: 38

Phe Phe Leu Arg
1

<210> SEQ ID NO 39
<211> LENGTH: 4
<212> TYPE: PRT
<213> ORGANISM: Artificial Sequence
<220> FEATURE:
<223> OTHER INFORMATION: Synthetic

<400> SEQUENCE: 39

Phe Phe Leu Asp
1

<210> SEQ ID NO 40
<211> LENGTH: 4
<212> TYPE: PRT
<213> ORGANISM: Artificial Sequence
<220> FEATURE:
<223> OTHER INFORMATION: Synthetic

<400> SEQUENCE: 40

Phe Phe Leu Glu
1

<210> SEQ ID NO 41
<211> LENGTH: 4
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(2)
<223> OTHER INFORMATION: Xaa is cyclohexylalanine

<400> SEQUENCE: 41

Xaa Xaa Ile Lys
```

1

```
<210> SEQ ID NO 42
<211> LENGTH: 4
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(2)
<223> OTHER INFORMATION: Xaa is cyclohexylalanine

<400> SEQUENCE: 42

Xaa Xaa Ile Arg
1

<210> SEQ ID NO 43
<211> LENGTH: 4
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(2)
<223> OTHER INFORMATION: Xaa is cyclohexylalanine

<400> SEQUENCE: 43

Xaa Xaa Ile Asp
1

<210> SEQ ID NO 44
<211> LENGTH: 4
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(2)
<223> OTHER INFORMATION: Xaa is cyclohexylalanine

<400> SEQUENCE: 44

Xaa Xaa Ile Glu
1

<210> SEQ ID NO 45
<211> LENGTH: 4
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(2)
<223> OTHER INFORMATION: Xaa is cyclohexylalanine

<400> SEQUENCE: 45

Xaa Xaa Leu Lys
1

<210> SEQ ID NO 46
<211> LENGTH: 4
<212> TYPE: PRT
<213> ORGANISM: Artificial Sequence
<220> FEATURE:
<223> OTHER INFORMATION: Synthetic
<220> FEATURE:
<221> NAME/KEY: misc_feature
```

```
<222> LOCATION: (1)..(2)
<223> OTHER INFORMATION: Xaa is cyclohexylalanine

<400> SEQUENCE: 46

Xaa Xaa Leu Arg
1

<210> SEQ ID NO 47
<211> LENGTH: 4
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(2)
<223> OTHER INFORMATION: Xaa is cyclohexylalanine

<400> SEQUENCE: 47

Xaa Xaa Leu Asp
1

<210> SEQ ID NO 48
<211> LENGTH: 4
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(2)
<223> OTHER INFORMATION: Xaa is cyclohexylalanine

<400> SEQUENCE: 48

Xaa Xaa Leu Glu
1

<210> SEQ ID NO 49
<211> LENGTH: 4
<212> TYPE: PRT
<213> ORGANISM: Artificial Sequence
<220> FEATURE:
<223> OTHER INFORMATION: Synthetic

<400> SEQUENCE: 49

Phe Ile Ile Lys
1

<210> SEQ ID NO 50
<211> LENGTH: 4
<212> TYPE: PRT
<213> ORGANISM: Artificial Sequence
<220> FEATURE:
<223> OTHER INFORMATION: Synthetic

<400> SEQUENCE: 50

Phe Ile Ile Arg
1

<210> SEQ ID NO 51
<211> LENGTH: 4
<212> TYPE: PRT
<213> ORGANISM: Artificial Sequence
<220> FEATURE:
<223> OTHER INFORMATION: Synthetic

<400> SEQUENCE: 51

Phe Ile Ile Asp
```

1

```
<210> SEQ ID NO 52
<211> LENGTH: 4
<212> TYPE: PRT
<213> ORGANISM: Artificial Sequence
<220> FEATURE:
<223> OTHER INFORMATION: Synthetic

<400> SEQUENCE: 52

Phe Ile Ile Glu
1

<210> SEQ ID NO 53
<211> LENGTH: 4
<212> TYPE: PRT
<213> ORGANISM: Artificial Sequence
<220> FEATURE:
<223> OTHER INFORMATION: Synthetic

<400> SEQUENCE: 53

Phe Leu Leu Lys
1

<210> SEQ ID NO 54
<211> LENGTH: 4
<212> TYPE: PRT
<213> ORGANISM: Artificial Sequence
<220> FEATURE:
<223> OTHER INFORMATION: Synthetic

<400> SEQUENCE: 54

Phe Leu Leu Arg
1

<210> SEQ ID NO 55
<211> LENGTH: 4
<212> TYPE: PRT
<213> ORGANISM: Artificial Sequence
<220> FEATURE:
<223> OTHER INFORMATION: Synthetic

<400> SEQUENCE: 55

Phe Leu Leu Asp
1

<210> SEQ ID NO 56
<211> LENGTH: 4
<212> TYPE: PRT
<213> ORGANISM: Artificial Sequence
<220> FEATURE:
<223> OTHER INFORMATION: Synthetic

<400> SEQUENCE: 56

Phe Leu Leu Glu
1

<210> SEQ ID NO 57
<211> LENGTH: 4
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: Xaa is cyclohexylalanine
```

```
<400> SEQUENCE: 57

Xaa Ile Ile Lys
1

<210> SEQ ID NO 58
<211> LENGTH: 4
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: Xaa is cyclohexylalanine

<400> SEQUENCE: 58

Xaa Ile Ile Arg
1

<210> SEQ ID NO 59
<211> LENGTH: 4
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: Xaa is cyclohexylalanine

<400> SEQUENCE: 59

Xaa Ile Ile Asp
1

<210> SEQ ID NO 60
<211> LENGTH: 4
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: Xaa is cyclohexylalanine

<400> SEQUENCE: 60

Xaa Ile Ile Glu
1

<210> SEQ ID NO 61
<211> LENGTH: 4
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: Xaa is cyclohexylalanine

<400> SEQUENCE: 61

Xaa Leu Leu Lys
1

<210> SEQ ID NO 62
<211> LENGTH: 4
<212> TYPE: PRT
<213> ORGANISM: Artificial Sequence
<220> FEATURE:
```

```
<223> OTHER INFORMATION: Synthetic
<220> FEATURE:
<221> NAME/KEY: misc_feature
<222> LOCATION: (1)..(1)
<223> OTHER INFORMATION: Xaa is cyclohexylalanine

<400> SEQUENCE: 62

Xaa Leu Leu Arg
1

<210> SEQ ID NO 63
<211> LENGTH: 4
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: Xaa is cyclohexylalanine

<400> SEQUENCE: 63

Xaa Leu Leu Asp
1

<210> SEQ ID NO 64
<211> LENGTH: 4
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: Xaa is cyclohexylalanine

<400> SEQUENCE: 64

Xaa Leu Leu Glu
1

<210> SEQ ID NO 65
<211> LENGTH: 4
<212> TYPE: PRT
<213> ORGANISM: Artificial Sequence
<220> FEATURE:
<223> OTHER INFORMATION: Synthetic

<400> SEQUENCE: 65

Phe Phe Phe Lys
1

<210> SEQ ID NO 66
<211> LENGTH: 4
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(3)
<223> OTHER INFORMATION: Xaa is cyclohexylalanine

<400> SEQUENCE: 66

Xaa Xaa Xaa Lys
1
```